(12) United States Patent
Pellegrino et al.

(10) Patent No.: US 12,329,412 B2
(45) Date of Patent: *Jun. 17, 2025

(54) SYSTEMS FOR ACCESSING NERVES WITHIN BONE

(71) Applicant: Relievant Medsystems, Inc., Minneapolis, MN (US)

(72) Inventors: Richard Pellegrino, Leesburg, VA (US); Samit Patel, Palo Alto, CA (US); Harold Carrison, Pleasanton, CA (US)

(73) Assignee: Relievant Medsystems, Inc., Minneapolis, MN (US)

( * ) Notice: Subject to any disclaimer, the term of this patent is extended or adjusted under 35 U.S.C. 154(b) by 1413 days.

This patent is subject to a terminal disclaimer.

(21) Appl. No.: 16/368,453

(22) Filed: Mar. 28, 2019

(65) Prior Publication Data

US 2019/0282268 A1 Sep. 19, 2019

Related U.S. Application Data

(63) Continuation of application No. 15/040,268, filed on Feb. 10, 2016, now Pat. No. 10,265,099, which is a
(Continued)

(51) Int. Cl.
*A61B 18/12* (2006.01)
*A61B 17/16* (2006.01)
(Continued)

(52) U.S. Cl.
CPC .......... *A61B 17/3472* (2013.01); *A61B 17/16* (2013.01); *A61B 17/1642* (2013.01);
(Continued)

(58) Field of Classification Search
CPC ... A61B 1/317; A61B 10/025; A61B 17/1671; A61B 17/1757; A61B 17/3472;
(Continued)

(56) References Cited

U.S. PATENT DOCUMENTS 3,054,881 A 9/1962 Metz et al.
3,062,876 A 11/1962 Pons, Jr. et al.
(Continued)

FOREIGN PATENT DOCUMENTS

AU 2012244378 A1 11/2012
CN 1039542 A 2/1990
(Continued)

OTHER PUBLICATIONS

A Novel Approach for Treating Chronic Lower Back Pain, Abstract for Presentation at North American Spine Society 26th Annual Meeting in Chicago, IL on Nov. 4, 2011.
(Continued)

*Primary Examiner* — Jaymi E Della
(74) *Attorney, Agent, or Firm* — Nelson Mullins Riley & Scarborough LLP

(57) ABSTRACT

System and methods are shown having a tube-within-tube assembly with a deployable curved deflectable tube or cannula that deploys from a straight cannula or trocar. The curved cannula has pre-curved distal end to create an angular range of 0° to 180° when fully deployed from the straight trocar. The curve is configured such that the flexible element carrying a treatment device can navigate through the angular range of deployment of the curved cannula. The curved cannula allows the flexible element to navigate through a curve within bone without veering off towards an unintended direction.

17 Claims, 9 Drawing Sheets

Related U.S. Application Data continuation of application No. 13/862,242, filed on Apr. 12, 2013, now Pat. No. 9,259,241, which is a continuation of application No. 12/566,895, filed on Sep. 25, 2009, now Pat. No. 8,419,730.

(60) Provisional application No. 61/100,553, filed on Sep. 26, 2008.

(51) Int. Cl.

| | | |
|---|---|---|
| *A61B 17/34* | (2006.01) | |
| *A61B 17/56* | (2006.01) | |
| *A61B 17/88* | (2006.01) | |
| *A61B 18/14* | (2006.01) | |
| *A61B 18/18* | (2006.01) | |
| *A61B 18/20* | (2006.01) | |
| *A61N 7/00* | (2006.01) | |
| *A61B 18/00* | (2006.01) | |
| *A61B 18/02* | (2006.01) | |
| *A61N 7/02* | (2006.01) | |

(52) U.S. Cl.
CPC .......... *A61B 17/1671* (2013.01); *A61B 17/34* (2013.01); *A61B 17/3403* (2013.01); *A61B 17/3421* (2013.01); *A61B 17/8819* (2013.01); *A61B 18/14* (2013.01); *A61B 18/148* (2013.01); *A61B 18/1487* (2013.01); *A61B 18/149* (2013.01); *A61B 18/18* (2013.01); *A61B 18/1815* (2013.01); *A61B 18/20* (2013.01); *A61N 7/00* (2013.01); *A61B 2018/00011* (2013.01); *A61B 2018/00017* (2013.01); *A61B 2018/00339* (2013.01); *A61B 2018/00434* (2013.01); *A61B 2018/00577* (2013.01); *A61B 18/0206* (2013.01); *A61B 18/1492* (2013.01); *A61N 2007/0026* (2013.01); *A61N 2007/025* (2013.01)

(58) Field of Classification Search
CPC ... A61B 17/56; A61B 17/809; A61B 17/8819; A61B 18/0206; A61B 18/148; A61B 18/1492; A61B 18/18; A61B 18/20; A61B 2017/347; A61B 2017/3472; A61B 2018/00011; A61B 2018/00339; A61B 2018/0044; A61B 2018/00565; A61B 5/4504; A61B 5/6878
See application file for complete search history.

(56) References Cited

U.S. PATENT DOCUMENTS

| | | |
|---|---|---|
| 3,565,062 A | 2/1971 | Kuris |
| 3,822,708 A | 7/1974 | Zilber |
| 3,845,771 A | 11/1974 | Vise |
| 3,920,021 A | 11/1975 | Hiltebrandt |
| 3,938,502 A | 2/1976 | Born |
| 3,977,408 A | 8/1976 | MacKew |
| 3,997,408 A | 8/1976 | MacKew |
| 4,044,774 A | 8/1977 | Corgin et al. |
| 4,116,198 A | 9/1978 | Roos |
| 4,311,154 A | 1/1982 | Sterzer et al. |
| 4,312,364 A | 1/1982 | Convert et al. |
| 4,378,806 A | 4/1983 | Henley-Cohn |
| 4,448,198 A | 5/1984 | Turner |
| 4,449,528 A | 5/1984 | Auth et al. |
| 4,462,408 A | 7/1984 | Silverstein et al. |
| 4,528,979 A | 7/1985 | Marchenko et al. |
| 4,530,360 A | 7/1985 | Duarte |
| 4,541,423 A | 9/1985 | Barber |
| 4,569,351 A | 2/1986 | Tang |
| 4,573,448 A | 3/1986 | Kambin |
| 4,586,512 A | 5/1986 | Do-huu |
| 4,601,296 A | 7/1986 | Yerushalmi |
| 4,612,940 A | 9/1986 | Kasevich et al. |
| 4,657,017 A | 4/1987 | Sorochenko |
| 4,662,383 A | 5/1987 | Sogawa et al. |
| 4,671,293 A | 6/1987 | Shaulov |
| 4,676,258 A | 6/1987 | Inokuchi et al. |
| 4,679,561 A | 7/1987 | Doss |
| 4,681,122 A | 7/1987 | Winters et al. |
| 4,750,499 A | 6/1988 | Hoffer |
| 4,754,757 A | 7/1988 | Feucht |
| 4,757,820 A | 7/1988 | Itoh |
| 4,774,967 A | 10/1988 | Zanakis et al. |
| 4,800,899 A | 1/1989 | Elliott |
| 4,813,429 A | 3/1989 | Eshel et al. |
| 4,841,977 A | 6/1989 | Griffith et al. |
| 4,907,589 A | 3/1990 | Cosman |
| 4,912,077 A | 3/1990 | Lachman et al. |
| 4,924,863 A | 5/1990 | Sterzer |
| 4,936,281 A | 6/1990 | Stasz |
| 4,941,466 A | 7/1990 | Romano |
| 4,950,267 A | 8/1990 | Ishihara et al. |
| 4,951,677 A | 8/1990 | Crowley et al. |
| 4,955,377 A | 9/1990 | Lennox et al. |
| 4,959,063 A | 9/1990 | Kojima |
| 4,961,435 A | 10/1990 | Kitagawa et al. |
| 4,963,142 A | 10/1990 | Loertscher |
| 4,966,144 A | 10/1990 | Rochkind et al. |
| 4,967,765 A | 11/1990 | Turner et al. |
| 4,976,711 A | 12/1990 | Parins et al. |
| 4,977,902 A | 12/1990 | Sekino et al. |
| 5,000,185 A | 3/1991 | Yock |
| 5,002,058 A | 3/1991 | Marinelli |
| 5,002,059 A | 3/1991 | Crowley et al. |
| 5,007,437 A | 4/1991 | Sterzer |
| 5,025,778 A | 6/1991 | Silverstein et al. |
| 5,031,618 A | 7/1991 | Mullet |
| 5,061,266 A | 10/1991 | Hakky |
| 5,070,879 A | 12/1991 | Herres |
| RE33,791 E | 1/1992 | Carr |
| 5,078,736 A | 1/1992 | Behl |
| 5,080,660 A | 1/1992 | Buelna |
| 5,084,043 A | 1/1992 | Hertzmann et al. |
| 5,090,414 A | 2/1992 | Takano |
| 5,098,431 A | 3/1992 | Rydell |
| 5,106,376 A | 4/1992 | Mononen et al. |
| 5,108,404 A | 4/1992 | Scholten et al. |
| 5,131,397 A | 7/1992 | Crowley |
| 5,147,355 A | 9/1992 | Friedman et al. |
| 5,156,157 A | 10/1992 | Valenta, Jr. et al. |
| 5,158,536 A | 10/1992 | Sekins et al. |
| 5,161,533 A | 11/1992 | Prass et al. |
| 5,167,231 A | 12/1992 | Matsui |
| 5,186,177 A | 2/1993 | O'Donnell et al. |
| 5,189,177 A | 2/1993 | Blacklock et al. |
| 5,190,540 A | 3/1993 | Lee |
| 5,190,546 A | 3/1993 | Jervis |
| 5,201,729 A | 4/1993 | Hertzmann et al. |
| 5,207,672 A | 5/1993 | Martinelli et al. |
| 5,209,748 A | 5/1993 | Daikuzono |
| 5,222,953 A | 6/1993 | Dowlatshahi |
| 5,226,430 A | 7/1993 | Spear et al. |
| 5,242,439 A | 9/1993 | Larsen et al. |
| 5,255,679 A | 10/1993 | Imran |
| 5,271,408 A | 12/1993 | Breyer et al. |
| 5,273,026 A | 12/1993 | Wilk |
| 5,281,213 A | 1/1994 | Milder et al. |
| 5,281,215 A | 1/1994 | Milder et al. |
| 5,282,468 A | 2/1994 | Klepenski |
| 5,292,321 A | 3/1994 | Lee |
| 5,295,484 A | 3/1994 | Marcus et al. |
| 5,300,085 A | 4/1994 | Yock |
| 5,304,214 A | 4/1994 | DeFord et al. |
| 5,305,756 A | 4/1994 | Entrikin et al. |
| 5,314,463 A | 5/1994 | Camps et al. |
| 5,320,617 A | 6/1994 | Leach |
| 5,324,255 A | 6/1994 | Pasafaro et al. |
| 5,325,860 A | 7/1994 | Seward et al. |
| 5,342,292 A | 8/1994 | Nita et al. |

(56) References Cited

U.S. PATENT DOCUMENTS

| | | |
|---|---|---|
| 5,342,357 A | 8/1994 | Nardella |
| 5,342,409 A | 8/1994 | Mullett |
| 5,344,435 A | 9/1994 | Turner et al. |
| 5,345,940 A | 9/1994 | Seward et al. |
| 5,348,554 A | 9/1994 | Imran et al. |
| 5,350,377 A | 9/1994 | Winston et al. |
| 5,351,691 A | 10/1994 | Brommersma |
| 5,366,443 A | 11/1994 | Eggers et al. |
| 5,366,490 A | 11/1994 | Edwards et al. |
| 5,368,031 A | 11/1994 | Cline et al. |
| 5,368,035 A | 11/1994 | Hamm et al. |
| 5,368,557 A | 11/1994 | Nita et al. |
| 5,368,558 A | 11/1994 | Nita |
| 5,370,675 A | 12/1994 | Edwards et al. |
| 5,370,678 A | 12/1994 | Edwards et al. |
| 5,372,138 A | 12/1994 | Crowley et al. |
| 5,374,265 A | 12/1994 | Sand |
| 5,383,876 A | 1/1995 | Nardella |
| 5,385,148 A | 1/1995 | Lesh et al. |
| 5,385,544 A | 1/1995 | Edwards et al. |
| 5,391,197 A | 2/1995 | Burdette et al. |
| 5,391,199 A | 2/1995 | Ben-Haim |
| 5,405,376 A | 4/1995 | Mulier et al. |
| 5,411,527 A | 5/1995 | Alt |
| 5,417,719 A | 5/1995 | Hull et al. |
| 5,419,767 A | 5/1995 | Eggers et al. |
| 5,421,338 A | 6/1995 | Crowley |
| 5,423,811 A | 6/1995 | Imran et al. |
| 5,431,649 A | 7/1995 | Mulier et al. |
| 5,433,739 A | 7/1995 | Sluijter et al. |
| D361,555 S | 8/1995 | Bettin et al. |
| 5,437,661 A | 8/1995 | Rieser |
| 5,441,499 A | 8/1995 | Fritzsch |
| 5,441,527 A | 8/1995 | Erickson et al. |
| 5,443,463 A | 8/1995 | Stern et al. |
| 5,447,509 A | 9/1995 | Millis et al. |
| 5,449,380 A | 9/1995 | Chin |
| 5,454,373 A | 10/1995 | Koger et al. |
| 5,458,596 A | 10/1995 | Lax et al. |
| 5,458,597 A | 10/1995 | Edwards et al. |
| 5,471,988 A | 12/1995 | Fujio et al. |
| 5,472,441 A | 12/1995 | Edwards et al. |
| 5,474,530 A | 12/1995 | Passafaro et al. |
| 5,484,432 A | 1/1996 | Sand |
| 5,486,170 A | 1/1996 | Winston et al. |
| 5,501,703 A | 3/1996 | Holscheimer et al. |
| 5,505,730 A | 4/1996 | Edwards |
| 5,514,130 A | 5/1996 | Baker |
| 5,524,624 A | 6/1996 | Tepper et al. |
| 5,526,815 A | 6/1996 | Granz et al. |
| 5,529,580 A | 6/1996 | Hagino et al. |
| 5,540,679 A | 7/1996 | Fram et al. |
| 5,540,681 A | 7/1996 | Strul et al. |
| 5,540,684 A | 7/1996 | Hassler, Jr. |
| 5,545,161 A | 8/1996 | Imran |
| 5,560,362 A | 10/1996 | Silwa, Jr. et al. |
| 5,565,005 A | 10/1996 | Erickson et al. |
| 5,569,242 A | 10/1996 | Lax et al. |
| 5,571,088 A | 11/1996 | Lennox et al. |
| 5,571,147 A | 11/1996 | Sluijter et al. |
| 5,575,772 A | 11/1996 | Lennox |
| 5,575,788 A | 11/1996 | Baker et al. |
| 5,588,432 A | 12/1996 | Crowley |
| 5,596,988 A | 1/1997 | Markle et al. |
| 5,601,526 A | 2/1997 | Chapelon et al. |
| 5,606,974 A | 3/1997 | Castellano et al. |
| 5,609,151 A | 3/1997 | Mulier et al. |
| 5,620,479 A | 4/1997 | Diederich |
| 5,628,317 A | 5/1997 | Starkebaum et al. |
| 5,630,426 A | 5/1997 | Shmulewitz et al. |
| 5,630,837 A | 5/1997 | Crowley |
| 5,643,319 A | 7/1997 | Green et al. |
| 5,643,330 A | 7/1997 | Holsheimer et al. |
| 5,647,361 A | 7/1997 | Damadian |
| 5,647,871 A | 7/1997 | Levine et al. |
| 5,658,278 A | 8/1997 | Imran et al. |
| 5,672,173 A | 9/1997 | Gough et al. |
| 5,681,282 A | 10/1997 | Eggers et al. |
| 5,683,267 A | 11/1997 | Ribbeck et al. |
| 5,683,366 A | 11/1997 | Eggers et al. |
| 5,685,839 A | 11/1997 | Baker et al. |
| 5,687,729 A | 11/1997 | Schaetzle |
| 5,688,267 A | 11/1997 | Panescu |
| 5,693,052 A | 12/1997 | Weaver |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,697,927 A | 12/1997 | Imran et al. |
| 5,700,262 A | 12/1997 | Acosta et al. |
| 5,718,231 A | 2/1998 | Chen et al. |
| 5,720,286 A | 2/1998 | Chapelon et al. |
| 5,720,287 A | 2/1998 | Chapelon et al. |
| 5,722,403 A | 3/1998 | McGee et al. |
| 5,725,494 A | 3/1998 | Brisken |
| 5,728,062 A | 3/1998 | Brisken |
| 5,730,706 A | 3/1998 | Garnies |
| 5,733,280 A | 3/1998 | Avitall |
| 5,733,315 A | 3/1998 | Burdette et al. |
| 5,733,861 A | 3/1998 | Gopalkrishnan et al. |
| 5,735,280 A | 4/1998 | Sherman et al. |
| 5,735,811 A | 4/1998 | Brisken |
| 5,735,846 A | 4/1998 | Fleischman et al. |
| 5,735,847 A | 4/1998 | Gough et al. |
| 5,738,680 A | 4/1998 | Mueller et al. |
| 5,741,249 A | 4/1998 | Moss et al. |
| 5,743,904 A | 4/1998 | Edwards |
| 5,746,737 A | 5/1998 | Saadat |
| 5,752,969 A | 5/1998 | Cunci et al. |
| 5,755,663 A | 5/1998 | Johnson et al. |
| 5,762,066 A | 6/1998 | Law et al. |
| 5,762,616 A | 6/1998 | Talish |
| 5,766,092 A | 6/1998 | Mimeur et al. |
| 5,766,153 A | 6/1998 | Eggers et al. |
| 5,766,231 A | 6/1998 | Erickson et al. |
| 5,776,092 A | 7/1998 | Farin et al. |
| 5,785,705 A | 7/1998 | Baker |
| 5,800,378 A | 9/1998 | Edwards et al. |
| 5,800,429 A | 9/1998 | Edwards |
| 5,800,432 A | 9/1998 | Swason |
| 5,807,237 A | 9/1998 | Tindel |
| 5,807,391 A | 9/1998 | Wijkamp |
| 5,807,392 A | 9/1998 | Eggers |
| 5,807,395 A | 9/1998 | Mulier et al. |
| 5,810,764 A | 9/1998 | Eggers et al. |
| 5,817,021 A | 10/1998 | Reichenberger |
| 5,824,021 A | 10/1998 | Rise |
| 5,840,031 A | 11/1998 | Crowley |
| 5,843,019 A | 12/1998 | Eggers et al. |
| 5,843,021 A | 12/1998 | Edwards et al. |
| 5,844,092 A | 12/1998 | Presta et al. |
| 5,846,218 A | 12/1998 | Brisken et al. |
| 5,849,011 A | 12/1998 | Jones et al. |
| 5,855,576 A | 1/1999 | LeVeen et al. |
| 5,860,951 A | 1/1999 | Eggers et al. |
| 5,865,788 A | 2/1999 | Edwards et al. |
| 5,865,801 A | 2/1999 | Houser |
| 5,868,740 A | 2/1999 | LeVeen et al. |
| 5,871,469 A | 2/1999 | Eggers et al. |
| 5,871,470 A | 2/1999 | McWha |
| 5,871,481 A | 2/1999 | Kannenberg et al. |
| 5,873,677 A | 2/1999 | Davies et al. |
| 5,873,855 A | 2/1999 | Eggers et al. |
| 5,873,877 A | 2/1999 | McGaffigan et al. |
| 5,876,398 A | 3/1999 | Mulier et al. |
| 5,888,198 A | 3/1999 | Eggers et al. |
| 5,891,095 A | 4/1999 | Eggers et al. |
| 5,895,370 A | 4/1999 | Edwards et al. |
| 5,902,272 A | 5/1999 | Eggers et al. |
| 5,902,308 A | 5/1999 | Murphy |
| 5,904,681 A | 5/1999 | West, Jr. |
| 5,906,613 A | 5/1999 | Mulier et al. |
| 5,916,213 A | 6/1999 | Haissaguerre et al. |
| 5,916,214 A | 6/1999 | Cosio |

(56) References Cited

U.S. PATENT DOCUMENTS

| | | |
|---|---|---|
| 5,919,188 A | 7/1999 | Shearon et al. |
| 5,931,805 A | 8/1999 | Brisken |
| 5,935,123 A | 8/1999 | Edwards et al. |
| 5,938,582 A | 8/1999 | Ciamacco et al. |
| 5,941,722 A | 8/1999 | Chen |
| 5,941,876 A | 8/1999 | Nardella et al. |
| 5,943,008 A | 8/1999 | Van Dusseldorp |
| 5,944,715 A | 8/1999 | Goble et al. |
| 5,948,007 A | 9/1999 | Starkebaum et al. |
| 5,948,008 A | 9/1999 | Daikuzono |
| 5,954,716 A | 9/1999 | Sharkey et al. |
| 5,964,727 A | 10/1999 | Edwards et al. |
| 5,967,988 A | 10/1999 | Briscoe et al. |
| 5,972,015 A | 10/1999 | Scribner et al. |
| 5,976,105 A | 11/1999 | Marcove et al. |
| 5,983,141 A | 11/1999 | Sluijter et al. |
| 5,997,497 A | 12/1999 | Nita et al. |
| 6,001,095 A | 12/1999 | de la Rama et al. |
| 6,007,533 A | 12/1999 | Casscells et al. |
| 6,007,570 A | 12/1999 | Sharkey et al. |
| 6,012,457 A | 1/2000 | Lesh |
| 6,014,588 A | 1/2000 | Fitz |
| 6,016,452 A | 1/2000 | Kasevich |
| 6,016,809 A | 1/2000 | Mulier et al. |
| 6,017,356 A | 1/2000 | Frederick et al. |
| 6,019,776 A | 2/2000 | Preissman et al. |
| 6,022,334 A | 2/2000 | Edwards et al. |
| 6,024,733 A | 2/2000 | Eggers et al. |
| 6,024,740 A | 2/2000 | Lesh et al. |
| 6,030,374 A | 2/2000 | McDaniel |
| 6,030,402 A | 2/2000 | Thompson et al. |
| 6,032,673 A | 3/2000 | Langberg et al. |
| 6,032,674 A | 3/2000 | Eggers et al. |
| 6,033,411 A | 3/2000 | Preissman |
| 6,035,238 A | 3/2000 | Ingle et al. |
| 6,038,480 A | 3/2000 | Hrdlicka et al. |
| 6,045,532 A | 4/2000 | Eggers et al. |
| 6,046,187 A | 4/2000 | Berde et al. |
| 6,047,214 A | 4/2000 | Mueller et al. |
| 6,050,995 A | 4/2000 | Durgin |
| 6,050,998 A | 4/2000 | Fletcher |
| 6,053,172 A | 4/2000 | Hovda et al. |
| 6,053,909 A | 4/2000 | Shadduck |
| 6,056,745 A | 5/2000 | Panescu et al. |
| 6,063,078 A | 5/2000 | Wittkampf |
| 6,063,079 A | 5/2000 | Hovda et al. |
| 6,066,134 A | 5/2000 | Eggers et al. |
| 6,066,139 A | 5/2000 | Ryan et al. |
| 6,068,642 A | 5/2000 | Johnson et al. |
| 6,071,279 A | 6/2000 | Whayne et al. |
| 6,073,051 A | 6/2000 | Sharkey et al. |
| 6,074,352 A | 6/2000 | Hynynen et al. |
| 6,086,585 A | 7/2000 | Hovda et al. |
| 6,090,105 A | 7/2000 | Zepeda et al. |
| 6,095,149 A | 8/2000 | Sharkey et al. |
| 6,099,499 A | 8/2000 | Ciamacco |
| 6,099,514 A | 8/2000 | Sharkey et al. |
| 6,099,524 A | 8/2000 | Lipson et al. |
| 6,102,046 A | 8/2000 | Weinstein et al. |
| 6,104,957 A | 8/2000 | Alo et al. |
| 6,105,581 A | 8/2000 | Eggers et al. |
| 6,106,454 A | 8/2000 | Berg et al. |
| 6,109,268 A | 8/2000 | Thapliyal et al. |
| 6,112,122 A | 8/2000 | Schwardt et al. |
| 6,113,597 A | 9/2000 | Eggers et al. |
| 6,117,101 A | 9/2000 | Diederich et al. |
| 6,117,109 A | 9/2000 | Eggers et al. |
| 6,117,128 A | 9/2000 | Gregory |
| 6,120,467 A | 9/2000 | Schallhorn |
| 6,120,502 A | 9/2000 | Michelson |
| 6,122,549 A | 9/2000 | Sharkey et al. |
| 6,126,682 A | 10/2000 | Ashley et al. |
| 6,137,209 A | 10/2000 | Dahlberg et al. |
| 6,139,545 A | 10/2000 | Utley et al. |
| 6,142,992 A | 11/2000 | Cheng et al. |
| 6,143,019 A | 11/2000 | Motamedi et al. |
| 6,146,380 A | 11/2000 | Racz et al. |
| 6,149,620 A | 11/2000 | Baker et al. |
| 6,159,194 A | 12/2000 | Eggers et al. |
| 6,159,208 A | 12/2000 | Hovda et al. |
| 6,161,048 A | 12/2000 | Sluijter et al. |
| 6,164,283 A | 12/2000 | Lesh |
| 6,165,172 A | 12/2000 | Farley et al. |
| 6,168,593 B1 | 1/2001 | Sharkey et al. |
| 6,169,924 B1 | 1/2001 | Meloy et al. |
| 6,171,239 B1 | 1/2001 | Humphrey |
| 6,176,857 B1 | 1/2001 | Ashley |
| 6,179,824 B1 | 1/2001 | Eggers et al. |
| 6,179,836 B1 | 1/2001 | Eggers et al. |
| 6,179,858 B1 | 1/2001 | Squire et al. |
| 6,183,469 B1 | 2/2001 | Thapliyal et al. |
| 6,190,381 B1 | 2/2001 | Olsen et al. |
| 6,190,383 B1 | 2/2001 | Schmaltz et al. |
| 6,193,715 B1 | 2/2001 | Wrublewski et al. |
| 6,203,542 B1 | 3/2001 | Ellsberry et al. |
| 6,206,842 B1 | 3/2001 | Tu et al. |
| 6,210,393 B1 | 4/2001 | Brisken |
| 6,210,402 B1 | 4/2001 | Olsen et al. |
| 6,210,415 B1 | 4/2001 | Bester |
| 6,216,704 B1 | 4/2001 | Ingle et al. |
| 6,221,038 B1 | 4/2001 | Brisken |
| 6,224,592 B1 | 5/2001 | Eggers et al. |
| 6,228,046 B1 | 5/2001 | Brisken |
| 6,228,078 B1 | 5/2001 | Eggers et al. |
| 6,228,082 B1 | 5/2001 | Baker et al. |
| 6,231,516 B1 | 5/2001 | Keilman et al. |
| 6,231,528 B1 | 5/2001 | Kaufman et al. |
| 6,231,571 B1 | 5/2001 | Ellman et al. |
| 6,231,615 B1 | 5/2001 | Preissman |
| 6,233,488 B1 | 5/2001 | Hess |
| 6,235,020 B1 | 5/2001 | Cheng et al. |
| 6,235,022 B1 | 5/2001 | Hallock et al. |
| 6,235,024 B1 | 5/2001 | Tu |
| 6,237,604 B1 | 5/2001 | Burnside et al. |
| 6,238,391 B1 | 5/2001 | Olsen et al. |
| 6,238,393 B1 | 5/2001 | Mulier et al. |
| 6,241,665 B1 | 6/2001 | Negus et al. |
| 6,241,725 B1 | 6/2001 | Cosman |
| 6,241,734 B1 | 6/2001 | Scribner et al. |
| 6,245,064 B1 | 6/2001 | Lesh |
| 6,246,912 B1 | 6/2001 | Sluijter et al. |
| 6,248,110 B1 | 6/2001 | Reiley et al. |
| 6,248,345 B1 | 6/2001 | Goldenheim et al. |
| 6,254,553 B1 | 7/2001 | Lidgren et al. |
| 6,254,599 B1 | 7/2001 | Lesh et al. |
| 6,254,600 B1 | 7/2001 | Willink et al. |
| 6,258,086 B1 | 7/2001 | Ashley et al. |
| 6,259,952 B1 | 7/2001 | Sluijter |
| 6,261,311 B1 | 7/2001 | Sharkey et al. |
| 6,264,650 B1 | 7/2001 | Hovda et al. |
| 6,264,651 B1 | 7/2001 | Underwood et al. |
| 6,264,652 B1 | 7/2001 | Eggers et al. |
| 6,264,659 B1 | 7/2001 | Ross et al. |
| 6,267,770 B1 | 7/2001 | Truwit |
| 6,270,498 B1 | 8/2001 | Michelson |
| 6,277,112 B1 | 8/2001 | Underwood et al. |
| 6,277,122 B1 | 8/2001 | McGahan et al. |
| 6,280,441 B1 | 8/2001 | Ryan |
| 6,280,456 B1 | 8/2001 | Scribner et al. |
| 6,283,961 B1 | 9/2001 | Underwood et al. |
| 6,287,114 B1 | 9/2001 | Meller et al. |
| 6,287,272 B1 | 9/2001 | Brisken et al. |
| 6,287,304 B1 | 9/2001 | Eggers et al. |
| 6,290,715 B1 | 9/2001 | Sharkey et al. |
| 6,292,699 B1 | 9/2001 | Simon et al. |
| 6,296,619 B1 | 10/2001 | Brisken et al. |
| 6,296,636 B1 | 10/2001 | Cheng et al. |
| 6,296,638 B1 | 10/2001 | Davison et al. |
| 6,305,378 B1 | 10/2001 | Lesh et al. |
| 6,309,387 B1 | 10/2001 | Eggers et al. |
| 6,309,420 B1 | 10/2001 | Preissman |
| 6,312,408 B1 | 11/2001 | Eggers et al. |
| 6,312,425 B1 | 11/2001 | Simpson et al. |
| 6,312,426 B1 | 11/2001 | Goldberg et al. |

(56) References Cited

U.S. PATENT DOCUMENTS

| | | |
|---|---|---|
| 6,319,241 B1 | 11/2001 | King et al. |
| 6,322,549 B1 | 11/2001 | Eggers et al. |
| 6,348,055 B1 | 2/2002 | Preissman |
| 6,355,032 B1 | 3/2002 | Hovda et al. |
| 6,356,790 B1 | 3/2002 | Maguire et al. |
| 6,361,531 B1 | 3/2002 | Hissong |
| 6,363,937 B1 | 4/2002 | Hovda et al. |
| 6,368,292 B1 | 4/2002 | Ogden et al. |
| 6,379,351 B1 | 4/2002 | Thapliyal et al. |
| 6,383,190 B1 | 5/2002 | Preissman |
| 6,391,025 B1 | 5/2002 | Weinstein et al. |
| 6,398,732 B1 | 6/2002 | Brock-Fisher et al. |
| 6,398,782 B1 | 6/2002 | Pecor et al. |
| 6,416,507 B1 | 7/2002 | Eggers et al. |
| 6,416,508 B1 | 7/2002 | Eggers et al. |
| 6,423,057 B1 | 7/2002 | He et al. |
| 6,423,059 B1 | 7/2002 | Hanson et al. |
| 6,425,887 B1 | 7/2002 | McGuckin et al. |
| 6,426,339 B1 | 7/2002 | Berde et al. |
| 6,428,491 B1 | 8/2002 | Weiss |
| 6,432,103 B1 | 8/2002 | Ellsberry et al. |
| 6,436,060 B1 | 8/2002 | Talish |
| 6,436,098 B1 | 8/2002 | Michelson |
| 6,440,138 B1 | 8/2002 | Reiley et al. |
| 6,447,448 B1 | 9/2002 | Ishikawa et al. |
| 6,451,013 B1 | 9/2002 | Bays et al. |
| 6,454,727 B1 | 9/2002 | Bubank et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,468,270 B1 | 10/2002 | Hovda et al. |
| 6,468,274 B1 | 10/2002 | Alleyne et al. |
| 6,470,220 B1 | 10/2002 | Kraus et al. |
| 6,478,793 B1 | 11/2002 | Cosman et al. |
| 6,482,201 B1 | 11/2002 | Olsen et al. |
| 6,485,271 B1 | 11/2002 | Tack |
| 6,487,446 B1 | 11/2002 | Hill et al. |
| 6,491,893 B1 | 12/2002 | Babich |
| 6,493,592 B1 | 12/2002 | Leonard et al. |
| 6,494,902 B2 | 12/2002 | Hoey et al. |
| 6,500,173 B2 | 12/2002 | Underwood et al. |
| 6,503,339 B1 | 1/2003 | Pircher et al. |
| 6,505,075 B1 | 1/2003 | Weiner |
| 6,508,839 B1 | 1/2003 | Lambrecht et al. |
| 6,524,261 B2 | 2/2003 | Talish et al. |
| 6,527,759 B1 | 3/2003 | Tachibana et al. |
| 6,537,306 B1 | 3/2003 | Burdette et al. |
| 6,540,741 B1 | 4/2003 | Underwood et al. |
| 6,544,261 B2 | 4/2003 | Ellsberry et al. |
| 6,557,559 B1 | 5/2003 | Eggers et al. |
| 6,558,385 B1 | 5/2003 | McClurken et al. |
| 6,558,390 B2 | 5/2003 | Cragg |
| 6,560,486 B1 | 5/2003 | Osorio et al. |
| 6,562,033 B2 | 5/2003 | Shah et al. |
| 6,575,919 B1 | 6/2003 | Reiley et al. |
| 6,575,968 B1 | 6/2003 | Eggers et al. |
| 6,575,969 B1 | 6/2003 | Rittman, III et al. |
| 6,575,979 B1 | 6/2003 | Cragg |
| 6,578,579 B2 | 6/2003 | Burnside et al. |
| 6,582,423 B1 | 6/2003 | Thapliyal et al. |
| 6,585,656 B2 | 7/2003 | Masters |
| 6,589,237 B2 | 7/2003 | Woloszko et al. |
| 6,592,559 B1 | 7/2003 | Pakter et al. |
| 6,595,990 B1 | 7/2003 | Weinstein et al. |
| 6,599,288 B2 | 7/2003 | Maguire et al. |
| 6,602,248 B1 | 8/2003 | Sharps et al. |
| 6,604,003 B2 | 8/2003 | Fredricks et al. |
| 6,607,502 B1 | 8/2003 | Maguire et al. |
| 6,607,529 B1 | 8/2003 | Jones et al. |
| 6,608,502 B2 | 8/2003 | Aoki et al. |
| 6,622,731 B2 | 9/2003 | Daniel et al. |
| 6,623,505 B2 | 9/2003 | Scribner et al. |
| 6,632,193 B1 | 10/2003 | Davison et al. |
| 6,632,220 B1 | 10/2003 | Eggers et al. |
| 6,645,202 B1 | 11/2003 | Pless et al. |
| 6,648,883 B2 | 11/2003 | Francischelli et al. |
| 6,651,669 B1 | 11/2003 | Burnside |
| 6,659,106 B1 | 12/2003 | Hovda et al. |
| 6,663,627 B2 | 12/2003 | Francischelli et al. |
| 6,663,647 B2 | 12/2003 | Reiley et al. |
| 6,673,063 B2 | 1/2004 | Brett |
| 6,689,086 B1 | 2/2004 | Nita et al. |
| 6,689,125 B1 | 2/2004 | Keith et al. |
| 6,692,450 B1 | 2/2004 | Coleman |
| 6,699,240 B2 | 3/2004 | Francischelli |
| 6,699,242 B2 * | 3/2004 | Heggeness ............ A61B 18/148 606/41 |
| 6,709,432 B2 | 3/2004 | Ferek-Patric |
| 6,718,208 B2 | 4/2004 | Hill et al. |
| 6,719,761 B1 | 4/2004 | Reiley et al. |
| 6,723,087 B2 | 4/2004 | O'Neill et al. |
| 6,723,094 B1 | 4/2004 | Desinger |
| 6,726,684 B1 | 4/2004 | Woloszko et al. |
| 6,736,810 B2 | 5/2004 | Hoey et al. |
| 6,736,835 B2 | 5/2004 | Pellegrino et al. |
| 6,745,079 B2 | 6/2004 | King |
| 6,746,447 B2 | 6/2004 | Davison et al. |
| 6,746,451 B2 | 6/2004 | Middleton et al. |
| 6,749,604 B1 | 6/2004 | Eggers et al. |
| 6,758,846 B2 | 7/2004 | Goble et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,795,737 B2 | 9/2004 | Gielen et al. |
| 6,805,697 B1 | 10/2004 | Helm et al. |
| 6,827,715 B2 | 12/2004 | Francischelli et al. |
| 6,827,716 B2 | 12/2004 | Ryan et al. |
| 6,832,996 B2 | 12/2004 | Woloszko et al. |
| 6,837,887 B2 | 1/2005 | Woloszko et al. |
| 6,837,888 B2 | 1/2005 | Ciarrocca et al. |
| 6,852,091 B2 | 2/2005 | Edwards et al. |
| 6,863,672 B2 | 3/2005 | Reiley et al. |
| 6,875,219 B2 | 4/2005 | Arramon et al. |
| 6,881,214 B2 | 4/2005 | Cosman et al. |
| 6,896,674 B1 | 5/2005 | Woloszko et al. |
| 6,896,675 B2 | 5/2005 | Leung et al. |
| 6,907,884 B2 | 6/2005 | Pellegrino et al. |
| 6,915,806 B2 | 7/2005 | Pacek et al. |
| 6,922,579 B2 | 7/2005 | Taimisto et al. |
| 6,923,813 B2 | 8/2005 | Phillips et al. |
| 6,936,046 B2 | 8/2005 | Hissong et al. |
| 6,955,674 B2 | 10/2005 | Eick et al. |
| 6,960,204 B2 | 11/2005 | Eggers et al. |
| 6,962,589 B2 | 11/2005 | Mulier et al. |
| 6,974,453 B2 | 12/2005 | Woloszko et al. |
| 6,980,849 B2 | 12/2005 | Sasso |
| 6,981,981 B2 | 1/2006 | Reiley et al. |
| 6,989,010 B2 | 1/2006 | Francischelli et al. |
| 6,997,941 B2 | 2/2006 | Sharkey et al. |
| 7,001,383 B2 | 2/2006 | Keidar |
| 7,041,096 B2 | 5/2006 | Malis et al. |
| 7,044,954 B2 | 5/2006 | Reiley et al. |
| 7,048,743 B2 | 5/2006 | Miller et al. |
| 7,065,408 B2 | 6/2006 | Herman et al. |
| 7,081,122 B1 | 7/2006 | Reiley et al. |
| 7,090,672 B2 | 8/2006 | Underwood et al. |
| 7,094,215 B2 | 8/2006 | Davison et al. |
| 7,104,989 B2 | 9/2006 | Skarda |
| 7,118,574 B2 | 10/2006 | Patel et al. |
| 7,131,969 B1 | 11/2006 | Hovda et al. |
| 7,153,307 B2 | 12/2006 | Scribner et al. |
| 7,163,536 B2 | 1/2007 | Godara |
| 7,177,678 B1 | 2/2007 | Osorio et al. |
| 7,179,255 B2 | 2/2007 | Lettice et al. |
| 7,186,234 B2 | 3/2007 | Dahla et al. |
| 7,192,428 B2 | 3/2007 | Eggers et al. |
| 7,201,731 B2 | 4/2007 | Lundquist et al. |
| 7,201,750 B1 | 4/2007 | Eggers et al. |
| 7,211,055 B2 | 5/2007 | Diederich et al. |
| 7,217,268 B2 | 5/2007 | Eggers et al. |
| 7,238,184 B2 | 7/2007 | Megerman et al. |
| 7,241,297 B2 | 7/2007 | Shaolian et al. |
| 7,250,048 B2 | 7/2007 | Francischelli et al. |
| 7,258,690 B2 | 8/2007 | Sutton et al. |

(56) References Cited

U.S. PATENT DOCUMENTS

| | | |
|---|---|---|
| 7,270,659 B2 | 9/2007 | Ricart et al. |
| 7,270,661 B2 | 9/2007 | Dahla et al. |
| 7,276,063 B2 | 10/2007 | Davison et al. |
| 7,294,127 B2 | 11/2007 | Leung et al. |
| 7,305,264 B2 | 12/2007 | Larson et al. |
| 7,306,596 B2 | 12/2007 | Hillier et al. |
| 7,306,598 B2 | 12/2007 | Truckai et al. |
| 7,318,823 B2 | 1/2008 | Sharps et al. |
| 7,318,826 B2 | 1/2008 | Teitelbaum et al. |
| 7,326,203 B2 | 2/2008 | Papineau et al. |
| 7,331,956 B2 | 2/2008 | Hovda et al. |
| 7,331,957 B2 | 2/2008 | Woloszko et al. |
| RE40,156 E | 3/2008 | Sharps et al. |
| 7,346,391 B1 | 3/2008 | Osorio et al. |
| RE40,279 E | 4/2008 | Sluijter et al. |
| 7,386,350 B2 | 6/2008 | Vilims |
| 7,387,625 B2 | 6/2008 | Hovda et al. |
| 7,393,351 B2 | 7/2008 | Woloszko et al. |
| 7,399,306 B2 | 7/2008 | Reiley et al. |
| 7,422,585 B1 | 9/2008 | Eggers et al. |
| 7,429,262 B2 | 9/2008 | Woloszko et al. |
| 7,435,247 B2 | 10/2008 | Woloszko et al. |
| 7,435,250 B2 | 10/2008 | Francischelli et al. |
| 7,442,191 B2 | 10/2008 | Hovda et al. |
| 7,468,059 B2 | 12/2008 | Eggers et al. |
| 7,480,533 B2 | 1/2009 | Cosman et al. |
| 7,502,652 B2 | 3/2009 | Gaunt et al. |
| 7,503,920 B2 | 3/2009 | Siegal |
| 7,503,921 B2 | 3/2009 | Siegal |
| 7,507,236 B2 | 3/2009 | Eggers et al. |
| 7,546,164 B2 | 6/2009 | King |
| 7,553,307 B2 | 6/2009 | Bleich et al. |
| 7,553,309 B2 | 6/2009 | Buysse et al. |
| 7,555,343 B2 | 6/2009 | Bleich |
| 7,559,932 B2 | 7/2009 | Truckai et al. |
| 7,569,626 B2 | 8/2009 | Truckai |
| 7,574,257 B2 | 8/2009 | Rittman, III |
| 7,585,300 B2 | 9/2009 | Cha |
| 7,593,778 B2 | 9/2009 | Chandran et al. |
| 7,594,913 B2 | 9/2009 | Ormsby et al. |
| 7,604,636 B1 | 10/2009 | Walters et al. |
| 7,621,952 B2 | 11/2009 | Truckai et al. |
| 7,645,277 B2 | 1/2010 | McClurken et al. |
| 7,678,111 B2 | 3/2010 | Mulier et al. |
| 7,678,116 B2 | 3/2010 | Truckai et al. |
| 7,682,378 B2 | 3/2010 | Truckal et al. |
| 7,708,733 B2 | 5/2010 | Sanders et al. |
| 7,722,620 B2 | 5/2010 | Truckai et al. |
| 7,731,720 B2 | 6/2010 | Sand et al. |
| 7,738,968 B2 | 6/2010 | Bleich |
| 7,740,631 B2 | 6/2010 | Bleich et al. |
| 7,749,218 B2 | 7/2010 | Pellegrino et al. |
| 7,749,220 B2 | 7/2010 | Schmaltz et al. |
| 7,780,733 B2 | 8/2010 | Carver et al. |
| 7,792,588 B2 | 9/2010 | Harding |
| 7,799,021 B2 | 9/2010 | Leung et al. |
| 7,819,826 B2 | 10/2010 | Diederich et al. |
| 7,819,869 B2 | 10/2010 | Godara et al. |
| 7,824,398 B2 | 11/2010 | Woloszko et al. |
| 7,824,404 B2 | 11/2010 | Godara et al. |
| 7,828,804 B2 | 11/2010 | Li et al. |
| 7,846,156 B2 | 12/2010 | Malis et al. |
| 7,850,685 B2 | 12/2010 | Kunis et al. |
| 7,853,326 B2 | 12/2010 | Rittman, III |
| 7,857,813 B2 | 12/2010 | Schmitz et al. |
| 7,879,032 B1 | 2/2011 | Garito et al. |
| 7,887,543 B2 | 2/2011 | Sand et al. |
| 7,892,235 B2 | 2/2011 | Ellis |
| 7,896,870 B2 | 3/2011 | Arless et al. |
| 7,896,909 B2 | 3/2011 | Sharkey et al. |
| 7,901,403 B2 | 3/2011 | Woloszko et al. |
| 7,909,827 B2 | 3/2011 | Reiley et al. |
| 7,909,873 B2 | 3/2011 | Tan-Malecki et al. |
| 7,914,526 B2 | 3/2011 | Lehmann et al. |
| 7,914,535 B2 | 3/2011 | Assell et al. |
| 7,917,222 B1 | 3/2011 | Osorio et al. |
| 7,918,849 B2 | 4/2011 | Bleich et al. |
| 7,918,874 B2 | 4/2011 | Siegal |
| 7,938,835 B2 | 5/2011 | Boucher et al. |
| 7,945,331 B2 | 5/2011 | Vilims |
| 7,951,140 B2 | 5/2011 | Arless et al. |
| 7,959,634 B2 | 6/2011 | Sennett |
| 7,963,915 B2 | 6/2011 | Bleich |
| 7,967,827 B2 | 6/2011 | Osorio et al. |
| 7,969,634 B2 | 6/2011 | Watanabe et al. |
| 7,972,340 B2 | 7/2011 | Sand et al. |
| 8,000,785 B2 | 8/2011 | Ritmann, III |
| 8,021,401 B2 | 9/2011 | Carl et al. |
| 8,025,688 B2 | 9/2011 | Diederich et al. |
| 8,034,052 B2 | 10/2011 | Podhajsky |
| 8,034,071 B2 | 10/2011 | Scribner et al. |
| 8,043,287 B2 | 10/2011 | Conquergood et al. |
| 8,048,030 B2 | 11/2011 | McGuckin, Jr. et al. |
| 8,048,071 B2 | 11/2011 | Youssef et al. |
| 8,048,083 B2 | 11/2011 | Shadduck et al. |
| 8,052,661 B2 | 11/2011 | McGuckin, Jr. et al. |
| 8,062,290 B2 | 11/2011 | Buysse et al. |
| 8,066,702 B2 | 11/2011 | Rittman, III et al. |
| 8,066,712 B2 | 11/2011 | Truckai et al. |
| 8,070,753 B2 | 12/2011 | Truckai et al. |
| 8,082,043 B2 | 12/2011 | Sharkey et al. |
| 8,083,736 B2 | 12/2011 | McClurken et al. |
| 8,096,957 B2 | 1/2012 | Conquergood et al. |
| 8,100,896 B2 | 1/2012 | Podhajsky |
| 8,109,933 B2 | 2/2012 | Truckai et al. |
| 8,123,750 B2 | 2/2012 | Norton et al. |
| 8,123,756 B2 | 2/2012 | Miller et al. |
| 8,128,619 B2 | 3/2012 | Sharkey et al. |
| 8,128,633 B2 | 3/2012 | Linderman et al. |
| 8,162,933 B2 | 4/2012 | Francischelli et al. |
| 8,163,031 B2 | 4/2012 | Truckai et al. |
| 8,172,846 B2 | 5/2012 | Brunnett et al. |
| 8,182,477 B2 | 5/2012 | Orszulak et al. |
| 8,187,312 B2 | 5/2012 | Sharkey et al. |
| 8,192,424 B2 | 6/2012 | Woloszko et al. |
| 8,192,435 B2 | 6/2012 | Bleich et al. |
| 8,216,223 B2 | 7/2012 | Wham et al. |
| 8,226,697 B2 | 7/2012 | Sharkey et al. |
| 8,231,616 B2 | 7/2012 | McPherson et al. |
| 8,241,335 B2 | 8/2012 | Truckai et al. |
| 8,246,627 B2 | 8/2012 | Vanleeuwen et al. |
| 8,265,747 B2 | 9/2012 | Rittman, III et al. |
| 8,282,628 B2 | 10/2012 | Paul et al. |
| 8,292,882 B2 | 10/2012 | Danek et al. |
| 8,292,887 B2 | 10/2012 | Woloszko et al. |
| 8,323,277 B2 | 12/2012 | Vilims |
| 8,323,279 B2 | 12/2012 | Dahla et al. |
| 8,343,146 B2 | 1/2013 | Godara et al. |
| 8,348,946 B2 | 1/2013 | McClurken et al. |
| 8,348,955 B2 | 1/2013 | Truckai et al. |
| 8,355,791 B2 | 1/2013 | Moffitt |
| 8,355,799 B2 | 1/2013 | Marion et al. |
| 8,361,063 B2 | 1/2013 | Godara |
| 8,361,067 B2 | 1/2013 | Pellegrino et al. |
| 8,406,886 B2 | 3/2013 | Gaunt et al. |
| 8,409,289 B2 | 4/2013 | Truckai et al. |
| 8,414,509 B2 | 4/2013 | Diederich et al. |
| 8,414,571 B2 | 4/2013 | Pellegrino et al. |
| 8,419,730 B2 | 4/2013 | Pellegrino et al. |
| 8,419,731 B2 | 4/2013 | Pellegrino et al. |
| 8,425,507 B2 | 4/2013 | Pellegrino et al. |
| 8,430,887 B2 | 4/2013 | Truckai et al. |
| 8,444,636 B2 | 5/2013 | Shadduck et al. |
| 8,444,640 B2 | 5/2013 | Demarais et al. |
| 8,454,594 B2 | 6/2013 | Demarais et al. |
| 8,460,382 B2 | 6/2013 | Helm et al. |
| 8,475,449 B2 | 7/2013 | Werneth et al. |
| 8,486,063 B2 | 7/2013 | Werneth et al. |
| 8,487,021 B2 | 7/2013 | Truckai et al. |
| 8,504,147 B2 | 8/2013 | Deem et al. |
| 8,505,545 B2 | 8/2013 | Conquergood et al. |
| 8,518,036 B2 | 8/2013 | Leung et al. |
| 8,523,871 B2 | 9/2013 | Truckai et al. |
| 8,535,309 B2 | 9/2013 | Pellegrino et al. |

(56) References Cited

U.S. PATENT DOCUMENTS

| | | |
|---|---|---|
| 8,535,809 B2 | 9/2013 | Komurasaki et al. |
| 8,540,723 B2 | 9/2013 | Shadduck et al. |
| 8,556,910 B2 | 10/2013 | Truckai et al. |
| 8,556,911 B2 | 10/2013 | Mehta et al. |
| 8,560,062 B2 | 10/2013 | Rittman, III et al. |
| 8,562,598 B2 | 10/2013 | Falkenstein et al. |
| 8,562,607 B2 | 10/2013 | Truckai et al. |
| 8,562,620 B2 | 10/2013 | Truckai et al. |
| 8,579,903 B2 | 11/2013 | Carl |
| 8,585,694 B2 | 11/2013 | Amoah et al. |
| 8,591,507 B2 | 11/2013 | Kramer et al. |
| 8,597,301 B2 | 12/2013 | Mitchell |
| 8,603,088 B2 | 12/2013 | Stem et al. |
| 8,613,744 B2 | 12/2013 | Pellegrino et al. |
| 8,617,156 B2 | 12/2013 | Werneth et al. |
| 8,623,014 B2 | 1/2014 | Pellegrino et al. |
| 8,623,025 B2 | 1/2014 | Tan-Malecki et al. |
| 8,628,528 B2 | 1/2014 | Pellegrino et al. |
| 8,636,736 B2 | 1/2014 | Yates et al. |
| 8,644,941 B2 | 2/2014 | Rooney et al. |
| 8,657,814 B2 | 2/2014 | Werneth et al. |
| 8,663,266 B1 | 3/2014 | Obsuth |
| 8,672,934 B2 | 3/2014 | Benamou et al. |
| 8,676,309 B2 | 3/2014 | Deem et al. |
| 8,679,023 B2 | 3/2014 | Kobayashi et al. |
| RE44,833 E | 4/2014 | Muir et al. |
| 8,690,884 B2 | 4/2014 | Linderman et al. |
| 8,696,679 B2 | 4/2014 | Shadduck et al. |
| RE44,883 E | 5/2014 | Cha |
| 8,740,897 B2 | 6/2014 | Leung et al. |
| 8,747,359 B2 | 6/2014 | Pakter et al. |
| 8,747,398 B2 | 6/2014 | Behnke |
| 8,758,349 B2 | 6/2014 | Germain et al. |
| 8,764,761 B2 | 7/2014 | Truckai et al. |
| 8,771,265 B2 | 7/2014 | Truckai |
| 8,771,276 B2 | 7/2014 | Linderman |
| 8,774,913 B2 | 7/2014 | Demarais et al. |
| 8,774,924 B2 | 7/2014 | Weiner |
| 8,777,479 B2 | 7/2014 | Kwan et al. |
| 8,784,411 B2 | 7/2014 | Leuthardt et al. |
| 8,795,270 B2 | 8/2014 | Drake |
| 8,808,161 B2 | 8/2014 | Gregg et al. |
| 8,808,284 B2 | 8/2014 | Pellegrino et al. |
| 8,814,873 B2 | 8/2014 | Schaller et al. |
| 8,818,503 B2 | 8/2014 | Rittman, III |
| 8,821,488 B2 | 9/2014 | Stewart et al. |
| 8,845,631 B2 | 9/2014 | Werneth et al. |
| 8,864,759 B2 | 10/2014 | Godara et al. |
| 8,864,760 B2 | 10/2014 | Kramer et al. |
| 8,864,777 B2 | 10/2014 | Harrison et al. |
| 8,882,755 B2 | 11/2014 | Leung et al. |
| 8,882,759 B2 | 11/2014 | Manley et al. |
| 8,882,764 B2 | 11/2014 | Sutton et al. |
| 8,894,658 B2 | 11/2014 | Linderman et al. |
| 8,911,497 B2 | 12/2014 | Chavatte et al. |
| 8,915,949 B2 | 12/2014 | Diederich et al. |
| 8,926,620 B2 | 1/2015 | Chasmawala et al. |
| 8,932,300 B2 | 1/2015 | Shadduck et al. |
| 8,939,969 B2 | 1/2015 | Temelli et al. |
| 8,951,949 B2 | 2/2015 | Lee et al. |
| 8,968,288 B2 | 3/2015 | Brannan |
| 8,989,859 B2 | 3/2015 | Deem et al. |
| 8,992,522 B2 | 3/2015 | Pellegrino et al. |
| 8,992,523 B2 | 3/2015 | Pellegrino et al. |
| 9,005,210 B2 | 4/2015 | Truckai et al. |
| 9,008,793 B1 | 4/2015 | Cosman, Sr. et al. |
| 9,017,325 B2 | 4/2015 | Pellegrino et al. |
| 9,023,038 B2 | 5/2015 | Pellegrino et al. |
| 9,028,488 B2 | 5/2015 | Goshayeshgar |
| 9,028,538 B2 | 5/2015 | Paul et al. |
| 9,039,701 B2 | 5/2015 | Pellegrino et al. |
| 9,044,245 B2 | 6/2015 | Condie et al. |
| 9,044,254 B2 | 6/2015 | Ladtkow et al. |
| 9,044,575 B2 | 6/2015 | Beasley et al. |
| 9,066,769 B2 | 6/2015 | Truckai et al. |
| 9,078,761 B2 | 7/2015 | Godara et al. |
| 9,095,359 B2 | 8/2015 | Robert et al. |
| 9,113,896 B2 | 8/2015 | Mulier et al. |
| 9,113,911 B2 | 8/2015 | Sherman |
| 9,113,925 B2 | 8/2015 | Smith et al. |
| 9,113,950 B2 | 8/2015 | Schutlz et al. |
| 9,113,974 B2 | 8/2015 | Germain |
| 9,119,639 B2 | 9/2015 | Kuntz |
| 9,119,647 B2 | 9/2015 | Brannan |
| 9,119,650 B2 | 9/2015 | Brannan et al. |
| 9,125,671 B2 | 9/2015 | Germain et al. |
| 9,130,416 B2 | 9/2015 | Baba et al. |
| 9,131,597 B2 | 9/2015 | Taft et al. |
| 9,149,652 B2 | 10/2015 | Wenz et al. |
| 9,151,680 B2 | 10/2015 | Brannan |
| 9,155,895 B2 | 10/2015 | Wacnik et al. |
| 9,161,614 B2 | 10/2015 | Limongi et al. |
| 9,161,735 B2 | 10/2015 | Bradford et al. |
| 9,161,797 B2 | 10/2015 | Truckai et al. |
| 9,161,798 B2 | 10/2015 | Truckai et al. |
| 9,161,805 B2 | 10/2015 | Isenberg |
| 9,161,809 B2 | 10/2015 | Germain et al. |
| 9,161,814 B2 | 10/2015 | Brannan et al. |
| 9,168,054 B2 | 10/2015 | Turner et al. |
| 9,168,078 B2 | 10/2015 | Linderman et al. |
| 9,168,085 B2 | 10/2015 | Juzkiw |
| 9,173,676 B2 | 11/2015 | Pellegrino et al. |
| 9,173,700 B2 | 11/2015 | Godara et al. |
| 9,179,970 B2 | 11/2015 | Utley et al. |
| 9,179,972 B2 | 11/2015 | Olson |
| 9,180,416 B2 | 11/2015 | Phan et al. |
| 9,186,197 B2 | 11/2015 | McKay |
| 9,192,308 B2 | 11/2015 | Brannan et al. |
| 9,192,397 B2 | 11/2015 | Sennett et al. |
| 9,198,684 B2 | 12/2015 | Arthur et al. |
| 9,216,053 B2 | 12/2015 | Godara et al. |
| 9,226,756 B2 | 1/2016 | Teisen et al. |
| 9,232,954 B2 | 1/2016 | Steiner et al. |
| 9,237,916 B2 | 1/2016 | Crainich et al. |
| 9,238,139 B2 | 1/2016 | Degiorgio et al. |
| 9,241,057 B2 | 1/2016 | Van Wyk et al. |
| 9,241,729 B2 | 1/2016 | Juntz et al. |
| 9,241,760 B2 | 1/2016 | Godara et al. |
| 9,247,970 B2 | 2/2016 | Teisen |
| 9,247,992 B2 | 2/2016 | Ladtkow et al. |
| 9,247,993 B2 | 2/2016 | Ladtkow et al. |
| 9,248,278 B2 | 2/2016 | Crosby et al. |
| 9,248,289 B2 | 2/2016 | Bennett et al. |
| 9,254,168 B2 | 2/2016 | Palanker |
| 9,254,386 B2 | 2/2016 | Lee et al. |
| 9,259,241 B2 | 2/2016 | Pellegrino et al. |
| 9,259,248 B2 | 2/2016 | Leuthardt et al. |
| 9,259,269 B2 | 2/2016 | Ladtkow et al. |
| 9,259,569 B2 | 2/2016 | Brounstein et al. |
| 9,259,577 B2 | 2/2016 | Kaula et al. |
| 9,265,522 B2 | 2/2016 | Pellegrino et al. |
| 9,265,557 B2 | 2/2016 | Sherman et al. |
| 9,277,969 B2 | 3/2016 | Brannan et al. |
| 9,282,979 B2 | 3/2016 | O'Neil et al. |
| 9,282,988 B2 | 3/2016 | Goshayeshgar |
| 9,283,015 B2 | 3/2016 | Tan-Malecki et al. |
| 9,289,607 B2 | 3/2016 | Su et al. |
| 9,295,517 B2 | 3/2016 | Peyman et al. |
| 9,295,841 B2 | 3/2016 | Fang et al. |
| 9,301,723 B2 | 4/2016 | Brannan et al. |
| 9,301,804 B2 | 4/2016 | Bonn |
| 9,302,117 B2 | 4/2016 | De Vincentiis |
| 9,308,036 B2 | 4/2016 | Robinson |
| 9,308,045 B2 | 4/2016 | Kim et al. |
| 9,314,252 B2 | 4/2016 | Schaller et al. |
| 9,314,613 B2 | 4/2016 | Mashiach |
| 9,314,618 B2 | 4/2016 | Imran et al. |
| 9,333,033 B2 | 5/2016 | Gliner |
| 9,333,144 B2 | 5/2016 | Baxter et al. |
| 9,333,339 B2 | 5/2016 | Weiner |
| 9,333,361 B2 | 5/2016 | Li et al. |
| 9,333,373 B2 | 5/2016 | Imran |
| 9,339,655 B2 | 5/2016 | Carbunaru |
| 9,345,530 B2 | 5/2016 | Ballakur et al. |

(56) References Cited

U.S. PATENT DOCUMENTS

| | | |
|---|---|---|
| 9,345,537 B2 | 5/2016 | Harrison et al. |
| 9,345,538 B2 | 5/2016 | Deem et al. |
| 9,351,739 B2 | 5/2016 | Mahoney et al. |
| 9,353,396 B2 | 5/2016 | Demirev et al. |
| 9,358,059 B2 | 6/2016 | Linderman et al. |
| 9,358,067 B2 | 6/2016 | Lee et al. |
| 9,358,396 B2 | 6/2016 | Holley |
| 9,364,242 B2 | 6/2016 | Tornier et al. |
| 9,364,286 B2 | 6/2016 | Werneth et al. |
| 9,370,348 B2 | 6/2016 | Tally et al. |
| 9,370,392 B2 | 6/2016 | Sharonov |
| 9,370,398 B2 | 6/2016 | Ladtkow et al. |
| 9,375,274 B2 | 6/2016 | Reid |
| 9,375,275 B2 | 6/2016 | Lee et al. |
| 9,375,278 B2 | 6/2016 | Robert et al. |
| 9,375,279 B2 | 6/2016 | Brannan |
| 9,375,283 B2 | 6/2016 | Arts et al. |
| 9,381,024 B2 | 7/2016 | Globerman et al. |
| 9,381,045 B2 | 7/2016 | Donner et al. |
| 9,381,050 B2 | 7/2016 | Lee et al. |
| 9,381,359 B2 | 7/2016 | Parramon et al. |
| 9,387,094 B2 | 7/2016 | Manrique et al. |
| 9,393,416 B2 | 7/2016 | Rooney et al. |
| 9,398,931 B2 | 7/2016 | Wittenberger et al. |
| 9,399,144 B2 | 7/2016 | Howard |
| 9,403,038 B2 | 8/2016 | Tyler |
| 9,409,023 B2 | 8/2016 | Burdick et al. |
| 9,414,884 B2 | 8/2016 | Faehndrich et al. |
| 9,421,064 B2 | 8/2016 | Pellegrino et al. |
| 9,421,123 B2 | 8/2016 | Lee et al. |
| 9,421,371 B2 | 8/2016 | Pless et al. |
| 9,421,378 B2 | 8/2016 | Lian et al. |
| 9,436,447 B2 | 9/2016 | Kong et al. |
| 9,439,693 B2 | 9/2016 | Childs et al. |
| 9,439,721 B2 | 9/2016 | Werneth et al. |
| 9,445,859 B2 | 9/2016 | Pageard |
| 9,446,229 B2 | 9/2016 | Omar-Pasha |
| 9,446,235 B2 | 9/2016 | Su et al. |
| 9,452,286 B2 | 9/2016 | Cowan et al. |
| 9,456,836 B2 | 10/2016 | Boling et al. |
| 9,457,182 B2 | 10/2016 | Koop |
| 9,468,485 B2 | 10/2016 | Wittenberger et al. |
| 9,468,495 B2 | 10/2016 | Kunis et al. |
| 9,474,565 B2 | 10/2016 | Shikhman et al. |
| 9,474,906 B2 | 10/2016 | Sachs et al. |
| 9,480,485 B2 | 11/2016 | Aho et al. |
| 9,486,279 B2 | 11/2016 | Pellegrino et al. |
| 9,486,447 B2 | 11/2016 | Peterson et al. |
| 9,486,621 B2 | 11/2016 | Howard et al. |
| 9,492,657 B2 | 11/2016 | Gerber |
| 9,492,664 B2 | 11/2016 | Peterson |
| 9,504,372 B2 | 11/2016 | Kim |
| 9,504,481 B2 | 11/2016 | Germain et al. |
| 9,504,506 B2 | 11/2016 | Crainich et al. |
| 9,504,518 B2 | 11/2016 | Condie et al. |
| 9,504,530 B2 | 11/2016 | Hartmann et al. |
| 9,504,818 B2 | 11/2016 | Moffitt et al. |
| 9,511,229 B2 | 12/2016 | Bradley |
| 9,511,231 B1 | 12/2016 | Kent et al. |
| 9,513,761 B2 | 12/2016 | Shikhman et al. |
| 9,517,077 B2 | 12/2016 | Blain et al. |
| 9,517,200 B2 | 12/2016 | Bleier |
| 9,526,507 B2 | 12/2016 | Germain |
| 9,526,551 B2 | 12/2016 | Linderman |
| 9,526,559 B2 | 12/2016 | Banamou et al. |
| 9,532,828 B2 | 1/2017 | Condie et al. |
| 9,549,772 B2 | 1/2017 | Carl |
| 9,550,014 B2 | 1/2017 | Norred et al. |
| 9,550,041 B2 | 1/2017 | Bedell |
| 9,555,037 B2 | 1/2017 | Podhajsky |
| 9,556,101 B2 | 1/2017 | Robertson et al. |
| 9,556,449 B2 | 1/2017 | Basu et al. |
| 9,566,449 B2 | 2/2017 | Perryman et al. |
| 9,572,976 B2 | 2/2017 | Howard et al. |
| 9,572,986 B2 | 2/2017 | Moffitt |
| 9,579,127 B2 | 2/2017 | Kostuik et al. |
| 9,579,518 B2 | 2/2017 | Gertner |
| 9,597,091 B2 | 3/2017 | Bromer |
| 9,597,148 B2 | 3/2017 | Olson |
| RE46,356 E | 4/2017 | Pellegrino et al. |
| 9,610,083 B2 | 4/2017 | Kuntz |
| 9,610,117 B2 | 4/2017 | Germain |
| 9,636,175 B2 | 5/2017 | Stern et al. |
| 9,642,629 B2 | 5/2017 | Griffiths et al. |
| 9,649,116 B2 | 5/2017 | Germain |
| 9,681,889 B1 | 6/2017 | Greenhalgh et al. |
| 9,687,255 B2 | 6/2017 | Sennett et al. |
| 9,724,107 B2 | 8/2017 | Pellegrino et al. |
| 9,724,151 B2 | 8/2017 | Edidin |
| 9,730,707 B2 | 8/2017 | Sasaki et al. |
| 9,743,854 B2 | 8/2017 | Stewart et al. |
| 9,743,938 B2 | 8/2017 | Germain et al. |
| 9,750,560 B2 | 9/2017 | Ballakur et al. |
| 9,757,193 B2 | 9/2017 | Zarins et al. |
| 9,770,280 B2 | 9/2017 | Diederich et al. |
| 9,775,627 B2 | 10/2017 | Patel et al. |
| 9,782,221 B2 | 10/2017 | Srinivasan |
| 9,795,802 B2 | 10/2017 | Mohamed et al. |
| 9,814,514 B2 | 11/2017 | Shelton, IV et al. |
| 9,844,406 B2 | 12/2017 | Edwards et al. |
| 9,848,944 B2 | 12/2017 | Sutton et al. |
| 9,872,687 B2 | 1/2018 | Tornier et al. |
| 9,872,691 B2 | 1/2018 | Griffiths et al. |
| 9,877,707 B2 | 1/2018 | Godara et al. |
| 9,878,944 B1 | 1/2018 | Dai et al. |
| 9,913,675 B2 | 3/2018 | Germain |
| 10,028,753 B2 | 7/2018 | Pellegrino et al. |
| 10,028,784 B2 | 7/2018 | Kramer et al. |
| 10,052,152 B2 | 8/2018 | Tegg et al. |
| 10,111,674 B2 | 10/2018 | Crainich et al. |
| 10,111,704 B2 | 10/2018 | Pellegrino et al. |
| 10,123,809 B2 | 11/2018 | Germain |
| 10,245,092 B2 | 4/2019 | Germain |
| 10,265,099 B2 | 4/2019 | Pellegrino et al. |
| 10,272,271 B2 | 4/2019 | Diederich et al. |
| 10,272,721 B2 | 4/2019 | Diederich et al. |
| 10,292,716 B2 | 5/2019 | Aho et al. |
| 10,292,719 B2 | 5/2019 | Burger et al. |
| 10,299,805 B2 | 5/2019 | Germain et al. |
| 10,327,841 B2 | 6/2019 | Germain |
| 10,357,258 B2 | 7/2019 | Patel et al. |
| 10,383,641 B2 | 8/2019 | LeRoy et al. |
| 10,390,877 B2 | 8/2019 | Heggeness et al. |
| 10,441,295 B2 | 10/2019 | Brockman et al. |
| 10,448,995 B2 | 10/2019 | Olson |
| 10,456,187 B2 | 10/2019 | Edidin |
| 10,463,380 B2 | 11/2019 | Purdy et al. |
| 10,463,423 B2 | 11/2019 | Sutton et al. |
| 10,470,781 B2 | 11/2019 | Purdy et al. |
| 10,478,241 B2 | 11/2019 | Purdy et al. |
| 10,478,246 B2 | 11/2019 | Pellegrino et al. |
| 10,493,247 B2 | 12/2019 | Goshayeshgar |
| 10,499,960 B2 | 12/2019 | Sinnott et al. |
| 10,517,611 B2 | 12/2019 | Patel et al. |
| 10,524,805 B2 | 1/2020 | Zilberman et al. |
| 10,571,611 B2 | 2/2020 | Koenig et al. |
| 10,588,691 B2 | 3/2020 | Pellegino et al. |
| 10,589,131 B2 | 3/2020 | Diederich et al. |
| 10,603,522 B2 | 3/2020 | Diederich et al. |
| 10,624,652 B2 | 4/2020 | Germain et al. |
| 10,660,656 B2 | 5/2020 | Purdy et al. |
| 10,898,254 B2 | 1/2021 | Diederich et al. |
| 10,905,440 B2 | 2/2021 | Pellegrino et al. |
| RE48,460 E | 3/2021 | Pellegrino et al. |
| 11,007,010 B2 | 5/2021 | Donovan et al. |
| 11,026,734 B2 | 6/2021 | Truckai et al. |
| 11,026,744 B2 | 6/2021 | Purdy et al. |
| 11,052,267 B2 | 7/2021 | Diederich et al. |
| 11,065,046 B2 | 7/2021 | Edidin |
| 11,123,103 B2 | 9/2021 | Donovan et al. |
| 11,160,563 B2 | 11/2021 | Patel et al. |
| 11,207,100 B2 | 12/2021 | Donovan et al. |
| 11,234,764 B1 | 2/2022 | Patel et al. |
| 11,291,502 B2 | 4/2022 | Patel et al. |

(56) References Cited

U.S. PATENT DOCUMENTS

| | | |
|---|---|---|
| 11,426,199 B2 | 8/2022 | Donovan et al. |
| 11,471,171 B2 | 10/2022 | Pellegrino et al. |
| 11,471,210 B2 | 10/2022 | Pellegrino et al. |
| 11,596,468 B2 | 3/2023 | Pellegrino et al. |
| 2001/0001314 A1 | 5/2001 | Davison et al. |
| 2001/0001811 A1 | 5/2001 | Burney et al. |
| 2001/0020167 A1 | 9/2001 | Woloszko et al. |
| 2001/0023348 A1 | 9/2001 | Ashley et al. |
| 2001/0025176 A1 | 9/2001 | Ellsberry et al. |
| 2001/0025177 A1 | 9/2001 | Woloszko et al. |
| 2001/0027295 A1 | 10/2001 | Dulak et al. |
| 2001/0029370 A1 | 10/2001 | Hodva et al. |
| 2001/0029373 A1 | 10/2001 | Baker et al. |
| 2001/0029393 A1 | 10/2001 | Tierney et al. |
| 2001/0032001 A1 | 10/2001 | Ricart et al. |
| 2001/0047167 A1 | 11/2001 | Heggeness |
| 2001/0049522 A1 | 12/2001 | Eggers et al. |
| 2001/0049527 A1 | 12/2001 | Cragg |
| 2001/0051802 A1 | 12/2001 | Woloszko et al. |
| 2001/0053885 A1 | 12/2001 | Gielen et al. |
| 2001/0056280 A1 | 12/2001 | Underwood et al. |
| 2002/0016583 A1 | 2/2002 | Cragg |
| 2002/0016600 A1 | 2/2002 | Cosman |
| 2002/0019626 A1 | 2/2002 | Sharkey et al. |
| 2002/0026186 A1 | 2/2002 | Woloszko et al. |
| 2002/0049438 A1 | 4/2002 | Sharkey et al. |
| 2002/0052600 A1 | 5/2002 | Davison et al. |
| 2002/0068930 A1 | 6/2002 | Tasto et al. |
| 2002/0095144 A1 | 7/2002 | Carl |
| 2002/0095151 A1 | 7/2002 | Dahla et al. |
| 2002/0095152 A1 | 7/2002 | Ciarrocca et al. |
| 2002/0099366 A1 | 7/2002 | Dahla et al. |
| 2002/0111661 A1 | 8/2002 | Cross et al. |
| 2002/0115945 A1 | 8/2002 | D'Luzansky et al. |
| 2002/0120259 A1 | 8/2002 | Lettice et al. |
| 2002/0133148 A1* | 9/2002 | Daniel ............ A61B 18/1477 606/34 |
| 2002/0147444 A1 | 10/2002 | Shah et al. |
| 2002/0151885 A1 | 10/2002 | Underwood et al. |
| 2002/0165532 A1 | 11/2002 | Hill et al. |
| 2002/0183758 A1 | 12/2002 | Middleton et al. |
| 2002/0188284 A1 | 12/2002 | To et al. |
| 2002/0188290 A1 | 12/2002 | Sharkey et al. |
| 2002/0193708 A1 | 12/2002 | Thompson et al. |
| 2002/0193789 A1 | 12/2002 | Underwood et al. |
| 2003/0009164 A1 | 1/2003 | Woloszko et al. |
| 2003/0014047 A1 | 1/2003 | Woloszko et al. |
| 2003/0014088 A1 | 1/2003 | Fang et al. |
| 2003/0028147 A1 | 2/2003 | Aves et al. |
| 2003/0028189 A1 | 2/2003 | Woloszko et al. |
| 2003/0032929 A1* | 2/2003 | McGuckin, Jr. .. A61M 25/0041 604/272 |
| 2003/0040742 A1 | 2/2003 | Underwood et al. |
| 2003/0040743 A1 | 2/2003 | Cosman et al. |
| 2003/0055418 A1 | 3/2003 | Tasto et al. |
| 2003/0069569 A1 | 4/2003 | Burdette et al. |
| 2003/0083592 A1 | 5/2003 | Faciszewski |
| 2003/0084907 A1 | 5/2003 | Pacek et al. |
| 2003/0097126 A1 | 5/2003 | Woloszko et al. |
| 2003/0097129 A1 | 5/2003 | Davison et al. |
| 2003/0130655 A1 | 7/2003 | Woloszko et al. |
| 2003/0139652 A1 | 7/2003 | Kang et al. |
| 2003/0158545 A1 | 8/2003 | Hovda et al. |
| 2003/0181963 A1* | 9/2003 | Pellegrino ............ A61N 7/02 601/2 |
| 2003/0208194 A1 | 11/2003 | Hovda et al. |
| 2003/0216725 A1 | 11/2003 | Woloszko et al. |
| 2003/0216726 A1 | 11/2003 | Eggers et al. |
| 2003/0225364 A1 | 12/2003 | Kraft |
| 2004/0006339 A1 | 1/2004 | Underwood et al. |
| 2004/0015163 A1 | 1/2004 | Buysse et al. |
| 2004/0024399 A1 | 2/2004 | Sharps et al. |
| 2004/0054366 A1 | 3/2004 | Davison et al. |
| 2004/0064023 A1 | 4/2004 | Thomas et al. |
| 2004/0064136 A1 | 4/2004 | Crombie et al. |
| 2004/0064137 A1 | 4/2004 | Pellegrino et al. |
| 2004/0068242 A1 | 4/2004 | McGuckin |
| 2004/0082942 A1 | 4/2004 | Katzman |
| 2004/0082946 A1 | 4/2004 | Malis et al. |
| 2004/0087937 A1 | 5/2004 | Eggers et al. |
| 2004/0111087 A1 | 6/2004 | Stern et al. |
| 2004/0116922 A1 | 6/2004 | Hovda et al. |
| 2004/0120668 A1 | 6/2004 | Loeb |
| 2004/0120891 A1 | 6/2004 | Hill et al. |
| 2004/0133124 A1 | 7/2004 | Bates et al. |
| 2004/0162559 A1* | 8/2004 | Arramon ............ A61B 17/3417 606/62 |
| 2004/0186544 A1 | 9/2004 | King |
| 2004/0193151 A1 | 9/2004 | To et al. |
| 2004/0193152 A1 | 9/2004 | Sutton et al. |
| 2004/0220577 A1 | 11/2004 | Cragg et al. |
| 2004/0225228 A1 | 11/2004 | Ferree |
| 2004/0230190 A1 | 11/2004 | Dahla et al. |
| 2004/0267269 A1 | 12/2004 | Middleton et al. |
| 2005/0004634 A1 | 1/2005 | Ricart et al. |
| 2005/0010095 A1 | 1/2005 | Stewart et al. |
| 2005/0010203 A1 | 1/2005 | Edwards et al. |
| 2005/0010205 A1 | 1/2005 | Hovda et al. |
| 2005/0043737 A1 | 2/2005 | Reiley et al. |
| 2005/0055096 A1 | 3/2005 | Serhan et al. |
| 2005/0124989 A1 | 6/2005 | Suddaby |
| 2005/0177209 A1 | 8/2005 | Leung et al. |
| 2005/0177210 A1 | 8/2005 | Leung et al. |
| 2005/0177211 A1 | 8/2005 | Leung et al. |
| 2005/0182417 A1 | 8/2005 | Pagano |
| 2005/0192564 A1 | 9/2005 | Cosman et al. |
| 2005/0209610 A1 | 9/2005 | Carrison |
| 2005/0209659 A1 | 9/2005 | Pellegrino et al. |
| 2005/0216018 A1 | 9/2005 | Sennett |
| 2005/0234445 A1 | 10/2005 | Conquergood et al. |
| 2005/0261754 A1 | 11/2005 | Woloszko |
| 2005/0267552 A1 | 12/2005 | Conquergood et al. |
| 2005/0278007 A1 | 12/2005 | Godara |
| 2005/0283148 A1 | 12/2005 | Janssen et al. |
| 2006/0004369 A1 | 1/2006 | Patel et al. |
| 2006/0036264 A1 | 2/2006 | Selover et al. |
| 2006/0052743 A1 | 3/2006 | Reynolds |
| 2006/0064101 A1* | 3/2006 | Arramon .......... A61B 17/32002 606/82 |
| 2006/0079905 A1* | 4/2006 | Beyar ................ A61B 17/8805 606/76 |
| 2006/0095026 A1 | 5/2006 | Ricart et al. |
| 2006/0095028 A1 | 5/2006 | Bleich |
| 2006/0106375 A1 | 5/2006 | Werneth et al. |
| 2006/0106376 A1 | 5/2006 | Godara et al. |
| 2006/0122458 A1 | 6/2006 | Bleich |
| 2006/0129101 A1 | 6/2006 | McGuckin |
| 2006/0178670 A1 | 8/2006 | Woloszko et al. |
| 2006/0200121 A1 | 9/2006 | Mowery |
| 2006/0206128 A1 | 9/2006 | Conquergood et al. |
| 2006/0206129 A1 | 9/2006 | Conquergood et al. |
| 2006/0206130 A1 | 9/2006 | Conquergood et al. |
| 2006/0206132 A1 | 9/2006 | Conquergood et al. |
| 2006/0206133 A1 | 9/2006 | Conquergood et al. |
| 2006/0206134 A1 | 9/2006 | Conquergood et al. |
| 2006/0206166 A1 | 9/2006 | Weiner |
| 2006/0217736 A1 | 9/2006 | Kaneko et al. |
| 2006/0229625 A1 | 10/2006 | Truckai et al. |
| 2006/0237649 A1 | 10/2006 | Gates et al. |
| 2006/0247746 A1 | 11/2006 | Danek et al. |
| 2006/0253117 A1 | 11/2006 | Hovda et al. |
| 2006/0259026 A1 | 11/2006 | Godara et al. |
| 2006/0264957 A1 | 11/2006 | Cragg et al. |
| 2006/0264965 A1 | 11/2006 | Shadduck et al. |
| 2006/0265014 A1 | 11/2006 | Demarais et al. |
| 2006/0276749 A1 | 12/2006 | Selmon et al. |
| 2006/0287649 A1 | 12/2006 | Ormsby et al. |
| 2007/0012803 A1 | 1/2007 | Shimizu et al. |
| 2007/0021803 A1 | 1/2007 | Deem et al. |
| 2007/0027449 A1 | 2/2007 | Godara et al. |
| 2007/0055316 A1 | 3/2007 | Godara et al. |
| 2007/0066987 A1 | 3/2007 | Scanlan et al. |
| 2007/0074719 A1 | 4/2007 | Danek et al. |
| 2007/0118142 A1 | 5/2007 | Krueger et al. |

(56) References Cited

U.S. PATENT DOCUMENTS

| | | |
|---|---|---|
| 2007/0129715 A1 | 6/2007 | Eggers et al. |
| 2007/0142791 A1 | 6/2007 | Yeung et al. |
| 2007/0142842 A1 | 6/2007 | Krueger et al. |
| 2007/0149966 A1 | 6/2007 | Dahla et al. |
| 2007/0179497 A1 | 8/2007 | Eggers et al. |
| 2007/0185231 A1 | 8/2007 | Liu et al. |
| 2007/0213584 A1 | 9/2007 | Kim et al. |
| 2007/0213735 A1 | 9/2007 | Saadat et al. |
| 2007/0260237 A1 | 11/2007 | Sutton et al. |
| 2008/0004621 A1 | 1/2008 | Dahla et al. |
| 2008/0004675 A1 | 1/2008 | King et al. |
| 2008/0009847 A1 | 1/2008 | Ricart et al. |
| 2008/0021447 A1 | 1/2008 | Davison et al. |
| 2008/0021463 A1 | 1/2008 | Georgy |
| 2008/0058707 A1 | 3/2008 | Ashley et al. |
| 2008/0065062 A1 | 3/2008 | Leung et al. |
| 2008/0091207 A1 | 4/2008 | Truckai et al. |
| 2008/0114364 A1 | 5/2008 | Goldin et al. |
| 2008/0119844 A1 | 5/2008 | Woloszko et al. |
| 2008/0119846 A1 | 5/2008 | Rioux |
| 2008/0132890 A1 | 6/2008 | Woloszko et al. |
| 2008/0161804 A1 | 7/2008 | Rioux et al. |
| 2008/0275458 A1 | 11/2008 | Bleich et al. |
| 2008/0281322 A1 | 11/2008 | Sherman et al. |
| 2008/0294166 A1 | 11/2008 | Goldin et al. |
| 2008/0294167 A1 | 11/2008 | Schumacher et al. |
| 2009/0030308 A1 | 1/2009 | Bradford et al. |
| 2009/0054951 A1 | 2/2009 | Lauthardt et al. |
| 2009/0069807 A1 | 3/2009 | Eggers et al. |
| 2009/0076520 A1 | 3/2009 | Choi |
| 2009/0105775 A1 | 4/2009 | Mitchell et al. |
| 2009/0112278 A1 | 4/2009 | Wingeier et al. |
| 2009/0118731 A1 | 5/2009 | Young et al. |
| 2009/0131867 A1 | 5/2009 | Liu et al. |
| 2009/0131886 A1 | 5/2009 | Liu et al. |
| 2009/0149846 A1 | 6/2009 | Hoey et al. |
| 2009/0149878 A1 | 6/2009 | Truckai et al. |
| 2009/0204192 A1 | 8/2009 | Carlton et al. |
| 2009/0222053 A1 | 9/2009 | Gaunt et al. |
| 2009/0312764 A1 | 12/2009 | Marino |
| 2010/0010392 A1 | 1/2010 | Skelton et al. |
| 2010/0016929 A1 | 1/2010 | Prochazka |
| 2010/0023006 A1 | 1/2010 | Ellman |
| 2010/0023065 A1 | 1/2010 | Welch et al. |
| 2010/0082033 A1 | 4/2010 | Germain |
| 2010/0094269 A1 | 4/2010 | Pellegrino et al. |
| 2010/0114098 A1 | 5/2010 | Carl |
| 2010/0145424 A1 | 6/2010 | Podhajsky et al. |
| 2010/0179556 A1 | 7/2010 | Scribner et al. |
| 2010/0185082 A1 | 7/2010 | Chandran et al. |
| 2010/0185161 A1 | 7/2010 | Pellegrino et al. |
| 2010/0211076 A1 | 8/2010 | Germain et al. |
| 2010/0222777 A1 | 9/2010 | Sutton et al. |
| 2010/0261989 A1 | 10/2010 | Boseck et al. |
| 2010/0261990 A1 | 10/2010 | Gillis et al. |
| 2010/0298737 A1 | 11/2010 | Koehler |
| 2010/0298822 A1 | 11/2010 | Behnke |
| 2010/0298832 A1 | 11/2010 | Lau et al. |
| 2010/0305559 A1 | 12/2010 | Brannan et al. |
| 2010/0324506 A1 | 12/2010 | Pellegrino |
| 2011/0022133 A1 | 1/2011 | Diederich et al. |
| 2011/0034884 A9 | 2/2011 | Pellegrino et al. |
| 2011/0040362 A1 | 2/2011 | Godara et al. |
| 2011/0077628 A1 | 3/2011 | Hoey et al. |
| 2011/0087314 A1 | 4/2011 | Diederich et al. |
| 2011/0118735 A1 | 5/2011 | Abou-Marie et al. |
| 2011/0130751 A1 | 6/2011 | Malis et al. |
| 2011/0144524 A1 | 6/2011 | Fish et al. |
| 2011/0152855 A1 | 6/2011 | Mayse et al. |
| 2011/0196361 A1 | 8/2011 | Vilims |
| 2011/0206260 A1 | 8/2011 | Bergmans et al. |
| 2011/0264098 A1 | 10/2011 | Cobbs |
| 2011/0270238 A1 | 11/2011 | Rizq et al. |
| 2011/0276001 A1 | 11/2011 | Schultz et al. |
| 2011/0295245 A1 | 12/2011 | Willyard et al. |
| 2011/0295261 A1 | 12/2011 | Germain |
| 2011/0319765 A1 | 12/2011 | Gertner et al. |
| 2012/0029420 A1 | 2/2012 | Vilims |
| 2012/0116266 A1 | 5/2012 | House et al. |
| 2012/0123427 A1 | 5/2012 | McGuckin et al. |
| 2012/0136346 A1 | 5/2012 | Condie et al. |
| 2012/0136348 A1 | 5/2012 | Condie et al. |
| 2012/0143090 A1 | 6/2012 | Hay et al. |
| 2012/0143341 A1 | 6/2012 | Zipnick |
| 2012/0172359 A1 | 7/2012 | Badiger et al. |
| 2012/0172858 A1 | 7/2012 | Harrison et al. |
| 2012/0172859 A1 | 7/2012 | Condie et al. |
| 2012/0191095 A1 | 7/2012 | Burger et al. |
| 2012/0196251 A1 | 8/2012 | Taft et al. |
| 2012/0197344 A1 | 8/2012 | Taft et al. |
| 2012/0203219 A1 | 8/2012 | Evans et al. |
| 2012/0226145 A1 | 9/2012 | Chang et al. |
| 2012/0226273 A1 | 9/2012 | Nguyen et al. |
| 2012/0239049 A1 | 9/2012 | Truckai et al. |
| 2012/0239050 A1 | 9/2012 | Linderman et al. |
| 2012/0259382 A1 | 10/2012 | Trier et al. |
| 2012/0259383 A1 | 10/2012 | Trier et al. |
| 2012/0265186 A1 | 10/2012 | Burger et al. |
| 2012/0330180 A1 | 12/2012 | Pellegrino et al. |
| 2012/0330300 A1 | 12/2012 | Pellegrino et al. |
| 2012/0330301 A1 | 12/2012 | Pellegrino et al. |
| 2013/0006232 A1 | 1/2013 | Pellegrino et al. |
| 2013/0006233 A1 | 1/2013 | Pellegrino et al. |
| 2013/0012933 A1 | 1/2013 | Pellegrino et al. |
| 2013/0012935 A1 | 1/2013 | Pellegrino et al. |
| 2013/0012936 A1 | 1/2013 | Pellegrino et al. |
| 2013/0012951 A1 | 1/2013 | Linderman |
| 2013/0060244 A1 | 3/2013 | Godara et al. |
| 2013/0079810 A1 | 3/2013 | Isenberg |
| 2013/0116688 A1 | 5/2013 | Kunis et al. |
| 2013/0197508 A1 | 8/2013 | Shikhman et al. |
| 2013/0231654 A1 | 9/2013 | Germain |
| 2013/0237979 A1 | 9/2013 | Shikhman et al. |
| 2013/0103022 A1 | 10/2013 | Sutton et al. |
| 2013/0261507 A1 | 10/2013 | Diederich et al. |
| 2013/0274784 A1 | 10/2013 | Lenker et al. |
| 2013/0296767 A1 | 11/2013 | Zarins et al. |
| 2013/0303873 A1 | 11/2013 | Voeroes et al. |
| 2013/0324993 A1 | 12/2013 | McCarthy et al. |
| 2013/0324994 A1 | 12/2013 | Pellegrino et al. |
| 2013/0324996 A1 | 12/2013 | Pellegrino et al. |
| 2013/0324997 A1 | 12/2013 | Pellegrino et al. |
| 2013/0331840 A1 | 12/2013 | Teisen et al. |
| 2013/0345765 A1 | 12/2013 | Brockman et al. |
| 2014/0031715 A1 | 1/2014 | Sherar et al. |
| 2014/0039500 A1 | 2/2014 | Pellegrino et al. |
| 2014/0046245 A1 | 2/2014 | Cornacchia |
| 2014/0046328 A1 | 2/2014 | Schumacher et al. |
| 2014/0066913 A1 | 3/2014 | Sherman |
| 2014/0088575 A1 | 3/2014 | Loeb |
| 2014/0148801 A1 | 5/2014 | Asher et al. |
| 2014/0148805 A1 | 5/2014 | Stewart et al. |
| 2014/0171942 A1 | 6/2014 | Werneth et al. |
| 2014/0194887 A1 | 7/2014 | Shenoy |
| 2014/0221967 A1 | 8/2014 | Childs et al. |
| 2014/0236137 A1 | 8/2014 | Tran et al. |
| 2014/0236144 A1 | 8/2014 | Krueger et al. |
| 2014/0243823 A1 | 8/2014 | Godara et al. |
| 2014/0243943 A1 | 8/2014 | Rao et al. |
| 2014/0257265 A1 | 9/2014 | Godara et al. |
| 2014/0257296 A1 | 9/2014 | Morgenstern Lopez |
| 2014/0271717 A1 | 9/2014 | Goshayeshgar et al. |
| 2014/0275760 A1 | 9/2014 | Lee et al. |
| 2014/0276713 A1 | 9/2014 | Hoey et al. |
| 2014/0276728 A1 | 9/2014 | Goshayeshgar et al. |
| 2014/0276744 A1 | 9/2014 | Arthur et al. |
| 2014/0288544 A1 | 9/2014 | Diederich et al. |
| 2014/0288546 A1 | 9/2014 | Sherman et al. |
| 2014/0296850 A1 | 10/2014 | Condie et al. |
| 2014/0303610 A1 | 10/2014 | McCarthy et al. |
| 2014/0303614 A1 | 10/2014 | McCarthy et al. |
| 2014/0316405 A1 | 10/2014 | Pellegrino et al. |
| 2014/0316413 A1 | 10/2014 | Burger et al. |
| 2014/0324051 A1 | 10/2014 | Pellegrino et al. |

(56) References Cited

U.S. PATENT DOCUMENTS

| | | |
|---|---|---|
| 2014/0330332 A1 | 11/2014 | Danek et al. |
| 2014/0331840 A1 | 11/2014 | Kani |
| 2014/0336630 A1 | 11/2014 | Woloszko |
| 2014/0336667 A1 | 11/2014 | Pellegrino et al. |
| 2014/0364842 A1 | 12/2014 | Werneth et al. |
| 2014/0371740 A1 | 12/2014 | Germain et al. |
| 2015/0005614 A1 | 1/2015 | Heggeness et al. |
| 2015/0005767 A1 | 1/2015 | Werneth et al. |
| 2015/0041521 A1 | 2/2015 | Matsushita et al. |
| 2015/0045783 A1 | 2/2015 | Edidin |
| 2015/0057658 A1 | 2/2015 | Sutton et al. |
| 2015/0065945 A1 | 3/2015 | Zarins et al. |
| 2015/0073515 A1 | 3/2015 | Turovskiy et al. |
| 2015/0105701 A1 | 4/2015 | Mayer et al. |
| 2015/0141876 A1 | 5/2015 | Diederich et al. |
| 2015/0157402 A1 | 6/2015 | Kunis et al. |
| 2015/0164546 A1 | 6/2015 | Pellegrino et al. |
| 2015/0196358 A1 | 7/2015 | Goshayeshgar |
| 2015/0216588 A1 | 8/2015 | Deem et al. |
| 2015/0231417 A1 | 8/2015 | Metcalf et al. |
| 2015/0250472 A1 | 9/2015 | Ek et al. |
| 2015/0257296 A1 | 9/2015 | Hung et al. |
| 2015/0272655 A1 | 10/2015 | Condie et al. |
| 2015/0273208 A1 | 10/2015 | Hamilton |
| 2015/0297246 A1 | 10/2015 | Patel et al. |
| 2015/0297282 A1 | 10/2015 | Cadouri |
| 2015/0320480 A1 | 11/2015 | Cosman, Jr. et al. |
| 2015/0335349 A1 | 11/2015 | Pellegrino et al. |
| 2015/0335382 A1 | 11/2015 | Pellegrino et al. |
| 2015/0342619 A1 | 12/2015 | Weitzman |
| 2015/0342660 A1 | 12/2015 | Nash |
| 2015/0342670 A1 | 12/2015 | Pellegrino et al. |
| 2015/0359586 A1 | 12/2015 | Heggeness |
| 2015/0374432 A1 | 12/2015 | Godara et al. |
| 2015/0374992 A1 | 12/2015 | Crosby et al. |
| 2015/0374995 A1 | 12/2015 | Foreman et al. |
| 2016/0000601 A1 | 1/2016 | Burger et al. |
| 2016/0001096 A1 | 1/2016 | Mishelevich |
| 2016/0002627 A1 | 1/2016 | Bennett et al. |
| 2016/0008593 A1 | 1/2016 | Cairns |
| 2016/0008618 A1 | 1/2016 | Omar-Pasha |
| 2016/0008628 A1 | 1/2016 | Morries et al. |
| 2016/0016012 A1 | 1/2016 | Youn et al. |
| 2016/0022988 A1 | 1/2016 | Thieme et al. |
| 2016/0022994 A1 | 1/2016 | Moffitt et al. |
| 2016/0024208 A1 | 1/2016 | MacDonald et al. |
| 2016/0027791 A1 | 1/2016 | Zhang |
| 2016/0029930 A1 | 2/2016 | Plumley et al. |
| 2016/0030276 A1 | 2/2016 | Spanyer |
| 2016/0030408 A1 | 2/2016 | Levin |
| 2016/0030748 A1 | 2/2016 | Edgerton et al. |
| 2016/0030765 A1 | 2/2016 | Towne et al. |
| 2016/0045207 A1 | 2/2016 | Kovacs et al. |
| 2016/0045256 A1 | 2/2016 | Godara et al. |
| 2016/0045868 A1 | 2/2016 | Sonntag et al. |
| 2016/0051831 A1 | 2/2016 | Lundmark et al. |
| 2016/0059007 A1 | 3/2016 | Koop |
| 2016/0074068 A1 | 3/2016 | Patwardhan |
| 2016/0074133 A1 | 3/2016 | Shikhman et al. |
| 2016/0074279 A1 | 3/2016 | Shin |
| 2016/0074661 A1 | 3/2016 | Lipani |
| 2016/0081716 A1 | 3/2016 | Boling et al. |
| 2016/0081810 A1 | 3/2016 | Reiley et al. |
| 2016/0095721 A1 | 4/2016 | Schell et al. |
| 2016/0106443 A1 | 4/2016 | Kuntz et al. |
| 2016/0106985 A1 | 4/2016 | Zhu |
| 2016/0106994 A1 | 4/2016 | Crosby et al. |
| 2016/0113704 A1 | 4/2016 | Godara et al. |
| 2016/0115173 A1 | 4/2016 | Bois et al. |
| 2016/0136310 A1 | 5/2016 | Bradford et al. |
| 2016/0144182 A1 | 5/2016 | Bennett et al. |
| 2016/0144187 A1 | 5/2016 | Caparso et al. |
| 2016/0158551 A1 | 6/2016 | Kent et al. |
| 2016/0166302 A1 | 6/2016 | Tan-Malecki et al. |
| 2016/0166835 A1 | 6/2016 | De Ridder |
| 2016/0175586 A1 | 6/2016 | Edgerton et al. |
| 2016/0199097 A1 | 7/2016 | Linderman et al. |
| 2016/0199117 A1 | 7/2016 | Druma |
| 2016/0213927 A1 | 7/2016 | McGee et al. |
| 2016/0220317 A1 | 8/2016 | Shikhman et al. |
| 2016/0220393 A1 | 8/2016 | Slivka et al. |
| 2016/0220638 A1 | 8/2016 | Dony et al. |
| 2016/0220672 A1 | 8/2016 | Chalasani et al. |
| 2016/0228131 A1 | 8/2016 | Brockman et al. |
| 2016/0228696 A1 | 8/2016 | Imran et al. |
| 2016/0235471 A1 | 8/2016 | Godara et al. |
| 2016/0235474 A1 | 8/2016 | Prisco et al. |
| 2016/0243353 A1 | 8/2016 | Ahmed |
| 2016/0246944 A1 | 8/2016 | Jain et al. |
| 2016/0250469 A1 | 9/2016 | Kim et al. |
| 2016/0250472 A1 | 9/2016 | Carbunaru |
| 2016/0262830 A1 | 9/2016 | Werneth et al. |
| 2016/0262904 A1 | 9/2016 | Schaller et al. |
| 2016/0271405 A1 | 9/2016 | Angara et al. |
| 2016/0278791 A1 | 9/2016 | Pellegrino et al. |
| 2016/0278846 A1 | 9/2016 | Harrison et al. |
| 2016/0278861 A1 | 9/2016 | Ko |
| 2016/0279190 A1 | 9/2016 | Watts et al. |
| 2016/0279408 A1 | 9/2016 | Grigsby et al. |
| 2016/0279411 A1 | 9/2016 | Rooney et al. |
| 2016/0279441 A1 | 9/2016 | Imran |
| 2016/0302925 A1 | 10/2016 | Keogh et al. |
| 2016/0302936 A1 | 10/2016 | Billon et al. |
| 2016/0310739 A1 | 10/2016 | Burdick et al. |
| 2016/0317053 A1 | 11/2016 | Srivastava |
| 2016/0317211 A1 | 11/2016 | Harrison et al. |
| 2016/0317621 A1 | 11/2016 | Bright |
| 2016/0324541 A1 | 11/2016 | Pellegrino et al. |
| 2016/0324677 A1 | 11/2016 | Hyde et al. |
| 2016/0325100 A1 | 11/2016 | Lian et al. |
| 2016/0339251 A1 | 11/2016 | Kent et al. |
| 2016/0354093 A1 | 12/2016 | Pellegrino et al. |
| 2016/0354233 A1 | 12/2016 | Sansone et al. |
| 2016/0367797 A1 | 12/2016 | Eckermann |
| 2016/0367823 A1 | 12/2016 | Cowan et al. |
| 2016/0375254 A1 | 12/2016 | Walker et al. |
| 2016/0375259 A1 | 12/2016 | Davis et al. |
| 2017/0000501 A1 | 1/2017 | Aho et al. |
| 2017/0001026 A1 | 1/2017 | Schwarz et al. |
| 2017/0007277 A1 | 1/2017 | Drapeau et al. |
| 2017/0014169 A1 | 1/2017 | Dean et al. |
| 2017/0027618 A1 | 2/2017 | Lee et al. |
| 2017/0028198 A1 | 2/2017 | Degiorgio et al. |
| 2017/0028201 A1 | 2/2017 | Howard |
| 2017/0035483 A1 | 2/2017 | Crainich et al. |
| 2017/0036009 A1 | 2/2017 | Hughes et al. |
| 2017/0036025 A1 | 2/2017 | Sachs et al. |
| 2017/0036033 A9 | 2/2017 | Perryman et al. |
| 2017/0042834 A1 | 2/2017 | Westphal et al. |
| 2017/0049500 A1 | 2/2017 | Shikhman et al. |
| 2017/0049503 A1 | 2/2017 | Cosman |
| 2017/0049507 A1 | 2/2017 | Cosman |
| 2017/0049513 A1 | 2/2017 | Cosman |
| 2017/0050017 A1 | 2/2017 | Cosman |
| 2017/0050021 A1 | 2/2017 | Cosman |
| 2017/0050024 A1 | 2/2017 | Bhadra et al. |
| 2017/0056028 A1 | 3/2017 | Germain et al. |
| 2017/0065329 A1 | 3/2017 | Benamou et al. |
| 2017/0112507 A1 | 4/2017 | Crainich et al. |
| 2017/0119461 A1 | 5/2017 | Godara et al. |
| 2017/0128080 A1 | 5/2017 | Torrie |
| 2017/0128112 A1 | 5/2017 | Germain |
| 2017/0135742 A1 | 5/2017 | Lee et al. |
| 2017/0164998 A1 | 6/2017 | Klimovitch |
| 2017/0172650 A1 | 6/2017 | Germain |
| 2017/0181788 A1 | 6/2017 | Dastjerdi et al. |
| 2017/0202613 A1 | 7/2017 | Pellegrino |
| 2017/0238943 A1 | 8/2017 | Sennett et al. |
| 2017/0246481 A1 | 8/2017 | Mishelevich |
| 2017/0266419 A1 | 9/2017 | Goshayeshgar |
| 2017/0303983 A1 | 10/2017 | Linderman et al. |
| 2017/0312007 A1 | 11/2017 | Harlev et al. |
| 2017/0333052 A1 | 11/2017 | Ding et al. |
| 2018/0021048 A1 | 1/2018 | Pellegrino et al. |

(56) References Cited

U.S. PATENT DOCUMENTS

| | | |
|---|---|---|
| 2018/0042656 A1 | 2/2018 | Edidin |
| 2018/0055539 A1 | 3/2018 | Pellegino |
| 2018/0103964 A1 | 4/2018 | Patel et al. |
| 2018/0140245 A1 | 5/2018 | Tapio |
| 2018/0153604 A1 | 6/2018 | Ayvazyan et al. |
| 2018/0161047 A1 | 6/2018 | Purdy et al. |
| 2018/0193088 A1 | 7/2018 | Sutton et al. |
| 2019/0029698 A1 | 1/2019 | Pellegrino et al. |
| 2019/0038296 A1 | 2/2019 | Pellegrino et al. |
| 2019/0038340 A1 | 2/2019 | Singh |
| 2019/0038343 A1 | 2/2019 | Sutton et al. |
| 2019/0038344 A1 | 2/2019 | Pellegrino |
| 2019/0038345 A1 | 2/2019 | Pellegrino |
| 2019/0090933 A1 | 3/2019 | Pellegrino et al. |
| 2019/0110833 A1 | 4/2019 | Pellegrino et al. |
| 2019/0118003 A1 | 4/2019 | Diederich et al. |
| 2019/0118004 A1 | 4/2019 | Diederich et al. |
| 2019/0118005 A1 | 4/2019 | Diederich et al. |
| 2019/0175252 A1 | 6/2019 | Heggeness |
| 2019/0282268 A1 | 9/2019 | Pellegrino et al. |
| 2019/0290269 A1 | 9/2019 | Shelton et al. |
| 2019/0290296 A1 | 9/2019 | Patel et al. |
| 2019/0298392 A1 | 10/2019 | Capote et al. |
| 2019/0365416 A1 | 12/2019 | Brockman et al. |
| 2020/0000480 A1 | 1/2020 | Alambeigi et al. |
| 2020/0016406 A1 | 1/2020 | Alataris et al. |
| 2020/0022709 A1 | 1/2020 | Burger et al. |
| 2020/0030601 A1 | 1/2020 | Molnar et al. |
| 2020/0060695 A1 | 2/2020 | Purdy et al. |
| 2020/0060747 A1 | 2/2020 | Edidin |
| 2020/0069920 A1 | 3/2020 | Goshayeshgar |
| 2020/0078083 A1 | 3/2020 | Sprinkle et al. |
| 2020/0138454 A1 | 5/2020 | Patel et al. |
| 2020/0146743 A1 | 5/2020 | Defosset et al. |
| 2020/0146744 A1 | 5/2020 | Defosset et al. |
| 2020/0214762 A1 | 7/2020 | Pellegrino et al. |
| 2020/0281646 A1 | 9/2020 | Pellegrino et al. |
| 2021/0022814 A1 | 1/2021 | Crawford et al. |
| 2021/0113238 A1 | 4/2021 | Donovan et al. |
| 2021/0113239 A1 | 4/2021 | Donovan et al. |
| 2021/0177502 A1 | 6/2021 | Wright et al. |
| 2021/0361350 A1 | 11/2021 | Pellegrino et al. |
| 2021/0361351 A1 | 11/2021 | Pellegrino et al. |
| 2021/0369323 A1 | 12/2021 | Edidin |
| 2021/0386491 A1 | 12/2021 | Shmayahu et al. |
| 2022/0015775 A1 | 1/2022 | Patel et al. |
| 2022/0192702 A1 | 6/2022 | Donovan |
| 2022/0296255 A1 | 9/2022 | Patel et al. |

FOREIGN PATENT DOCUMENTS

| | | |
|---|---|---|
| CN | 1792455 A | 6/2006 |
| CN | 103157480 A | 6/2013 |
| CN | 106111118 A | 11/2016 |
| DE | 4323585 A1 | 1/1995 |
| EP | 0040658 | 12/1981 |
| EP | 0351057 A1 | 1/1990 |
| EP | 0584959 | 3/1994 |
| EP | 0597463 | 5/1994 |
| EP | 0872215 A2 | 10/1998 |
| EP | 0880938 | 12/1998 |
| EP | 1013228 | 6/2000 |
| EP | 1059067 | 12/2000 |
| EP | 1059087 | 12/2000 |
| EP | 1294323 B1 | 4/2007 |
| EP | 1938765 A1 | 7/2008 |
| EP | 2092952 A1 | 8/2009 |
| EP | 1471836 B1 | 4/2010 |
| EP | 2339972 A2 | 7/2011 |
| EP | 2508225 A1 | 10/2012 |
| EP | 2759276 A1 | 7/2014 |
| EP | 2785260 B1 | 8/2015 |
| EP | 2913081 A1 | 9/2015 |
| EP | 2965782 A1 | 1/2016 |
| EP | 2582289 B1 | 9/2016 |
| EP | 3078395 A1 | 10/2016 |
| EP | 2205313 B1 | 11/2016 |
| EP | 3097946 A1 | 11/2016 |
| EP | 2341980 B1 | 1/2017 |
| JP | 53-139791 U | 11/1978 |
| JP | 60-016764 U | 2/1985 |
| JP | 6-47058 | 2/1994 |
| JP | 10-290806 | 11/1998 |
| JP | 2001-037760 | 2/2001 |
| JP | 2002-531229 A | 9/2002 |
| JP | 2005-169012 | 6/2005 |
| JP | 5522316 B2 | 6/2014 |
| KR | 10-1631487 B1 | 6/2016 |
| WO | WO 96/36289 | 11/1996 |
| WO | WO 98/27876 | 7/1998 |
| WO | WO 98/34550 | 8/1998 |
| WO | WO 9919025 | 4/1999 |
| WO | WO 99/44519 | 9/1999 |
| WO | WO 99/48621 | 9/1999 |
| WO | 00/13228 A1 | 3/2000 |
| WO | WO 00/21448 | 4/2000 |
| WO | WO 00/33909 | 6/2000 |
| WO | WO 00/49978 | 8/2000 |
| WO | WO 00/56237 | 9/2000 |
| WO | 00/67848 A1 | 11/2000 |
| WO | WO 00/67648 | 11/2000 |
| WO | WO 00/67656 | 11/2000 |
| WO | WO 01/01877 | 1/2001 |
| WO | 01/26570 A1 | 4/2001 |
| WO | WO 01/45579 | 6/2001 |
| WO | WO 01/57655 | 8/2001 |
| WO | WO 02/05699 | 1/2002 |
| WO | WO 02/05897 | 1/2002 |
| WO | WO 02/28302 | 4/2002 |
| WO | WO2002/026319 | 4/2002 |
| WO | WO 02/054941 | 7/2002 |
| WO | WO 02/067797 | 9/2002 |
| WO | WO 02/096304 | 12/2002 |
| WO | WO2006/044794 | 4/2006 |
| WO | WO2007/001981 | 1/2007 |
| WO | WO2007/008954 | 1/2007 |
| WO | WO 07/31264 | 3/2007 |
| WO | WO 08/001385 | 1/2008 |
| WO | WO 08/008522 | 1/2008 |
| WO | WO02/54941 | 5/2008 |
| WO | WO 2008/076330 A1 | 6/2008 |
| WO | WO 2008/076357 A1 | 6/2008 |
| WO | WO 08/121259 | 10/2008 |
| WO | WO 2008/121259 A2 | 10/2008 |
| WO | WO2008/141104 | 11/2008 |
| WO | WO 2008/144709 A2 | 11/2008 |
| WO | WO 2008140519 | 11/2008 |
| WO | 2009/001385 A1 | 12/2008 |
| WO | 2009/008522 A1 | 1/2009 |
| WO | 2009/051897 A1 | 4/2009 |
| WO | WO2009/076461 | 6/2009 |
| WO | 2009/121259 A1 | 10/2009 |
| WO | WO 2009/124192 | 10/2009 |
| WO | 2009/140519 A1 | 11/2009 |
| WO | WO 2009/155319 A1 | 12/2009 |
| WO | 2010/036865 A2 | 4/2010 |
| WO | WO 2010/111246 A1 | 9/2010 |
| WO | WO 2010/135606 A1 | 11/2010 |
| WO | WO 2011/041038 A1 | 4/2011 |
| WO | 2011/134080 A1 | 11/2011 |
| WO | 2011/157714 A1 | 12/2011 |
| WO | 2012/024162 A1 | 2/2012 |
| WO | 2012/065753 A1 | 5/2012 |
| WO | 2012/074932 A2 | 6/2012 |
| WO | 2013/009516 A2 | 1/2013 |
| WO | 2013/101772 A1 | 7/2013 |
| WO | 2013/134452 A1 | 9/2013 |
| WO | 2013/168006 A2 | 11/2013 |
| WO | 2013/180947 A1 | 12/2013 |
| WO | 2014/004051 A2 | 1/2014 |
| WO | 2014/130231 A1 | 8/2014 |
| WO | 2014/141207 A2 | 9/2014 |
| WO | 2014/145222 A2 | 9/2014 |
| WO | 2014/145659 A1 | 9/2014 |

(56) References Cited

FOREIGN PATENT DOCUMENTS

| | | |
|---|---|---|
| WO | 2014/146029 A1 | 9/2014 |
| WO | 2014/165194 A1 | 10/2014 |
| WO | 2014/176141 A2 | 10/2014 |
| WO | 2014/197596 A1 | 12/2014 |
| WO | 2014/210373 A1 | 12/2014 |
| WO | 2015/024013 A2 | 2/2015 |
| WO | 2015/038317 A2 | 3/2015 |
| WO | 2015/044945 A1 | 4/2015 |
| WO | 2015/047817 A1 | 4/2015 |
| WO | 2015/057696 A1 | 4/2015 |
| WO | 2015/060927 A2 | 4/2015 |
| WO | 2015/066295 A1 | 5/2015 |
| WO | 2015/066303 A1 | 5/2015 |
| WO | 2015/079319 A1 | 6/2015 |
| WO | 2015/148105 A1 | 10/2015 |
| WO | 2016/033380 A1 | 3/2016 |
| WO | 2016/048965 A1 | 3/2016 |
| WO | 2016/069157 A1 | 5/2016 |
| WO | 2016/075544 A2 | 5/2016 |
| WO | 2016/090420 A1 | 6/2016 |
| WO | 2016/105448 A1 | 6/2016 |
| WO | 2016/105449 A1 | 6/2016 |
| WO | 2016/127130 A1 | 8/2016 |
| WO | 2016/130686 A1 | 8/2016 |
| WO | 2016/134273 A1 | 8/2016 |
| WO | 2016/148954 A1 | 9/2016 |
| WO | 2016/154091 A1 | 9/2016 |
| WO | 2016/168381 A1 | 10/2016 |
| WO | WO2009/042172 | 11/2016 |
| WO | 2016/209682 A1 | 12/2016 |
| WO | 2017/009472 A1 | 1/2017 |
| WO | 2017/010930 A1 | 1/2017 |
| WO | 2017/019863 A1 | 2/2017 |
| WO | 2017/027703 A1 | 2/2017 |
| WO | 2017/027809 A1 | 2/2017 |
| WO | 2018/116273 A1 | 6/2018 |
| WO | 2020/198150 A2 | 10/2020 |

OTHER PUBLICATIONS

Antonacci, M. Darryl et al.; Innervation of the Human Vertebral Body: A Histologic Study; Journal of Spinal Disorder, vol. 11, No. 6, pp. 526-531, 1998 Lippincott Williams & Wilkins, Philadelphia.

Arnoldi, Carl C.; Intraosseous Hypertension—A Possible Cause of Low Back Pain?; Clinical Orthopedics and Related Research, No. 115, Mar.-Apr. 1976.

Bailey, Jeannie F., "Innervation Patterns of PGP 9.5-Positive Nerve Fibers within the Human Lumbar Vertebra, Journal of Anatomy", (2011) 218, pp. 263-270, San Francisco, California.

Becker, Stephan, et al., "Ablation of the basivertebral nerve for treatment of back pain: a clinical study," The Spine Journal, vol. 17, pp. 218-223 (Feb. 2017).

Bergeron et al., "Fluoroscopic-guided radiofrequency ablation of the basivertebral nerve: application and analysis with multiple imaging modalities in an ovine model," Thermal Treatment of Tissue: Energy Delivery and Assessment III, edited by Thomas P. Ryan, Proceedings of SPIE, vol. 5698 (SPIE, Bellingham, WA, 2005) pp. 156-167.

Bogduk, N., The anatomy of the lumbar intervertebral disc syndrome, Med J. Aust. 1976, vol. 1, No. 23, pp. 878-881.

Bogduk, Nikolai, et al.; Technical Limitations to the efficacy of Radiofrequency Neurotomy for Spinal Pain; Neurosurgery vol. 20, No. 4, 1987.

Choy, Daniel SS.J. et al.; Percutaneous Laser Disc Decompression, A New Therapeutic Modality; Spine vol. 17, No. 8, 1992.

Cosman, E.R. et al., Theoretical Aspects of Radiofrequency Lesions in the Dorsal Root Entry Zone. Neurosurgery, vol. 1, No. 6, 1984, pp. 945-950.

Deardorff, Dana L. et al.; Ultrasound applicators with internal cooling for interstitial thermal therapy; SPIE vol. 3594, 1999.

Deramond, H. et al., Temperature Elevation Caused by Bone Cement Polymerization During Vertebroplasty, Bone, Aug. 1999, pp. 17S-21S, vol. 25, No. 2, Supplement.

Diederich, C. J. et al., "IDTT Therapy in Cadaveric Lumbar Spine: Temperature and thermaldose distributions, Thermal Treatment of Tissue: Energy Delivery and Assessment," Thomas P. Ryan, Editor, Proceedings of SPIE vol. 4247:104-108 (2001).

Diederich, Chris J. et al.; Ultrasound Catheters for Circumferential Cardiac Ablation; SPIE vol. 3594 (1999).

Dupuy, D.E. et al. Radiofrequency ablation of spinal tumors: Temperature distribution in the spinal canal AJR, vol. 175, pp. 1263-1266, Nov. 2000.

Dupuy, Damian E.; Radiofrequency Ablation: An Outpatient Percutaneous Treatment; Medicine and Health-Rhode Island vol. 82, No. 6, Jun. 1999.

Esses, Stephen I. et al.; Intraosseous Vertebral Body Pressures; Spine vol. 17 No. 6 Supplement 1992.

FDA Response to 510(k) Submission by Relievant Medsystems, Inc. submitted on Sep. 27, 2007 (date stamped on Oct. 5, 2007) and associated documents.

Fras M.D., Christian et al., "Substance P-containing Nerves within the Human Vertebral Body: An Immunohistochemical Study of the Basivertebral Nerve", The Spine Journal 3, 2003, pp. 63-67.

Goldberg, S.N. et al., Tissue ablation with radiofrequency: Effect of probe size, gauge, duration, and temperature on lesion volume, Acad. Radiol., vol. 2, pp. 399-404 (1995).

Hanai, Kenji et al.; Simultaneous Measurement of Intraosseous and Cerebrospinal Fluid Pressures in the Lumbar Region; Spine vol. 10, No. 1, 1985.

Heggeness, M. et al Ablation of the Basivertebral Nerve for the Treatment of Back Pain: A Pilot Clinical Study; The Spine Journal, 2011, vol. 11, Issue 10, Supplement, pp. S65-S66, ISSN 1529-9430.

Heggeness, Michael H. et al., The Trabecular Anatomy of Thoracolumbar Vertebrae: Implications for Burst Fractures, Journal of Anatomy, 1997, pp. 309-312, vol. 191, Great Britain.

Heggeness, Michael H. et al. Discography Causes End Plate Deflection; Spine vol. 18, No. 8, pp. 1050-1053, 1993, J.B. Lippincott Company.

Hoopes et al., "Radiofrequency Ablation of The Basivertebral Nerve as a Potential Treatment of Back Pain: Pathologic Assessment in an Ovine Model," Thermal Treatment of Tissue: Energy Delivery and Assessment III, edited by Thomas P. Ryan, Proceedings of SPIE, vol. 5698 (SPIE, Bellingham, WA, 2005) pp. 168-180.

Houpt, Jonathan C. et al.; Experimental Study of Temperature Distributions and Thermal Transport During Radiofrequency Current Therapy of the Intervertebral Disc; Spine vol. 21, No. 15, pp. 1808-1813, 1996, Lippincott-Raven Publishers.

Kleinstueck, Frank S. et al.; Acute Biomechanical and Histological Effects of Intradiscal Electrothermal Therapy on Human Lumbar Discs; Spine vol. 26, No. 20, pp. 2198-2207; 2001, Lippincott Williams & Wilkins, Inc.

Kopecky, Kenyon K. et al. "Side-Exiting Coaxial Needle for Aspiration Biopsy"—AJR—1996; 167, pp. 661-662.

Lehmann, Justus F. et al.; Selective Heating Effects of Ultrasound in Human Beings; Archives of Physical Medicine & Rehabilitation Jun. 1966.

Letcher, Frank S. et al.; The Effect of Radiofrequency Current and Heat on Peripheral Nerve Action Potential in the Cat; U.S. Naval Hospital, Philadelphia, PA (1968).

Lundskog, Jan; Heat and Bone Tissue—an experimental investigation of the thermal properties of bone tissue and threshold levels for thermal injury; Scandinavian Journal of Plastic and Reconstructive Surgery Supplemental 9, From the Laboratory of Experimental Biology, Department of anatomy, University of Gothenburg, Gothenburg, Sweden, Goteborg 1972.

Martin, J.B. et al., Vertebroplasty: Clinical Experience and Follow-up Results, Bone, Aug. 1999, pp. 11S-15S, vol. 25, No. 2, Supplement.

Massad, Malek M.D. et al.; Endoscopic Thoracic Sympathectomy: Evaluation of Pulsatile Laser, Non-Pulsatile Laser, and Radiofrequency-Generated Thermocoagulation; Lasers in Surgery and Medicine; 1991; pp. 18-25.

(56) References Cited

OTHER PUBLICATIONS

Mehta, Mark et al.; The treatment of chronic back pain; Anaesthesia, 1979, vol. 34, pp. 768-775.
Nau, William H., Ultrasound interstitial thermal therapy (USITT) in the prostate; SPIE vol. 3594 (Jan. 1999).
Rashbaum, Ralph F.; Radiofrequency Facet Denervation A Treatment alternative in Refractory Low Back Pain with or without Leg Pain; Orthopedic Clinics of North America—vol. 14, No. 3, Jul. 1983.
Rosenthal, D.I., Seminars in Musculoskeletal Radiology, vol. 1, No. 2., pp. 265-272 (1997).
Ryan et al., "Three-Dimensional Finite Element Simulations of Vertebral Body Thermal Treatment," Thermal Treatment of Tissue: Energy Delivery and Assessment III, edited by Thomas P. Ryan, Proceedings of SPIE, vol. 5698 (SPIE, Bellingham, WA, 2005) pp. 137-155.
Shealy, C. Norman; Percutaneous radiofrequency denervation of spinal facets Treatment for chronic back pain and sciatica; Journal of Neurosurgery—vol. 43—Oct. 1975.
Sherman, Mary S.; The Nerves of Bone, The Journal of Bone and Joint Surgery, Apr. 1963, pp. 522-528, vol. 45-A, No. 3.
Solbiati, L. et al. Hepatic metastases: Percutaneous radio-frequency ablation with cooled-tip electrodes. Interventional Radiology, vol. 205, No. 2, pp. 367-373 (1997).
Stanton, Terry, "Can Nerve Ablation Reduce Chronic Back Pain?" AAOS Now (Jan. 2012).
The AVAmax System—Cardinal Health Special Procedures, Lit. No. 25P0459-01—www.cardinal.com (copyright 2007).
Tillotson, L. et al. Controlled thermal injury of bone: Report of a percutaneous technique using radiofrequency electrode and generator. Investigative Radiology, Nov. 1989, pp. 888-892.
Troussier, B. et al.; Percutaneous Intradiscal Radio-Frequency Thermocoagulation A Cadaveric Study; Spine vol. 20, No. 15, pp. 1713-1718, 1995, Lippincott-Raven Publishers.
Ullrich, Jr., Peter F., "Lumbar Spinal Fusion Surgery" Jan. 9, 2013, Spine-Health (available via wayback machine Internet archive at http:—web.archive.org-web-20130109095419—http:—www-spine-health.com-treatment-spinal-fusion-lumbar-spinal-fusion-surgery).
Caragee, EG et al.; "Discographic, MRI and psychosocial determinants of low back pain disability and remission: A prospective study in subjects with benign persistent back pain", The Spine Journal: The Official Journal of the North American Spine Society, vol. 5(1), pp. 24-35 (2005).
Fields, AJ et al; "Innervation of pathologies in the lumbar vertebral endplate and intervertebral disc", The Spine Journal: Official Journal of the North American Spine Society, vol. 14(3), pp. 513-521 (2014).
Fields, Aaron J. et al; "Cartilage endplate damage strongly associates with chronic low back pain, independent of modic changes", Abstract form Oral Presentation at the ISSLS Annual Meeting in Banff, Canada (May 14-18, 2018).
Fischgrund JS, et al.; "Intraosseous Basivertebral Nerve Ablation for the Treatment of Chronic Low Back Pain: 2-Year Results from a Prospective Randomized Double-Blind Sham-Controlled Multicenter Study", International Journal of Spine Surgery, vol. 13 (2), pp. 110-119 (2019).
Gehl, J., "Electroporation: theory and methods, perspectives for drug delivery, gene therapy, and research", Acta Physiol. Scand., vol. 177, pp. 437-447 (2003).
Gomet, Matthew G et al.; "Magnetic resonance spectroscopy (MRS) can identify painful lumbar discs and may facilitate improved clinical outcomes of lumbar surgeries for discogenic pain", European Spine Journal, vol. 28, pp. 674-687 (2019).
Jourabchi, Natanel et al.; "Irreversible electroporation (NanoKnife) in cancer treatment," Gastrointestinal Intervention, vol. 3, pp. 8-18 (2014).
Khalil, J et al.; "A Prospective, Randomized, Multi-Center Study of Intraosseous Basivertebral Nerve Ablation for the Treatment of Chronic Low Back Pain", The Spine Journal (2019), available at https://doi.org/10.1016/jspinee.2019.05.598.
Kim et al., Transforaminal epiduroscopic basivertebral nerve laser ablation for chronic low back pain associated with modic changes: A preliminary open-label study. Pain Research and Management 2018; https://pubmed.ncbi.nlm.nih.gov/30186540.
Kuisma M et al.; "Modic changes in endplates of lumbar vertebral bodies: Prevalence and association with low back and sciatic pain among middle-aged male workers", Spine, vol. 32(10), pp. 1116-1122 (2007).
Lotz JC, et al.; "The Role of the Vertebral End Plate in Low Back Pain", Global Spine Journal, vol. 3, pp. 153-164 (2013).
Modic MT et al.; "Degenerative disk disease: assessment of changes in vertebral body marrow with MR imaging", Radiology, vol. 166, pp. 193-199 (1988).
Mok, Florence et al.; "Modic changes of the lumbar spine: Prevalence, risk factors, and association with disc degeneration and low back pain in a large-scale population-based cohort", The Spine Journal: Official Journal of the North American Spine Society, vol. 16(1), pp. 32-41 (2016).
Pang, Henry et al,; The UTE Disc Sign on MRI: A Novel Imaging Biomarker Associated With Degenerative Spine Changes, Low Back Pain, and Disability, Spine, vol. 42 (Aug. 2017).
Radiological Society of North America. "Pulsed radiofrequency relieves acute back pain and sciatica." ScienceDaily. ScienceDaily, Nov. 27, 2018. <www.sciencedaily.com/releases/2018/11/181127092604.htm>.
Rahme et al., The modic vertebral endplate and marrow changes: pathologic significance and relation to low back pain and segmental instability of the lumbar spine. American Journal of Neuroradiology 29.5 (2008): 838-842; http://www.ajnr.org/content/29/5/838.
Weishaupt, D et al,; "Painful Lumbar Disk Derangement: Relevance of Endplate Abnormalities at MR Imaging", Radiology, vol. 218(2), pp. 420-427 (2001).
YouTube Video, "DFINE-STAR Procedure Animation," dated Sep. 30, 2013, can be viewed at https://www.youtube.com/watch?v=YxtKNyc2e-0.
Brandy Scott, The Avamax (Trademark) System—A New Level of Control, Cardinal Health, Oct. 28, 2009, 8 pages.
C.L. Tillotson et al. Controlled thermal injury of bone: Report of a percutaneous technique using radiofrequency electrode and generator. Investigative Radiology, Nov. 1989, pp. 888-892.
Deramond H. et al. Temperature Elevation Caused by Bone Cement Polymerization During Vertebroplasty Bone Aug. 1999 p. 17S-21S vol. 25 No. 2 Supplement.
DFINE-STAR Procedure Animation, Available online <https://www.youtube.com/watch?v=YxtKNyc2e-0>, Sep. 30, 2013, 1 page.
Dupuy, D. E., et al., "Radiofrequency Ablation: An Outpatient Percutaneous Treatment", Medicine Healt Rhode Island, vol. 82, No. 6, Jun. 1999, 6 pages.
E.R. Cosman et al. Theoretical aspects of radiofrequency lesions in the dorsal root entry zone. Neurosurgery, vol. 15, No. 6, pp. 945-950 (1984).
Embargoed for Release, "A Novel Approach for Treating Chronic Lower Back Pain", North American Spine society, 26th annual meeting, Nov. 2011, 2 pages.
European Search Report and Search Opinion received for European Application No. 03256168.0, mailed on Jan. 14, 2004, 3 pages.
European Search Report and Search Opinion received for European Application No. 05021597.9, mailed on May 23, 2008, 6 pages.
European Search Report and Search Opinion received for European Application No. 10012523.6, mailed on Oct. 1, 2012, 5 pages.
European Search Report and Search Opinion received for European Application No. 18166323.8, mailed on Oct. 25, 2018, 7 pages.
Goldberg S.N. et al. Tissue ablation with radiofrequency: Effect of probe size gauge duration and temperature on lesion vol. Acad. Radiol, vol. 2 pp. 399-404 (1995).
Intention to grant received for European Patent Application No. 11732213.1, mailed on Mar. 28, 2019, 6 pages.
International Preliminary Report on Patentability received for PCT Patent Application No. PCT/CN2017/119423, mailed on Jul. 11, 2019, 6 pages.
International Preliminary Report on Patentability received for PCT Patent Application No. PCT/US09/58329, mailed on Apr. 7, 2011, 7 pages.

(56) References Cited

OTHER PUBLICATIONS

International Preliminary Report on Patentability received for PCT Patent Application No. PCT/US11/20535, mailed on Jul. 19, 2012, 7 pages.
International Search Report and Written Opinion received for PCT Patent Application No. PCT/CN2017/119423, mailed on Apr. 3, 2018, 8 pages.
International Search Report and Written Opinion received for PCT Patent Application No. PCT/US09/58329, mailed on Apr. 30, 2010, 15 pages.
International Search Report and Written Opinion received for PCT Patent Application No. PCT/US11/20535, mailed on Oct. 4, 2011, 9 pages.
Macadaeg et al, A prospective single ami study of intraosseous basivertebral nerve ablation for the treatment of chronic low back pain: 12-month results. North American Spine Society Journal; May 27, 2020, 8 pages.
Marshall, R. U., et al., "clinical orthopaedics and related research", The Associate Editors The Board Of Advisory Editors The Board Of Corresponding Editors, 1972, 7 pages.
Osteocool Pain Management Brochure, Baylis Medical, copyright 2011.
Pulsed radiofrequency relieves acute back pain and sciatica, Science Daily, Nov. 27, 2018, 3 pages.
Ryan, T. P., et al., "Three-dimensional finite element simulations of vertebral body thermal treatment (Invited Paper)", Spine, Apr. 14, 2005, 19 pages.
Vadala et al., "Robotic spine surgery and augmented reality systems: a state of the art." Neurospine 17.1 Mar. 31, 2020, 88.

* cited by examiner

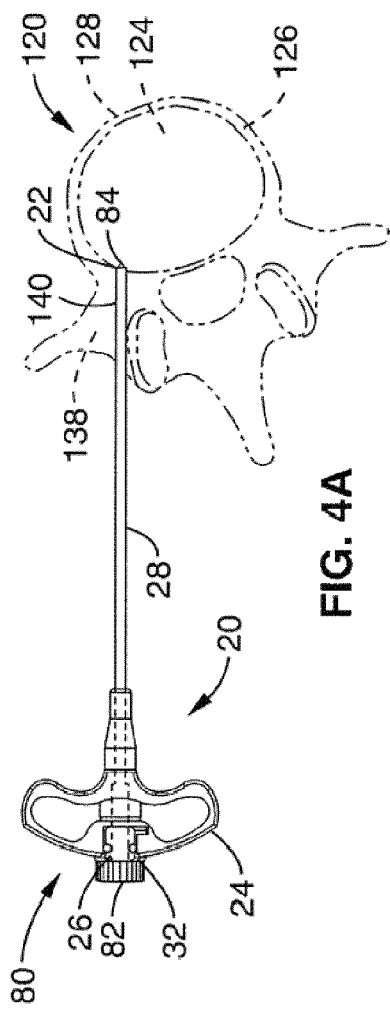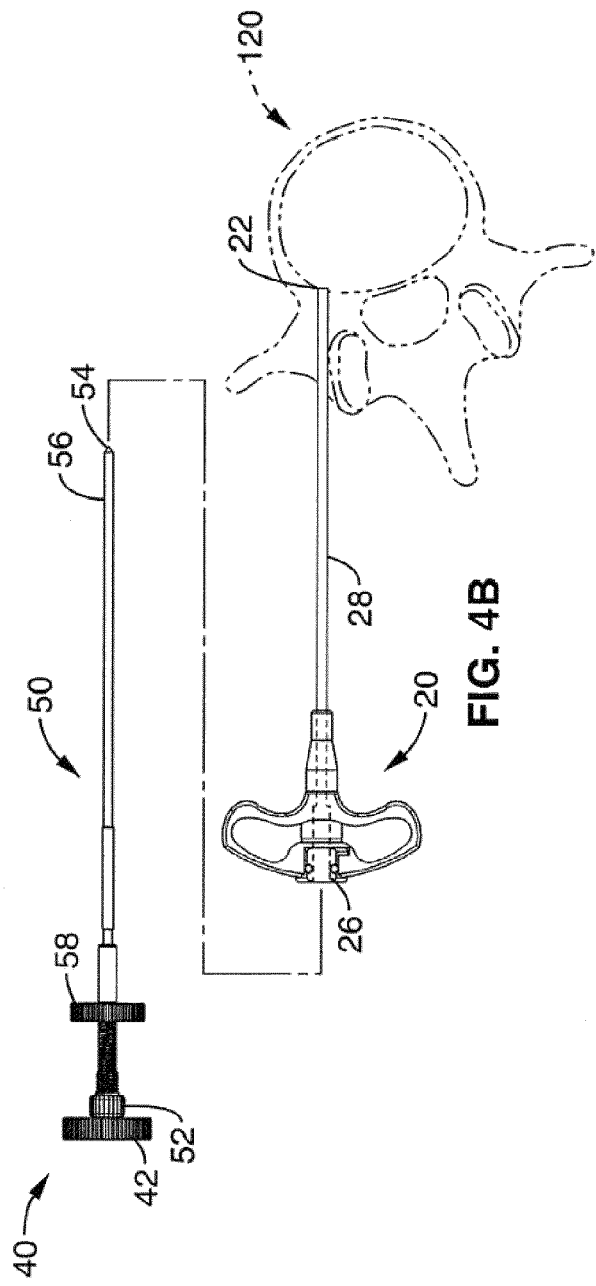
FIG. 4A
FIG. 4B

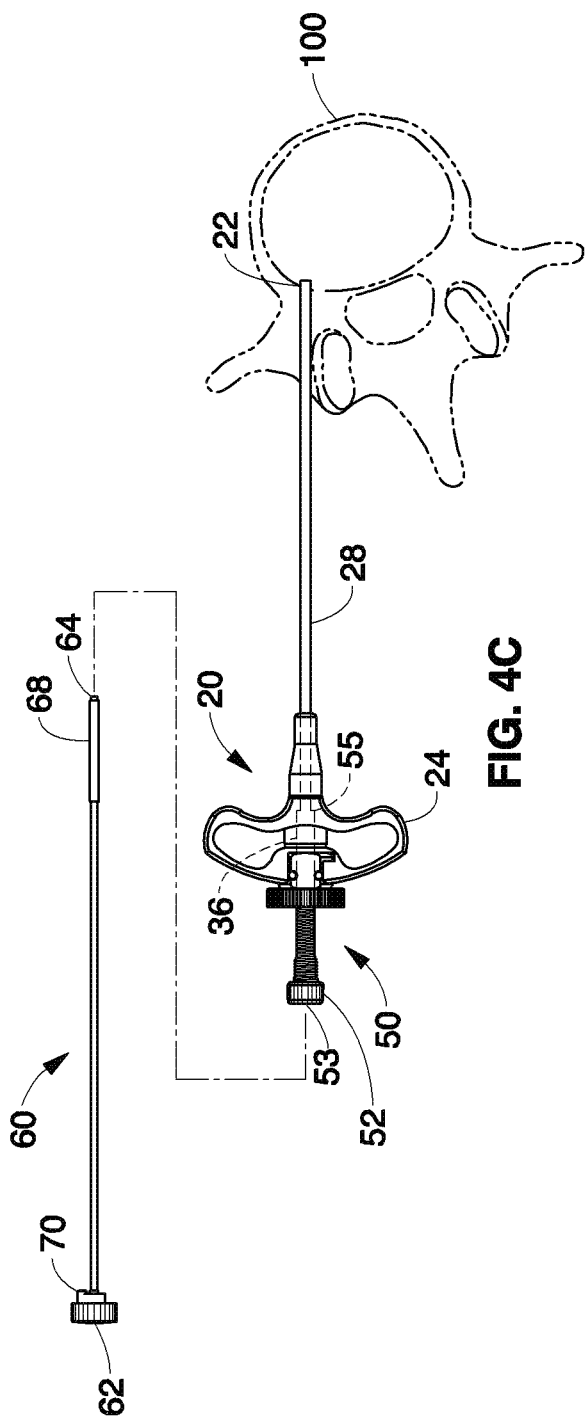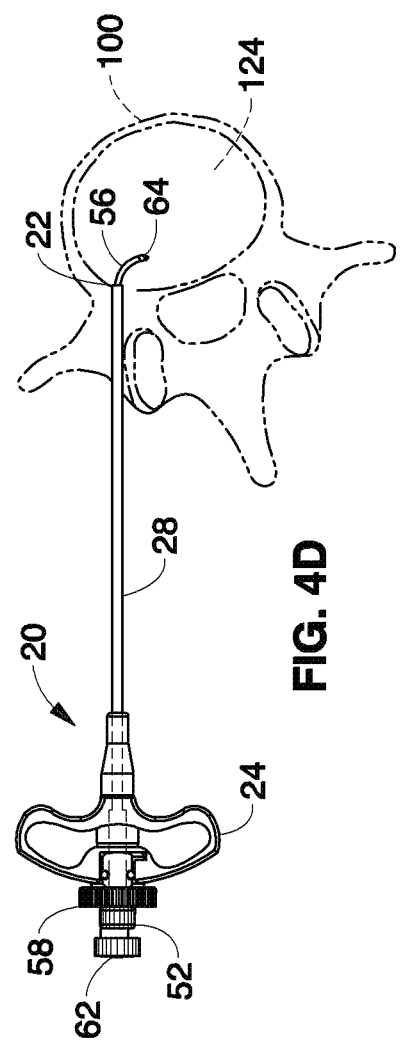
FIG. 4C
FIG. 4D

SYSTEMS FOR ACCESSING NERVES WITHIN BONE

CROSS-REFERENCE TO RELATED APPLICATIONS

This application is a continuation of U.S. patent application Ser. No. 15/040,268, filed on Feb. 10, 2016, issued as U.S. Pat. No. 10,265,099, which is a continuation of U.S. patent application Ser. No. 13/862,242 filed on Apr. 12, 2013, issued as U.S. Pat. No. 9,259,241, which is a continuation of U.S. patent application Ser. No. 12/566,895 filed on Sep. 25, 2009, issued as U.S. Pat. No. 8,419,730, which claims the benefit of U.S. Provisional Application 61/100,553 filed on Sep. 26, 2008, each of which is expressly incorporated in its entirety by reference herein.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to generating passageways through tissue, and more particularly to creating curved paths in bone.

2. Description of Related Art

Recently, the technique of accessing the vertebral body through minimally invasive means has been developed through the surgical techniques used in vertebroplasty and kyphoplasty. Although accessing the vertebral segments of the spine through the pedicle and into the lateral/anterior section of the body of the vertebra is the primary method of placing a treatment device (e.g. a bone cement delivery device and/or an RF probe) into the vertebra, it is difficult to place a probe in the posterior midline section of the vertebra. Furthermore, accessing the posterior midline section of the S1 segment of the spine is difficult with a straight linear access route. A probe preferably needs to be capable of navigating to the posterior section of the S1 vertebral body as well as the same target area within a lumbar vertebral segment. In addition, it is contemplated that spinal segments in the cervical and thoracic spine may also be targeted.

In order to accurately and predictably place a treatment device in the posterior midline section of a lumbar vertebral body or S1 vertebral body, the device or probe needs to navigate to said area through varying densities of bone. However due to the varying densities of bone, it is difficult to navigate a probe in bone and ensure its positioning will be in the posterior midline section of the vertebral body.

Current techniques for tissue aspirations require a coaxial needle system that allows taking several aspirates through a guide needle without repositioning the guide needle. However the problem with this system is that after the first pass of the inner needle in to the lesion, subsequent passes tend of follow the same path within the mass, yielding only blood not diagnostic cells.

A scientific paper written by Kopecky et al., entitled "Side-Exiting Coaxial Needle for Aspiration Biopsy," describes the use of a side exiting coaxial needle to allow for several aspiration biopsies. The guide needle has a side hole 1cm from the distal tip. When a smaller needle is advanced through this new guide needle, the smaller needle is deflected by a ramp inside the guide, causing the smaller needle to exit through the side hole. Although this side exiting needle is able to deflect a bone aspiration needle, it does not guarantee that the needle exits the side hole in a linear direction into the tissue site. Once the tissue aspiration needle exits the needle, it will deviate from a linear path depending on the density of the tissue and inherent material strength of the needle. This is an inherent problem the device is unable to overcome.

Accordingly, an object of the present invention is a system and method for generating a path in bone that predictably follows a predetermined curved path.

BRIEF SUMMARY OF THE INVENTION

The present invention is directed to systems and methods to deploy and navigate a flexible treatment instrument, such as an RF bipolar probe, within bone. Although the systems and methods described below are primarily directed to navigating bone through a vertebral member of the spine, and particularly to treat the BVN of a vertebral member, it is appreciated that the novel aspects of the present invention may be applied to any tissue segment of the body.

The first novel principle of this invention is the ability to navigate a curve or angle within varying densities of cancellous bone and create a straight channel at the end of the navigated curve or angle. Several systems are described.

One aspect is a method of therapeutically treating a vertebral body having an outer cortical bone region and an inner cancellous bone region, and a BVN having a trunk extending from the outer cortical bone region into the inner cancellous region and a branches extending from the trunk to define a BVN junction, comprising the steps of: a) inserting an energy device into the vertebral body, and b) exclusively depositing energy within the inner cancellous bone region of the vertebral body between, but exclusive of the BVN junction and the outer cortical bone region, to denervate the BVN.

In another aspect of the present invention, a tube-within-tube embodiment has a deployable curved Nitinol tube that deploys from a straight cannula. The Nitinol tube is pre-curved to create an angular range of approximately 0° to approximately 180°, but more specifically from approximately 45° to approximately 110°, when fully deployed from the straight cannula. The design of the curve is such that the flexible element (carrying the treatment device) can navigate through the angular range of deployment of the nitinol tube. The curved nitinol tube allows the flexible element to navigate through a curve within bone without veering off towards an unintended direction. Cancellous bone density varies from person to person. Therefore, creating a curved channel within varying density cancellous bone will generally not predictably or accurately support and contain the treatment device as it tries to navigate the curved channel. With the present invention, the flexible element is deployed into the bone through the curved Nitinol tube, which supports the element as it traverses through the curve. When it departs from the tube, it will do so in a linear direction towards the target zone. This design allows the user to predictably and accurately deploy the flexible element towards the target zone regardless of the density of the cancellous bone.

An aspect of the invention is a system for channeling a path into bone. The system comprises a trocar having a central channel and opening at its distal tip, and a cannula sized to be received in said central channel and delivered to said distal opening. The cannula has a deflectable tip with a preformed curve such that the tip straightens while being delivered through the trocar and regains its preformed curve upon exiting and extending past the distal opening of the trocar to generate a curved path in the bone corresponding to the preformed curve of the deflectable tip. The cannula comprises a central passageway having a diameter configured allow a treatment device to be delivered through the central passageway to a location beyond the curved path.

In one embodiment, the system further includes a straight stylet configured to be installed in the trocar, wherein the straight stylet comprises a sharp distal tip that is configured to extend beyond the distal opening of the trocar to pierce the bone as the trocar is being delivered to a treatment location within the bone.

The system may further include a straightening stylet configured to be installed in the cannula, wherein the straightening stylet comprising a rigid construction configured to straighten the distal tip of the cannula when positioned in the trocar.

In an alternative embodiment, the straightening stylet further comprises a sharp distal end to pierce the bone, and the straightening stylet and cannula are installed in the trocar in place of the straight stylet as the trocar is delivered into the bone.

In a preferred embodiment, the system further includes a curved stylet having an outer radius sized to fit within the central passageway of the curved cannula. The curved stylet is configured to be installed in the curved cannula while the curved cannula is extended past the distal opening of the trocar, the curved stylet configured to block the distal opening of the curved cannula while being delivered into the bone. Preferably, the curved stylet has a curved distal end corresponding to the curve of the curved cannula.

The curved stylet also has a sharp distal tip configured to extend past the curved cannula to pierce the bone as the cannula is delivered past the distal opening of the trocar. The curved stylet also preferably comprises an angled distal tip configured to further support and maintain the curved stylet radius as it is delivered past the distal opening of the trocar and into bone.

Preferably, the curved stylet and the curved cannula have mating proximal ends that align the curve of the curved stylet with the curve of the curved cannula.

In one embodiment, the system further includes a straight channeling stylet configured to be installed in the cannula after removing the curved stylet, wherein the straight channeling stylet is flexibly deformable to navigate the curved cannula yet retain a straight form upon exiting the curve cannula, and wherein straight channeling stylet has a length longer than the curved cannula such that it creates a linear path beyond the distal end of the curved cannula when fully extended.

Another aspect is method for channeling a path into bone to a treatment location in the body of a patient. The method includes the steps of inserting a trocar having a central channel and opening at its distal tip into a region of bone at or near the treatment location, and delivering a cannula through said central channel and to said distal opening, wherein the cannula comprises a deflectable tip with a preformed curve such that the tip straightens while being delivered through the trocar and regains its preformed curve upon exiting the trocar, and extending the cannula past the distal opening of the trocar to generate a curved path in the bone corresponding to the preformed curve of the deflectable tip. Finally, a treatment device is delivered through a central passageway in said cannula to the treatment location beyond the curved path.

In one embodiment, inserting a trocar into a region of bone comprises inserting a stylet into the trocar such that the stylet extends beyond the distal opening of the trocar, and inserting the stylet and trocar simultaneously into the region of bone such that the stylet pierces the bone as the trocar is being delivered to a treatment location.

In another embodiment, delivering a cannula through the central channel comprises inserting a straightening stylet into the central passageway of the cannula, wherein the straightening stylet comprises a rigid construction configured to straighten the curved distal tip of the cannula, and inserting the straightening stylet and straightened cannula simultaneously into the trocar.

In an alternative embodiment, the straightening stylet further comprises a sharp distal end to pierce the bone, wherein the straightening stylet and cannula are installed simultaneously along with the trocar as the trocar is delivered into the bone.

In yet another embodiment, extending the cannula past the distal opening is done by inserting a curved stylet into the central passageway of the curved cannula such that a distal tip of the curved stylet extends to at least the distal opening of the curved cannula, and simultaneously extending the curved cannula and curved stylet from the distal end of the trocar such that the curved stylet blocks the distal opening of the curved cannula while being delivered into the bone.

In a preferred embodiment, the curved stylet has a curved distal end corresponding to the curve of the curved cannula, and wherein the curved stylet reinforces the curved shape of the curved cannula as the curved cannula is extended past the distal opening of the trocar. The curved stylet has a sharp distal tip such that it is advanced within the central passageway so that the curved stylet extends past the distal opening of the curved cannula such that the curved stylet pierces the bone as the cannula is delivered past the distal opening of the trocar.

In a further step, the curved stylet is removed from the curved cannula, and a straight channeling stylet is inserted into the curved distal end of the cannula. The straight channeling stylet is flexibly deformable to navigate the curved cannula, yet retain a straight form upon exiting the curved cannula. The straight channeling stylet is longer than the curved cannula to create a linear channel beyond the distal tip of the curved cannula.

In a preferred embodiment, the trocar is inserted through a cortical bone region and into a cancellous bone region of a vertebrae, and the curved cannula is extended though at least a portion of the cancellous bone region to a location at or near the treatment location. A preferred treatment location comprises a BVN of the vertebrae, and treatment is delivered to the treatment location to denervate at least a portion of the BVN. In one embodiment, a portion of the BVN is denervated by delivering focused, therapeutic heating to an isolated region of the BVN. In another embodiment, a portion of the BVN comprises is denervated delivering an agent to the treatment region to isolate treatment to that region. Preferably, the treatment is focused on a location of the BVN that is downstream of one or more branches of the BVN.

Another aspect is a kit for channeling a path into bone. The kit includes a trocar having a central channel and opening at its distal tip, and a cannula selected from a set of cannulas sized to be received in said central channel and delivered to said distal opening. The cannula has a deflectable distal tip with a preformed curve such that the tip straightens while being delivered through the trocar and regains its preformed curve upon exiting and extending past the distal opening of the trocar to generate a curved path in the bone corresponding to the preformed curve of the deflectable tip. The cannula comprises a central passageway having a diameter configured allow a treatment device to be delivered through the central passageway to a location beyond the curved path, wherein the set of cannulas comprises one or more cannulas that have varying preformed curvatures at the distal tip.

In a preferred embodiment, the one or more cannulas have a varying preformed radius at the distal tip. In addition, the one or more cannulas each have distal tips that terminate at varying angles with respect to the central channel of the trocar. The length of the distal tips may also be varied. The angle of the distal with respect to the central channel of the trocar may vary from 0 degrees to 180 degrees.

The kit may further include a straight stylet configured to be installed in the trocar, the straight stylet comprising a sharp distal tip that is configured to extend beyond the distal opening of the trocar to pierce the bone as the trocar is being delivered to a treatment location within the bone.

In a preferred embodiment, the kit includes a set of curved stylets having an outer radius sized to fit within the central passageway of the curved cannula, wherein each curved stylet is configured to be installed in the curved cannula while the curved cannula is extended past the distal opening of the trocar. The curved stylet is configured to block the distal opening of the curved cannula while being delivered into the bone. Each curved stylet has a varying curved distal end corresponding to the curve of a matching curved cannula in the set of curved cannulas. The curved stylet has a sharp distal tip configured to extend past the curved cannula to pierce the bone as the cannula is delivered past the distal opening of the trocar.

In another embodiment, the kit includes a set of straight channeling stylets wherein one of the set of stylets is configured to be installed in the cannula after removing the curved stylet. The straight channeling stylet is flexibly deformable to navigate the curved cannula yet retain a straight form upon exiting the curve cannula. Each of the straight channeling stylets has a varying length longer than the curved cannula such that the straight channeling stylet creates a predetermined-length linear path beyond the distal end of the curved cannula when fully extended.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIGS. 4A-F illustrate a method for accessing the BVN with the system of the present invention.

Figure 5:
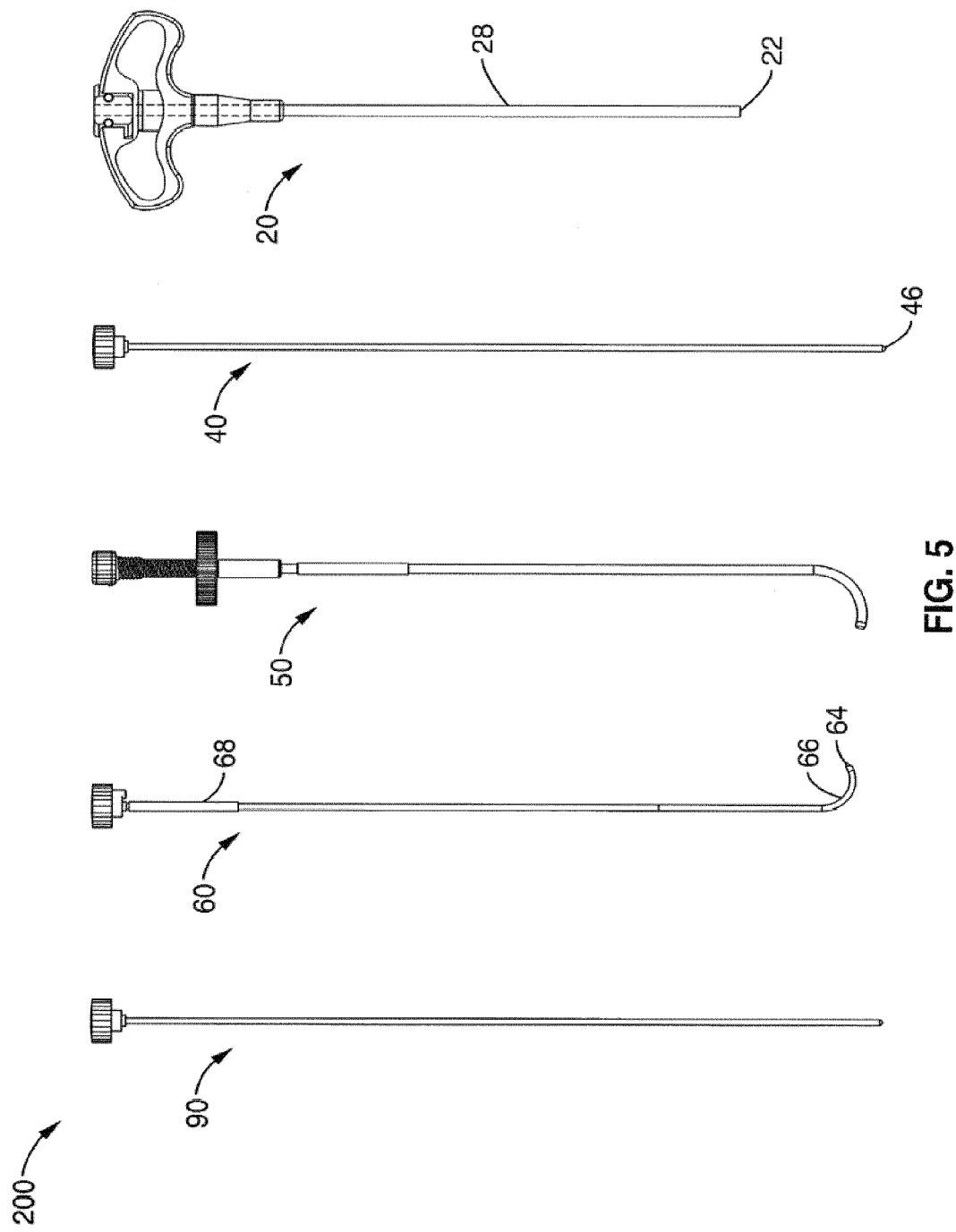

FIG. 5 shows an alternative system for generating a curved path in bone according to the present invention.

Figure 6:
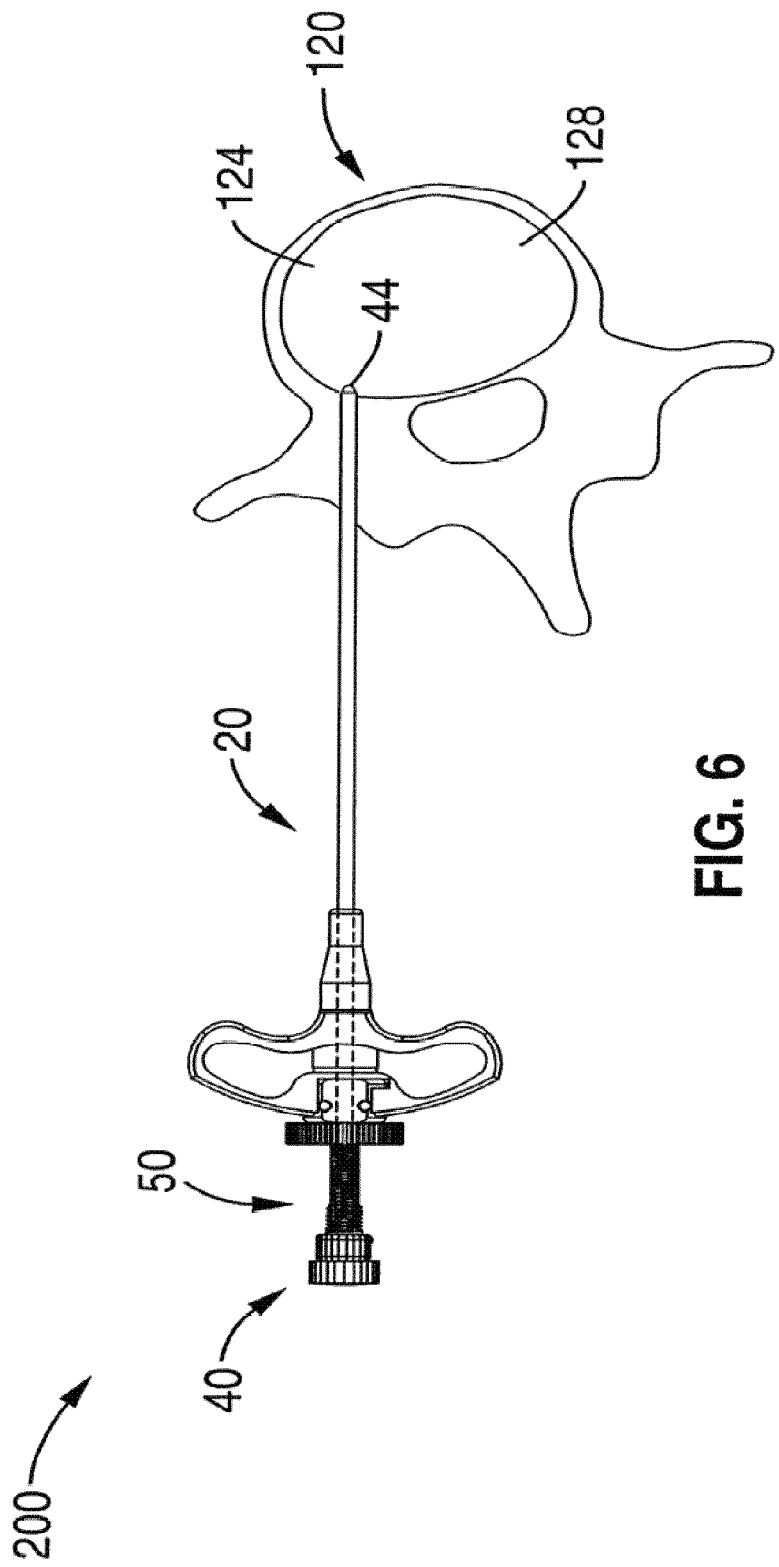

FIG. 6 shows the system of FIG. 5 being installed in a vertebral body.

Figure 7B:
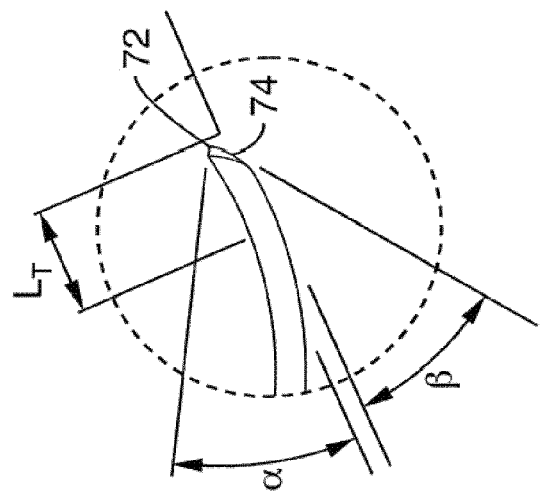
Figure 7A:
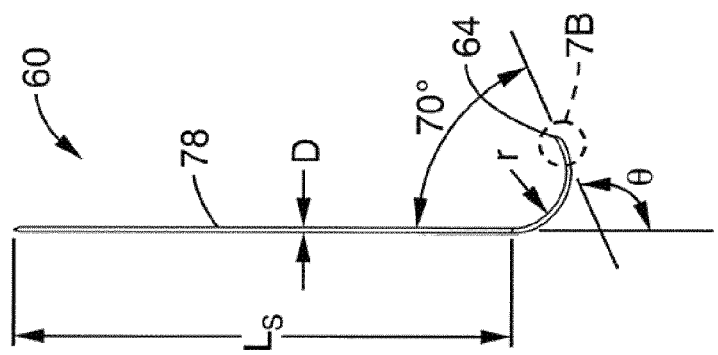

FIGS. 7A-7B show a curved stylet in accordance with the present invention.

DETAILED DESCRIPTION OF THE INVENTION

Referring more specifically to the drawings, for illustrative purposes the present invention is embodied in the apparatus generally shown in FIG. 1 through FIG. 7B. It will be appreciated that the apparatus may vary as to configuration and as to details of the parts, and that the method may vary as to the specific steps and sequence, without departing from the basic concepts as disclosed herein.

Figure 1:
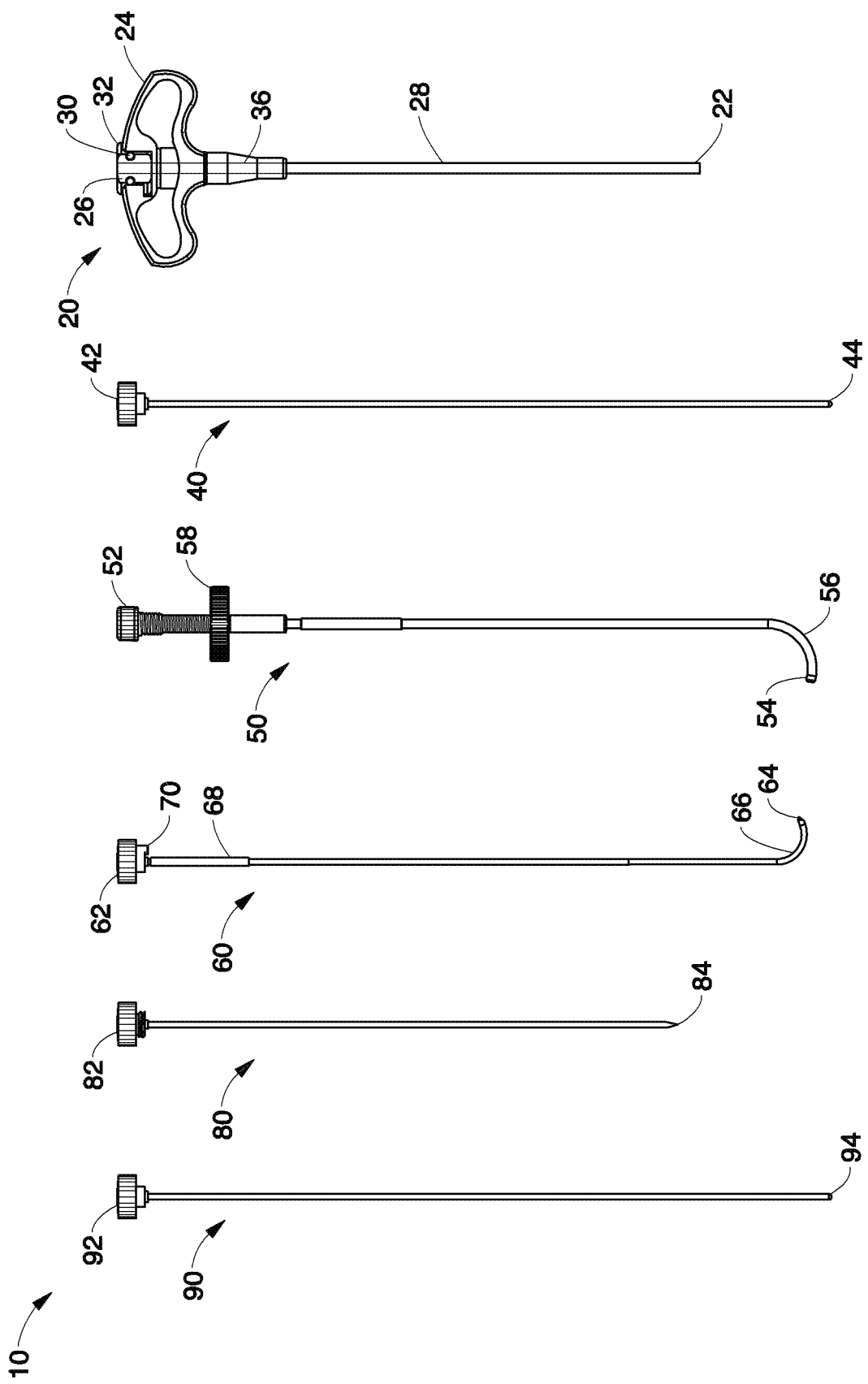
FIG. 1 is a system for generating a curved path in bone according to the present invention.
Figure 2:
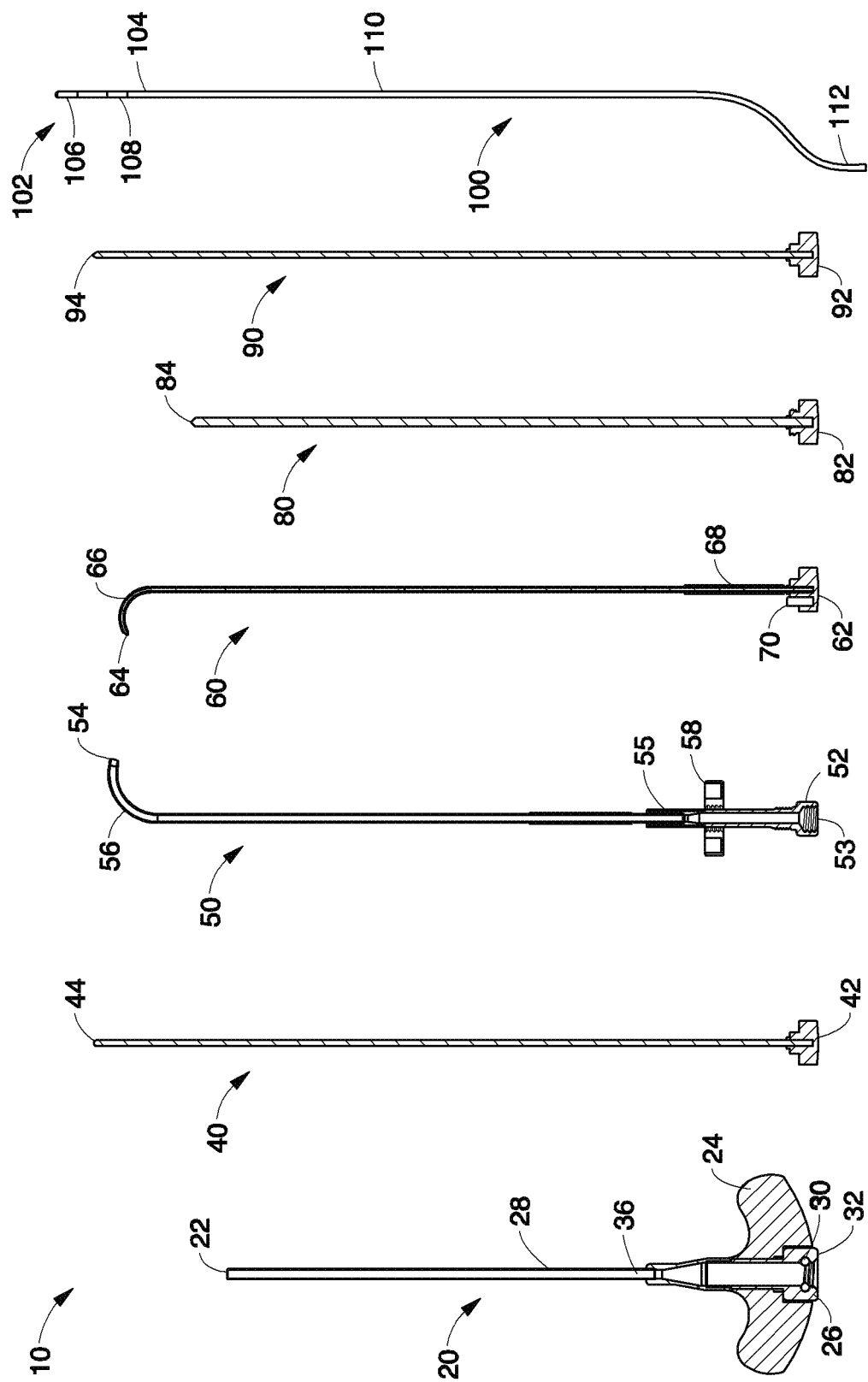
FIG. 2 is a sectional view of the system of FIG. 1

FIGS. 1 and 2 illustrate a first embodiment of the present invention comprising a system or kit 10 for forming a path through bone. The system comprises a needle trocar 20 (the main body of the instrument set). The trocar 20 comprises an elongate shaft 28 having a handle 24 at its proximal end 32 and a central lumen 36 passing through to the distal end 22 of the trocar 20. The central lumen 36 is generally sized to allow the other instruments in the system 10 to be slideably introduced into the patient to a treatment region. System 10 further comprises a straight stylet 80 having a sharp-tipped needle 84 at its distal end that is used with the needle trocar 20 to create the initial path through the soft tissue and cortical shell to allow access to the cancellous bone, a curved cannula 50 that is used to create/maintain the curved path within the bone/tissue. A straightening stylet 40 is used to straighten out the curve and load the curved cannula 50 into the needle trocar 20. A curved stylet 60 is used in conjunction with the curved cannula 50 to create the curved path within the bone/tissue, and a channeling stylet 90 is used to create a working channel for a treatment device (such as RF probe 100) beyond the end of the curved path created by the curved cannula 50.

The surgical devices and surgical systems described may be used to deliver numerous types of treatment devices to varying regions of the body. Although the devices and systems of the present invention are particularly useful in navigating through bone, it is appreciated that they may also be used to navigate through soft tissue, or through channels or lumens in the body, particularly where one lumen may branch from another lumen.

The following examples illustrate the system 10 applied to generating a curve bone path in the vertebral body, and more particularly for creating a bone path via a transpedicular approach to access targeted regions in the spine. In particular, the system 10 may be used to deliver a treatment device to treat or ablate intraosseous nerves, and in particular that basivertebral nerve (BVN). Although the system and methods provide significant benefit in accessing the BVN, it is appreciated that the system 10 of the present invention may similarly be used to create a bone path in any part of the body.

Figure 3:
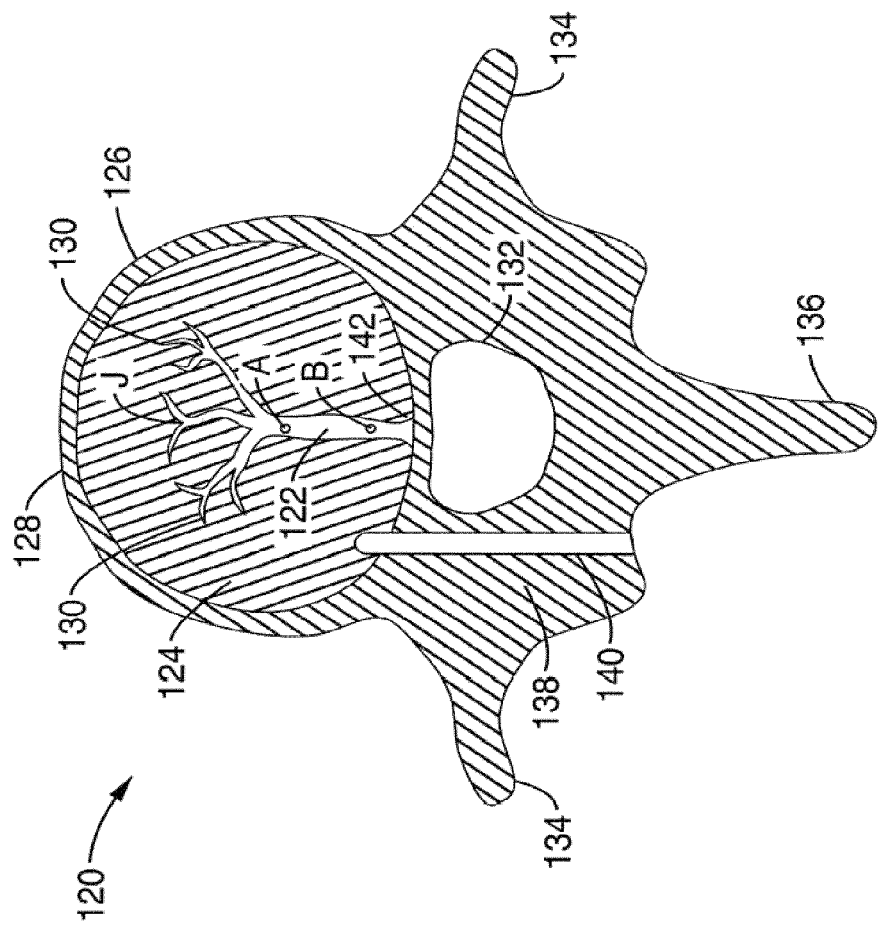
FIG. 3 illustrates a sectioned view of a vertebral body with a path bored through the cortical shell.

FIG. 3 illustrates a cross-sectional view of a vertebra 120. Recently, the existence of substantial intraosseous nerves 122 and nerve branches 130 within human vertebral bodies ("basivertebral nerves") have been identified. The basivertebral nerve 122 has at least one exit 142 point at a location along the nerve 122 where the nerve 122 exits the vertebral body 126 into the vertebral foramen 132.

Preferably, the basivertebral nerves are at, or in close proximity to, the exit point 142. Thus, the target region of the BVN 122 is located within the cancellous portion 124 of the bone (i.e., to the interior of the outer cortical bone region 128), and proximal to the junction J of the BVN 122 having a plurality of branches 130 (e.g. between points A and B along nerve 122). Treatment in this region is advantageous because only a single portion of the BVN 122 need be effectively treated to denervate or affect the entire system. Typically, treatment in accordance with this embodiment can be effectuated by focusing in the region of the vertebral body located between 60% (point A) and 90% (point B) of the distance between the anterior and posterior ends of the vertebral body. In contrast, treatment of the BVN 122 in locations more downstream than the junction J require the denervation of each branch 130.

In one approach for accessing the BVN, the patient's skin is penetrated with a surgical instrument which is then used to access the desired basivertebral nerves, i.e., percutaneously. In one embodiment, a transpedicular approach is used for penetrating the vertebral cortex to access the BVN 122. A passageway 140 is created between the transverse process 134 and spinous process 136 through the pedicle 138 into the cancellous bone region 124 of the vertebral body 126 to access a region at or near the base of the nerve 122. It is appreciated that a postereolateral approach (not shown) may also be used for accessing the nerve.

FIGS. 4A-F illustrate a preferred method for accessing the BVN with the system 10 of the present invention. First, the straight stylet 80 is inserted in aperture 26 at the proximal end 32 of needle trocar 20. The straight stylet 80 is advanced down the central lumen 36 (see FIG. 2) of the trocar 20 until the proximal stop 82 abuts against handle 24 of the trocar 20, at which point the distal tip 84 of straight stylet protrudes out of the distal end 22 of the trocar 20. The tip 84 of the straight stylet 80 preferably comprises a sharp tip for piercing soft tissue and bone.

Referring now to FIG. 4A, the assembly (trocar 20 and straight stylus 80) is advanced through soft tissue to the surface of the bone. Once the proper alignment is determined, the assembly is advanced through the cortical shell of pedicle 138 and into the cancellous interior 124 of the bone.

After the proper depth is achieved, the straight stylet 80 is removed from the trocar 20, while the trocar 20 remains stationary within the vertebrae 120. The straightening stylet 40 is inserted into proximal aperture 53 (see FIG. 2) of the curved cannula 50 and advanced along the central lumen of the curved cannula 50 until the stop 42 of the stylet 40 abuts up to the proximal end 52 of the curved cannula. This forces the distal tip of the straight stylet through the curved section 56 of the curved cannula 50 to straighten out the curved section 56. It is contemplated that the straight stylet comprise a hard, non-compliant material and the distal end of the curved cannula 50 a compliant, yet memory retaining material (e.g. Nitinol, formed PEEK, etc.) such that the curved section 56 yields to the rigidity of the straightening stylet 40 when installed, yet retains its original curved shape when the stylet 40 is removed.

As shown in FIG. 4B, once the straightening stylet 40 is secure and the curved cannula 50 is straight, they are inserted into the needle trocar 20 and secured. Proper alignment (e.g. prevent rotation, orient curve direction during deployment) is maintained by aligning a flat on the upper portion 58 of the curved cannula 50 to an alignment pin secured perpendicularly into the needle trocar 20 handle 24. Once the curved cannula 50 is secure, the straightening stylet 40 is removed, while the curved cannula 50 remains stationary within the trocar 20.

Referring to FIG. 4C, the curved stylet 60 is then straightened out by sliding the small tube 68 proximally to distally on its shaft towards the distal tip 64 or from the distal tip 64 proximally on its shaft towards the proximal end 62. Once the curved distal tip 66 is straightened out and fully retracted inside the small tube 68, the curved stylet 60 is inserted into the proximal aperture 53 of the curved cannula 50, which still resides inside the needle trocar 20. As the curved stylet 60 is advanced into the curved cannula 50, the small tube 68 is met by a stop 55 (see FIG. 4C). As the curved stylet 60 continues to advance the small tube 68 is held inside the handle of the curved cannula 50. This allows the curve of the stylet 60 to be exposed inside the curved cannula 50. To create the maximum force the curve of the two parts (50 & 60) must be aligned. To ensure alignment the cap on the curved stylet 60 has an alignment pin 70 which engages with an alignment notch on the proximal end 52 of the curved cannula 50.

Once the stylet 60 is fully seated and aligned with the curved cannula 50 the tip of the curved stylet 60 will protrude from the tip of the curved cannula 50 by about 1/16 to 3/16 inches. This protrusion will help to drive the curve in the direction of its orientation during deployment.

Referring now to FIG. 4D, with the curved stylet 60 and the curved cannula 50 engaged, the locking nut 58 at the top of the curved cannula 50 is rotated counter clockwise to allow the cannula 50 and curved stylet 60 to be advanced with relation to the needle trocar 20 such that the proximal end 52 abuts against 58, advancing the curved cannula 50 and curved stylet 60 beyond the distal opening of trocar 20 to generate a curved path in the cancellous bone region 124. As the curved cannula 50 and curved stylet 60 are advanced they will preferably curve at a radius of 0.4 to 1.0 inches through cancellous bone and arc to an angle between 5 and 110 degrees. Once the curved cannula 50 and curved stylet 60 are deployed to the intended angle, the locking nut at the top of the curved cannula 50 is engaged with the needle trocar 20 to stop any additional advancement of the curved stylet cannula assembly.

FIGS. 7A-7B illustrate the tip of the curved stylet 60, which has been formed with two angles. To help the curve deployment in the proper direction the curved section 66 of the curved stylet 60 is shaped in a predetermined orientation. The angle on the inside of the curve 72 is less than the angle on the outside of the curve 74. This disparity in angle helps the stylet cannula assembly 50 & 60 curve in the bone as bone pushes against outside curve face 74 ensuring the curve radius is maintained during deployment.

Figure 4E:
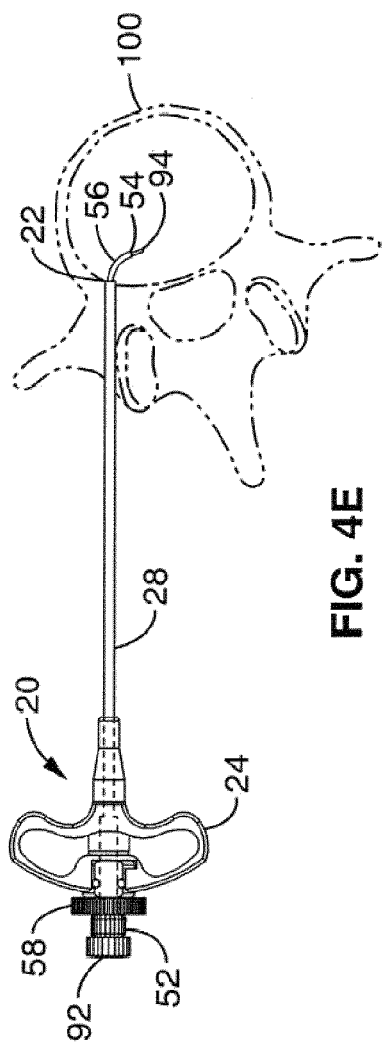

Referring now to FIG. 4E, the curved stylet 60 is then removed and replaced by the channeling stylet 90. The tip 94 of the channeling stylet 90 is advanced beyond the end 54 of the curved cannula 50 towards the intended target treatment zone.

Figure 4F:
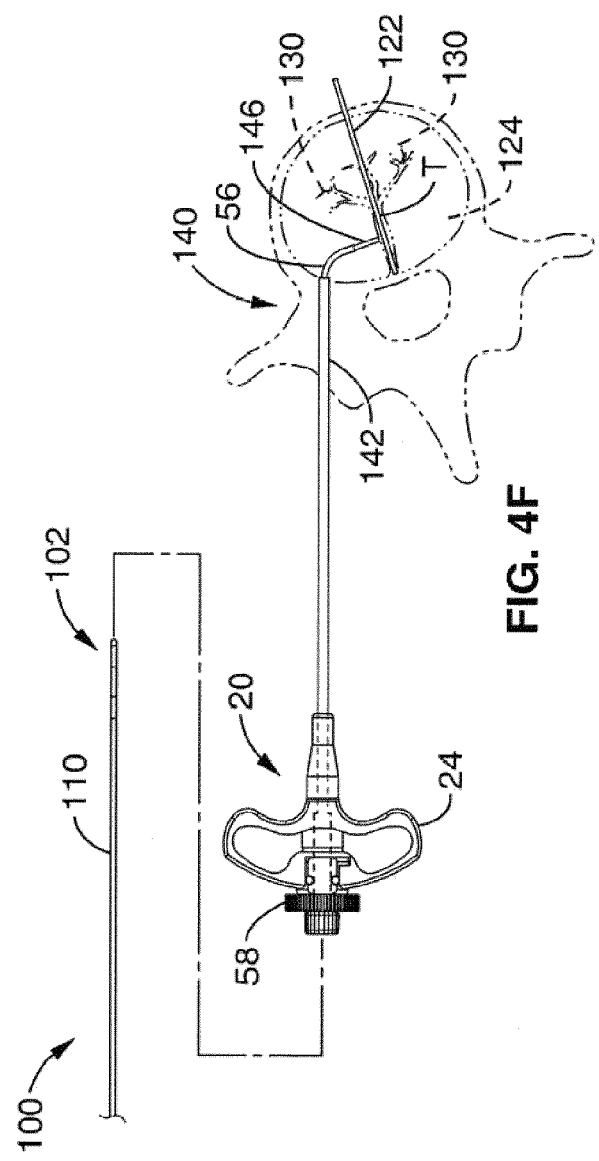

Referring now to FIG. 4F, once the channeling stylet 90 reaches the target treatment zone, it is removed creating a working channel 146. Channel 140 will generally have a first section 142 that crosses the cortical bone of the pedicle 138, followed by a curved path 144. These sections are occupied by curved cannula 50 such that a treatment device fed through the cannula 50 will have to follow the curve of the cannula 50 and not veer off in another direction. The channel may further comprise the linear extension 146 in the cancellous bone 124 to further advance the treatment device toward the treatment site T.

With the trocar 20 and curved cannula 50 still in place, a treatment device (e.g. treatment probe 100 shown in FIG. 2, with an active element 102 on the distal end 104 of elongate flexible catheter 110 is delivered to the target treatment location T to perform a localized treatment.

In a preferred embodiment, the active element 102 is delivered to the treatment site and activated to delivery therapeutic treatment energy. The treatment probe may comprise an RF delivery probe having bipolar electrodes 106 and 108 that deliver a therapeutic level of heating to stimulate or ablate the nerve 122.

It is appreciated that any number of treatment modalities may be delivered to the treatment site for therapeutic treatment. For example, treatment may be affected by monopolar or tripolar RF, ultrasound, radiation, steam, microwave, laser, or other heating means. Additionally, the treatment device may comprise a fluid delivery catheter that deposits an agent, e.g. bone cement, or other therapeutic agent, to the treatment site T. Alternatively, cryogenic cooling may be delivered for localized treatment of the BVN. Furthermore, treatment may be affected by any mechanical destruction and or removal means capable of severing or denervating the BVN. For example, a cutting blade, bur or mechanically actuated cutter typically used in the art of orthoscopic surgery may be used to affect denervation of the BVN.

In addition to or separate from treating the BVN, a sensor may be delivered to the region to preoperatively or postoperatively measure nerve conduction at the treatment region. In this configuration, the sensor may be delivered on a distal tip of a flexible probe that may or may not have treatment elements as well.

The goal of the treatment may be ablation, or necrosis of the target nerve or tissue, or some lesser degree of treatment to denervate the BVN. For example, the treatment energy or frequency may be just sufficient to stimulate the nerve to block the nerve from transmitting signal (e.g. signals indicating pain).

Once the treatment is complete, the probe 100 is withdrawn. The curved cannula 50 is then withdrawn into the needle trocar 20. The needle trocar 20 with the curved cannula 50 is then removed and the access site is closed as prescribed by the physician.

In the above system 10, the design of the curved sections 56 and 66 of the curved cannula 50 and curved stylet 60, respsectively, is such that the flexible element (e.g. carrying the treatment device) can navigate through the angular range of deployment of the Nitinol tube of the curved cannula 50. The curved nitinol tube of the curved cannula 50 allows the flexible element to navigate through a curve within bone without veering off towards an unintended direction. Cancellous bone density varies from person to person. Therefore, creating a curved channel within varying density cancellous bone 124 will generally not predictably or accurately support and contain the treatment device as it tries to navigate the curved channel.

With the system 10 of the present invention, the treatment device 100 is deployed into the bone through the curved Nitinol tube of the curved cannula 50, which supports the element as it traverses through the curve. When it departs from the tube, it will do so in a linear direction along path 146 towards the target zone. This allows the user to predictably and accurately deploy the treatment device towards the target zone T regardless of the density of the cancellous bone.

In some embodiments, a radius of curvature that is smaller than that which can be achieved with a large diameter Nitinol tube may be advantageous. To achieve this, the curved tube of the curved cannula 50 may take one of several forms. In one embodiment, the tube 50 is formed from a rigid polymer that can be heat set in a particular curve. If the polymer was unable to hold the desired curve, an additional stylet (e.g. curved stylet 60) of Nitinol, or other appropriate material, may also be used in conjunction with the polymer tube to achieve the desired curve. This proposed combination of material may encompass and number or variety of materials in multiple different diameters to achieve the desired curve. These combinations only need to ensure that the final outside element (e.g. trocar 20) be "disengageable" from the internal elements and have an inner diameter sufficient to allow the desired treatment device 100 to pass to the treatment region T.

In an alternative embodiment, of the curved cannula 50 may comprise a Nitinol tube having a pattern of reliefs or cuts (not shown) in the wall of the tube (particularly on the outer radius of the bend). The pattern of cuts or reliefs would allow the tube to bend into a radius tighter than a solid tube could without compromising the integrity of the tubing wall.

FIG. 5 illustrates a second embodiment of the system or kit 200 of the present invention that may be used to reduce the number of steps required for the procedure. The second embodiment includes a needle trocar 20, straightening stylet 40, used with the needle trocar 20 and the curved cannula 50 to create the initial path through the soft tissue and cortical shell to allow access to the cancellous bone, curved stylet 60 used in conjunction with the curved cannula 50 to create the curved path within the bone/tissue, and channeling stylet 90 used to create a working channel for the probe beyond the end of the curved path created by the curved stylet.

In one method according to the present invention, the straightening stylet 40 is inserted into the curved cannula 50 and secured. In this embodiment, the straightening stylet 40 has a sharp tip 46 designed to penetrate bone. Once the straightening stylet 40 is secure and the curved cannula 50 is straight, they are inserted into the needle trocar 20 and secured. In this embodiment, the curved cannula 50 and straightening stylet 40 are inserted into the shaft 28 of the trocar 20 only as far as to have sharp tip 46 of the straightening stylet 40 protrude from the distal end 22 of the trocar 20. Proper alignment is maintained by aligning a flat on the upper portion of the curved cannula 50 with a pin secured perpendicularly into the needle trocar 20 handle.

Referring now to FIG. 6, once the curved cannula 50 is secure, the assembly (trocar 20, curved cannula 50, and straightening stylet 40) is advanced through soft tissue to the surface of the bone. After finding the proper alignment at the pedicle 138 of vertebrae 120, the assembly (trocar 20, curved cannula 50, and straightening stylet 40) is advanced through the cortical shell 128 and into the cancellous interior 124 of the bone.

After the proper depth is achieved, the straightening stylet 40 is removed. The curved stylet 60 is then straightened out by sliding the small tube 68 on its shaft towards the distal tip 64. The curved distal tip 66 is straightened out and fully retracted inside the small tube 68, and then the curved stylet 60 is inserted into the curved cannula 50 which still resides inside the needle trocar 20. Once the curved stylet 60 is inserted into the curved cannula 50, the small tube 68 is met by a stop 55 (see FIG. 4C). As the curved stylet 60 continues to advance, the small tube 68 is held inside the handle of the curved cannula 50. This allows the curve of the stylet 60 to be exposed inside the curved cannula 50.

To create the maximum force, it is preferred that the curve of the two parts (50 & 60) are aligned. To ensure alignment the cap on the curved stylet 60 has an alignment pin, which engages with a notch on the top of the curved cannula 50.

When the stylet 60 is fully seated and aligned with the curved cannula 50, the tip of the curved stylet 60 will protrude from the tip of the curved cannula 50 by about 1/16 to 3/16 inches. This protrusion will help to drive the curved cannula 50 in the direction of its orientation during deployment. Once the curved stylet 60 and the curved cannula 50 are engaged, the lock nut at the top of the curved cannula 50 is rotated counter clockwise to allow the cannula 50 and stylet 60 to be advanced with relation to the needle trocar 20 (as shown in FIG. 4D). As the curved cannula and stylet are advanced they generate a curved path toward the treatment location T. Once the curved cannula 50 and stylet 60 are deployed to the intended angle, the lock nut at the top of the curved cannula 50 is engaged with the needle trocar 20 to stop any additional advancement of the curved stylet cannula assembly.

The curved stylet 60 is then removed and replaced by the channeling stylet 90. The channeling stylet 90 is advanced beyond the end of the curved cannula 50 (see FIG. 4E) towards the intended target treatment zone creating a working channel for the active element to be inserted. Once the channeling stylet 80 reached the target treatment zone it is removed and replaced by the treatment device 100, which is delivered to the treatment site T and activated.

Once the treatment is complete, the treatment device 100 is withdrawn. The curved cannula 50 is then withdrawn into the needle trocar 20. The needle trocar 20 with the curved cannula 50 is then removed and the access site is closed as prescribed by the physician.

FIGS. 7A and 7B illustrate detail views of a Nitinol wire for the curved stylet 60 (proximal end not shown). The wire comprises a shaft 78 having constant diameter D and a length $L_s$ that may vary according to the application and desired depth to the treatment location. The wire has a preformed distal tip that is curved to have a radius r that redirects the distal tip 64 at an angle $\Theta$ with the shaft. As shown in FIG. 7A, angle $\Theta$ is shown to be approximately 110°. However, it is appreciated that the preformed tip may have an angle ranging from a few degrees (slight deflection off axis), to up to 180° (e.g. directing back toward the proximal end).

As shown in FIG. 7B detailing the distal tip 64, the tip may have a distal extension $L_T$ that extends away from the shaft 78. To promote channeling along a path that follows radius r, the distal tip 64 is configured with a dual-plane bevels 74 and 72. Plane 74 is offset at angle $\beta$, and plane 72 is offset at angle $\alpha$. This configuration of the leading-allows for the stylet and/or curved cannula to travel through bone in a path correlating to the specified curve in the stylet and/or cannula.

In the example illustrated in FIGS. 7A and 7B, the curved stylet 60 has a shaft length $L_s$ of approximately 3.6 in., diameter D of approximately 0.040 in., and a distal tip length $L_T$ of 0.125 in., radius r of 0.40 in., and angle $\beta=35°$ and angle $\alpha=31°$. It should be noted that the above dimensions are for illustration only, and may vary depending on the anatomy an tissue type.

It is appreciated that all the above embodiments may be provided as a kit of instruments to treat different regions of the body. For example, the location, orientation and angle of the treatment device with respect to the trocar 20 may be varied by providing a set of instruments at varying increments. This may be achieved by varying the curvature (56, 66) in the curved cannula 50 and curved stylet 60. The curvature may be varied by varying the radius of curvature r, the insertion depth (shaft length $L_s$ and tip length $L_T$, and/or the final exit angle $\Theta$ with respect to the trocar 20 central bore. Thus, the physician may select a different kit for treating a lumber spine segment as opposed to a cervical spine segment, as the anatomy will dictate the path that needs to be channeled.

Thus, when treating different spine segments, a set out of the kit may be selected to match the vertebra (or other region being treated). For example, delivering the treatment device at or near the BVN junction for a lumbar vertebra may have a different angle than for a cervical vertebra, and may vary from patient to patient. The set may be selected from the kit intra-operatively, or from a pre-surgery diagnostic evaluation (e.g. radiographic imaging of the target region).

It is appreciated that each of the instruments in the embodiments 100 and 200 detailed above may have any length, shape, or diameter desired or required to provide access to the treatment region (e.g. intraosseous nerve trunk) thereby facilitating effective treatment of the target region. For example, the size of the intraosseous nerve to be treated, the size of the passageway in the bone (e.g. pedicle 138) for accessing the intraosseous nerve, and the location of the bone, and thus the intraosseous nerve, are factors that that may assist in determining the desired size and shape of the individual instruments.

The systems 100, 200 described above may be used with a number of different treatment modalities for therapeutic treatment of the target region. For example, in one embodiment, it is desirable to operate the treatment device 100 in a manner that ablates the tissue of the target region (e.g. BVN) to produce as described in U.S. Pat. No. 6,699,242, herein incorporated by reference in its entirety.

In another embodiment, the treatment device is configured to deliver therapeutic treatment that is targeted to block nerve conduction without ablating the nerve, i.e. thermal treatment is delivered to the nerve (e.g. via thermal therapy, agent or the like) that results in denervation of the BVN without necrosis of tissue. This may be achieved via delivery of a lesser amount of energy or agent to the tissue site (either in the form of less exposure time, concentration, intensity, etc.) than is required for ablation, but an amount sufficient to achieve some amount of temporary or permanent denervation.

As can be seen, therefore, the present invention includes the following inventive embodiments among others:

1. A system for channeling a path into bone, comprising: a trocar having a central channel and opening at its distal tip; and a curved cannula sized to be received in said central channel and delivered to said distal opening; the curved cannula having a deflectable tip with a preformed curve such that the tip straightens while being delivered through the trocar and regains its preformed curve upon exiting and extending past the distal opening of the trocar to generate a curved path in the bone corresponding to the preformed curve of the deflectable tip; wherein the curved cannula comprises a central passageway having a diameter configured allow a treatment device to be delivered through the central passageway to a location beyond the curved path.

2. A system as recited in embodiment 2, further comprising: a straight stylet configured to be installed in the trocar; the straight stylet comprising a sharp distal tip that is configured to extend beyond the distal opening of the trocar to pierce the bone as the trocar is being delivered to a treatment location within the bone.

3. A system as recited in embodiment 2, further comprising: a straightening stylet configured to be installed in the curved cannula; the straightening stylet comprising a rigid construction configured to straighten the distal tip of the curved cannula when positioned in the trocar.

4. A system as recited in embodiment 3, wherein the straightening stylet further comprises a sharp distal end to pierce the bone; and wherein the straightening stylet and curved cannula are configured to be installed in the trocar in place of the straight stylet as the trocar is delivered into the bone.

5. A system as recited in embodiment 1, further comprising: a curved stylet having an outer radius sized to fit within the central passageway of the curved cannula; wherein the curved stylet is configured to be installed in the curved cannula while the curved cannula is extended past the distal opening of the trocar, the curved stylet configured to block the distal opening of the curved cannula while being delivered into the bone.

6. A system as recited in embodiment 5, wherein the curved stylet has a curved distal end corresponding to the curve of the curved cannula.

7. A system as recited in embodiment 5, wherein the curved stylet has a sharp distal tip configured to extend past the curved cannula to pierce the bone as the cannula is delivered past the distal opening of the trocar.

8. A system as recited in embodiment 7, wherein the curved stylet and the curved cannula have mating proximal ends that align the curve of the curved stylet with the curve of the curved cannula.

9. A system as recited in embodiment 5, further comprising a straight channeling stylet configured to be installed in the cannula after removing the curved stylet; wherein the straight channeling stylet is flexibly deformable to navigate the curved cannula yet retain a straight form upon exiting the curve cannula; wherein straight channeling stylet has a length longer than the curved cannula such that it creates a linear path beyond the distal end of the curved cannula when fully extended.

10. A method for channeling a path into bone to a treatment location in the body of a patient, comprising: inserting a trocar into a region of bone near the treatment location; the trocar having a central channel and opening at its distal tip; and delivering a cannula through said central channel and to said distal opening; wherein the cannula comprises a deflectable tip with a preformed curve such that the tip straightens while being delivered through the trocar and regains its preformed curve upon exiting; extending the cannula past the distal opening of the trocar to generate a curved path in the bone corresponding to the preformed curve of the deflectable tip; delivering a treatment device through a central passageway in said cannula having to the treatment location beyond the curved path.

11. A method as recited in embodiment 10, wherein inserting a trocar into a region of bone comprises inserting a stylet into the trocar such that the stylet extends beyond the distal opening of the trocar; and inserting the stylet and trocar simultaneously into the region of bone such that the stylet pierces the bone as the trocar is being delivered to a treatment location.

12. A method as recited in embodiment 10, wherein delivering a cannula through the central channel comprises: inserting a straightening stylet into the central passageway of the cannula; the straightening stylet comprising a rigid construction configured to straighten the curved distal tip of the cannula; and inserting the straightening stylet and straightened cannula simultaneously into the trocar.

13. A method as recited in embodiment 12, wherein the straightening stylet further comprises a sharp distal end to pierce the bone; and wherein the straightening stylet and cannula are installed simultaneously along with the trocar as the trocar is delivered into the bone.

14. A method as recited in embodiment 10, wherein extending the cannula past the distal opening comprises: inserting a curved stylet into the central passageway of the curved cannula such that a distal tip of the curved stylet extends to at least the distal opening of the curved cannula; simultaneously extending the curved cannula and curved stylet from the distal end of the trocar such that the curved stylet blocks the distal opening of the curved cannula while being delivered into the bone.

15. A method as recited in embodiment 14, wherein the curved stylet has a curved distal end corresponding to the curve of the curved cannula; and wherein the curved stylet reinforces the curved shape of the curved cannula as the curved cannula is extended past the distal opening of the trocar.

16. A method as recited in embodiment 14, wherein the curved stylet has a sharp distal tip; wherein curved stylet is advanced within the central passageway so that the curved stylet extends past the distal opening of the curved cannula such that the curved stylet pierces the bone as the cannula is delivered past the distal opening of the trocar.

17. A method as recited in embodiment 14, further comprising: removing the curved stylet from the curved cannula; inserting a straight channeling stylet into the curved distal end of the cannula; wherein the straight channeling stylet is flexibly deformable to navigate the curved cannula yet retain a straight form upon exiting the curved cannula; wherein the straight channeling stylet is longer than the curved cannula to create a linear channel beyond the distal tip of the curved cannula.

18. A method as recited in embodiment 10, wherein the trocar is inserted through a cortical bone region and into a cancellous bone region of a vertebrae, and wherein the curved cannula is extended though at least a portion of the cancellous bone region to a location at or near the treatment location.

19. A method as recited in embodiment 18, wherein the treatment location comprises a BVN of the vertebrae, the method further comprising: delivering treatment to the treatment location to denervate at least a portion of the BVN.

20. A method as recited in embodiment 19, wherein denervating a portion of the BVN comprises delivering focused, therapeutic heating to an isolated region of the BVN.

21. A method as recited in embodiment 19, wherein denervating a portion of the BVN comprises delivering an agent to the treatment region to isolate treatment to that region.

22. A method as recited in embodiment 19, wherein the treatment is focused on a location of the BVN that is downstream of one or more branches of the BVN.

23. A kit for channeling a path into bone, comprising: a trocar having a central channel and opening at its distal tip; and a cannula selected from a set of cannulas sized to be received in said central channel and delivered to said distal opening; the cannula having a deflectable distal tip with a preformed curve such that the tip straightens while being delivered through the trocar and regains its preformed curve upon exiting and extending past the distal opening of the trocar to generate a curved path in the bone corresponding to the preformed curve of the deflectable tip; wherein the cannula comprises a central passageway having a diameter configured allow a treatment device to be delivered through the central passageway to a location beyond the curved path; wherein the set of cannulas comprises one or more cannulas that have varying preformed curvatures at the distal tip.

24. A kit as recited in embodiment 23, wherein the one or more cannulas have a varying preformed radius at the distal tip.

25. A kit as recited in embodiment 23, wherein the one or more cannulas each have distal tips that terminate at varying angles with respect to the central channel of the trocar.

26. A kit as recited in embodiment 25, wherein the angle of the distal tip with respect to the central channel of the trocar varies from approximately 45° to approximately 110°.

27. A kit as recited in embodiment 23, further comprising: a straight stylet configured to be installed in the trocar; the straight stylet comprising a sharp distal tip that is configured to extend beyond the distal opening of the trocar to pierce the bone as the trocar is being delivered to a treatment location within the bone.

28. A kit as recited in embodiment 23, further comprising: a set of curved stylets having an outer radius sized to fit within the central passageway of the curved cannula; wherein each curved stylet is configured to be installed in the curved cannula while the curved cannula is extended past the distal opening of the trocar; wherein the curved stylet configured to block the distal opening of the curved cannula while being delivered into the bone; and wherein each curved stylet has a varying a curved distal end corresponding to the curve of a matching curved cannula in the set of curved cannulas.

29. A kit as recited in embodiment 28, wherein the curved stylet has a sharp distal tip configured to extend past the curved cannula to pierce the bone as the cannula is delivered past the distal opening of the trocar.

30. A kit as recited in embodiment 28, wherein the curved stylet and the curved cannula have mating proximal ends that align the curve of the curved stylet with the curve of the curved cannula.

31. A kit as recited in embodiment 28, further comprising a set of straight channeling stylets; wherein one of the set of stylets is configured to be installed in the cannula after removing the curved stylet; wherein the straight channeling stylet is flexibly deformable to navigate the curved cannula yet retain a straight form upon exiting the curve cannula; wherein each of the straight channeling stylets has a varying length longer than the curved cannula such that the straight channeling stylet creates a predetermined-length linear path beyond the distal end of the curved cannula when fully extended.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A method for treating a basivertebral nerve in a vertebral body of a patient, the method comprising:
   inserting an introducer having a handle coupled to a shaft defining a central channel and an opening at a distal tip through a pedicle of the vertebral body until the opening reaches the cancellous bone of the vertebral body;
   delivering a cannula having a proximal end, a rotatable member, and a distal end through the central channel of the introducer, wherein the cannula distal end is deflectable relative to a central axis of the introducer;
   advancing the cannula and a first stylet coupled with the cannula distal end further into the cancellous bone while rotating the rotatable member;
   extending the cannula and the first stylet past the opening at the distal tip of the introducer to generate a curved path in the cancellous bone; and
   via a treatment device coupled with the cannula distal end, delivering treatment to a treatment location proximate the basivertebral nerve.

2. The method of claim 1, wherein inserting the introducer comprises:
   inserting a second stylet into the introducer such that the second stylet extends beyond the opening of the introducer;
   inserting the second stylet and the introducer simultaneously such that the second stylet pierces the bone as the introducer is being delivered through the pedicle.

3. The method of claim 1, wherein delivering the cannula through the central channel comprises:
   inserting a straightening stylet into a central passageway of the cannula, wherein the central passageway of the cannula is distinct from the central channel of the introducer; the straightening stylet comprising a rigid construction configured to straighten the cannula;
   inserting the straightening stylet and the cannula simultaneously into the central channel of the introducer; and
   removing the straightening stylet from the cannula.

4. The method of claim 3:
   wherein the straightening stylet further comprises a sharp distal end to pierce the cancellous bone;

wherein the sharp distal end extends beyond an opening at the distal tip of the cannula; and wherein the straightening stylet and the cannula are installed simultaneously along with the introducer as the introducer is delivered into the cancellous bone.

5. The method of claim 1, wherein extending the cannula past the opening at the distal tip of the introducer comprises:

inserting the first stylet into a central passageway of the cannula such that a distal tip of the first stylet extends to at least an opening at the distal tip of the cannula, wherein the central passageway of the cannula is distinct from the central channel of the introducer; and simultaneously extending the cannula and the first stylet from the distal end of the introducer such that the first stylet blocks the open distal tip of the cannula while being delivered into the cancellous bone.

6. The method of claim 5, further comprising removing the first stylet from the cannula.

7. The method of claim 1 further comprising delivering treatment sufficient to denervate at least a portion of the basivertebral nerve.

8. The method of claim 7, wherein delivering the treatment comprises delivering focused, therapeutic heating to the basivertebral nerve.

9. The method of claim 7, wherein delivering the treatment comprises delivering an agent to the treatment location.

10. The method of claim 7, wherein delivering the treatment to the treatment location to denervate at least the portion of the basivertebral nerve comprises delivering radiofrequency energy.

11. The method of claim 7, wherein delivering the treatment to the treatment location to denervate at least the portion of the basivertebral nerve comprises delivering ultrasonic energy.

12. A method for treating a basivertebral nerve in a vertebral body of a patient, the method comprising:

inserting an introducer through a cortical bone region of a pedicle and into a cancellous bone region of the vertebral body, wherein the introducer has a central channel along its longitudinal axis and an axial opening at a distal tip of the introducer;

delivering a cannula having a proximal end, a rotatable member, and a distal end through the central channel of the introducer to the axial opening at the distal tip of the introducer, wherein the cannula distal end is deflectable relative to a central axis of the introducer;

advancing the cannula and a first stylet coupled with the cannula distal end further through the cortical bone region and into the cancellous bone region while rotating the rotatable member;

extending the cannula and the first stylet past the axial opening at the distal tip of the introducer to generate a curved path through a portion of the cancellous bone toward the basivertebral nerve, via a treatment probe coupled with the cannula distal end and positioned proximate the basivertebral nerve, delivering treatment to the basivertebral nerve.

13. The method of claim 12, wherein the treatment probe comprises a radiofrequency energy delivery probe.

14. The method of claim 12, wherein the treatment probe comprises an ultrasonic energy delivery probe.

15. The method of claim 12, further comprising treating the basivertebral nerve posterior to a basivertebral nerve junction.

16. The method of claim 12, wherein the step of inserting the introducer through the cortical bone region of the pedicle and into the cancellous bone region of the vertebral body comprises:

inserting a second stylet into the introducer such that the second stylet extends beyond the axial opening of the introducer; and inserting the second stylet and introducer simultaneously into the vertebral body such that the second stylet pierces cancellous bone within the cancellous bone region as the introducer is being delivered toward the basivertebral nerve.

17. The method of claim 12, wherein the step of extending the cannula past the axial opening at the distal tip of the introducer comprises:

inserting the first stylet into a central passageway of the cannula such that a distal tip of the first stylet extends to at least an opening at the distal tip of the cannula, wherein the central passageway of the cannula is distinct from the central channel of the introducer; and simultaneously extending the cannula and the first stylet from the distal end of the introducer such that the first stylet blocks the open distal tip of the cannula while being delivered into the vertebral body.

* * * * *